United States Patent
Haley et al.

(10) Patent No.: US 9,876,182 B2
(45) Date of Patent: Jan. 23, 2018

(54) THIENO-CONTAINING COMPOUNDS AND PROCESSES AND USES THEREOF

(71) Applicant: University of Oregon, Eugene, OR (US)

(72) Inventors: Michael M. Haley, Eugene, OR (US); Aaron G. Fix, Florence, AZ (US); Gabriel E. Rudebusch, Eugene, OR (US)

(73) Assignee: University of Oregon, Eugene, OR (US)

( * ) Notice: Subject to any disclaimer, the term of this patent is extended or adjusted under 35 U.S.C. 154(b) by 0 days.

(21) Appl. No.: 14/907,525

(22) PCT Filed: Jul. 25, 2014

(86) PCT No.: PCT/US2014/048262
§ 371 (c)(1),
(2) Date: Jan. 25, 2016

(87) PCT Pub. No.: WO2015/013656
PCT Pub. Date: Jan. 29, 2015

(65) Prior Publication Data
US 2016/0164011 A1    Jun. 9, 2016

Related U.S. Application Data

(60) Provisional application No. 62/023,803, filed on Jul. 11, 2014, provisional application No. 61/859,133, filed on Jul. 26, 2013.

(51) Int. Cl.
C07D 495/22 (2006.01)
H01L 51/00 (2006.01)
(Continued)

(52) U.S. Cl.
CPC ........ *H01L 51/0094* (2013.01); *C07F 7/0812* (2013.01); *H01L 51/0074* (2013.01);
(Continued)

(58) Field of Classification Search
CPC . H01L 51/0094; H01L 51/5096; H01L 51/42; H01L 51/0074; H01L 51/5056;
(Continued)

(56) References Cited

U.S. PATENT DOCUMENTS

| | | | |
|---|---|---|---|
| 7,208,567 | B2 | 4/2007 | Oguma et al. |
| 2010/0331550 | A1 | 12/2010 | Moawia et al. |
| 2013/0096336 | A1 | 4/2013 | Haley et al. |
| 2013/0150592 | A1 | 6/2013 | Haley et al. |

FOREIGN PATENT DOCUMENTS

| | | |
|---|---|---|
| WO | WO 2011/159763 | 12/2011 |
| WO | WO 2013/010614 | 1/2013 |

OTHER PUBLICATIONS

International Search Report issued in International Application No. PCT/US2014/048262 dated Nov. 14, 2014, 2 pages.
(Continued)

*Primary Examiner* — Taylor V Oh
(74) *Attorney, Agent, or Firm* — Klarquist Sparkman, LLP

(57) ABSTRACT

Disclosed herein are embodiments of thieno-containing compounds suitable for use in electrical devices and/or electrooptical device. Also disclosed herein are methods of making the disclosed compounds, with particular embodiments of the method concerning a novel dione intermediate that may be used to make particular embodiments of the thieno-containing compounds.

13 Claims, 14 Drawing Sheets

(51) Int. Cl.
  *C07F 7/08*   (2006.01)
  *H01L 51/05*  (2006.01)
  *H01L 51/42*  (2006.01)
  *H01L 51/50*  (2006.01)

(52) U.S. Cl.
  CPC .......... *H01L 51/0558* (2013.01); *H01L 51/42* (2013.01); *H01L 51/5056* (2013.01); *H01L 51/5088* (2013.01); *H01L 51/5096* (2013.01); *Y02E 10/549* (2013.01)

(58) Field of Classification Search
  CPC ............. H01L 51/5088; H01L 51/0558; C07F 7/0812; Y02E 10/549
  USPC ..................................................... 549/43, 41
  See application file for complete search history.

(56) References Cited

OTHER PUBLICATIONS

Written Opinion of the International Searching Authority issued in International Application No. PCT/US2014/048262 dated Nov. 14, 2014, 3 pages.

Shi et al. "Antiaromatic bisindeno-[n]thienoacenes with small singlet biradical characters: syntheses, structures and chain length dependent physical properties," Chem. Sci. 2014, 5, 4490-4503, Jul. 11, 2014.

Haley et al. "Quinoidal diindenothienoacenes: synthesis and properties of new functional organic materials," Chem. Sci. 2014, 5, 3627-3633, Jun. 16, 2014.

Haley "Indenofluorenes—A new Class of Electron-Accepting Materials," Presentation given on Jul. 29, 2013.

Magnetic Field (Gauss)

Magnetic Field (Gauss)

Magnetic Field (Gauss)

THIENO-CONTAINING COMPOUNDS AND PROCESSES AND USES THEREOF

CROSS-REFERENCE TO RELATED APPLICATION

This application is the U.S. National Stage of International Application No. PCT/US2014/048262, filed Jul. 25, 2014, which was published in English under PCT Article 21(2), which in turn claims the benefit of the earlier filing date of U.S. Provisional Application No. 61/859,133, filed on Jul. 26, 2013, and U.S. Provisional Application No. 62/023,803, filed on Jul. 11, 2014, each of which is herein incorporated by reference in its entirety.

ACKNOWLEDGMENT OF GOVERNMENT SUPPORT

This invention was made with government support under grant numbers NSF CHE-1013032, NSF CHE-1301485, NSF CHE-0840478, CHE-0923589, and OCI-0960354, awarded by the National Science Foundation. The government has certain rights in the invention.

BACKGROUND

Acenes are an exciting class of compounds that have been intensely studied during the past decade. Their alluring optoelectronic properties suggest great potential as the conducting organic material in a variety of device applications such as organic light-emitting diodes (OLEDs), field-effect transistors (OFETs), and solar cells. Pentacene and its derivatives have received the vast amount of attention as this molecule has been hailed as the benchmark for thin film devices. Unfortunately, pentacene readily oxidizes to its respective quinone in aerobic conditions and reacts with itself to afford a butterfly dimer. The driving force for both reactions is the formation of two aromatic naphthalene units which ultimately disrupts overall conjugation and thus leads to poor device performance. While ethynylogation or substitution with thioethers will in general slow degradation, these processes are not completely suppressed.

In addition, in the solid state pentacene packs in an edge-to-face or 'Herring Bone' conformation, which eliminates the possibility of intermolecular π-orbital interactions. Such interactions are crucial for efficient electron transfer, an important characteristic for improving device functionality and performance.

SUMMARY

Disclosed herein are compounds having any one of the formulas provided below.

Formula 1(A)

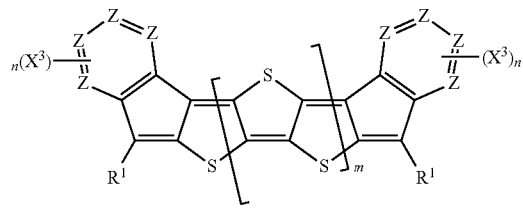

Formula (1)B

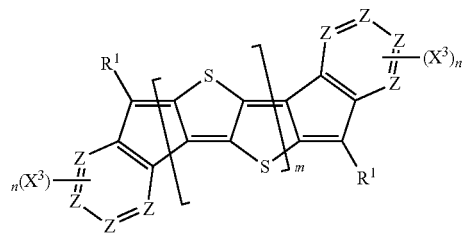

Formula 1(A)(i)

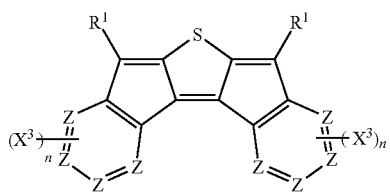

Formula 1(B)(i)

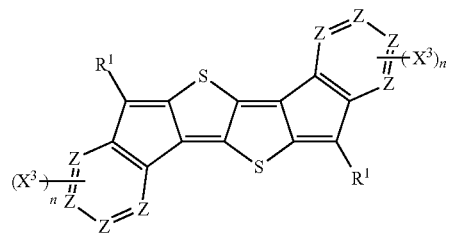

Formula 1(A)(ii)

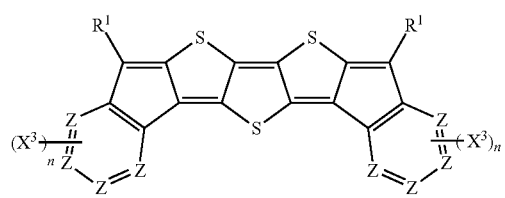

Formula 1(B)(ii)

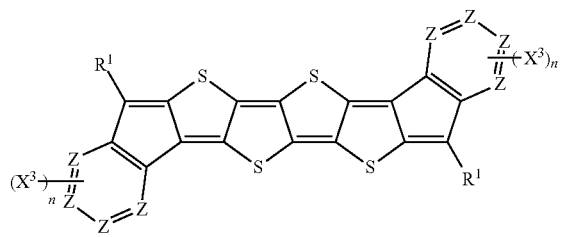

Formula 2

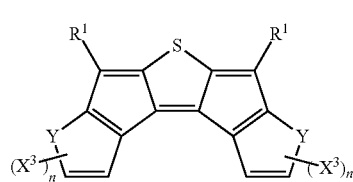

Formula 2(A)

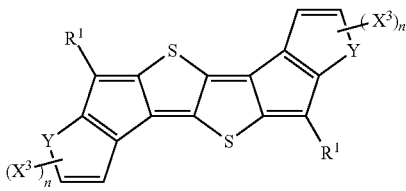

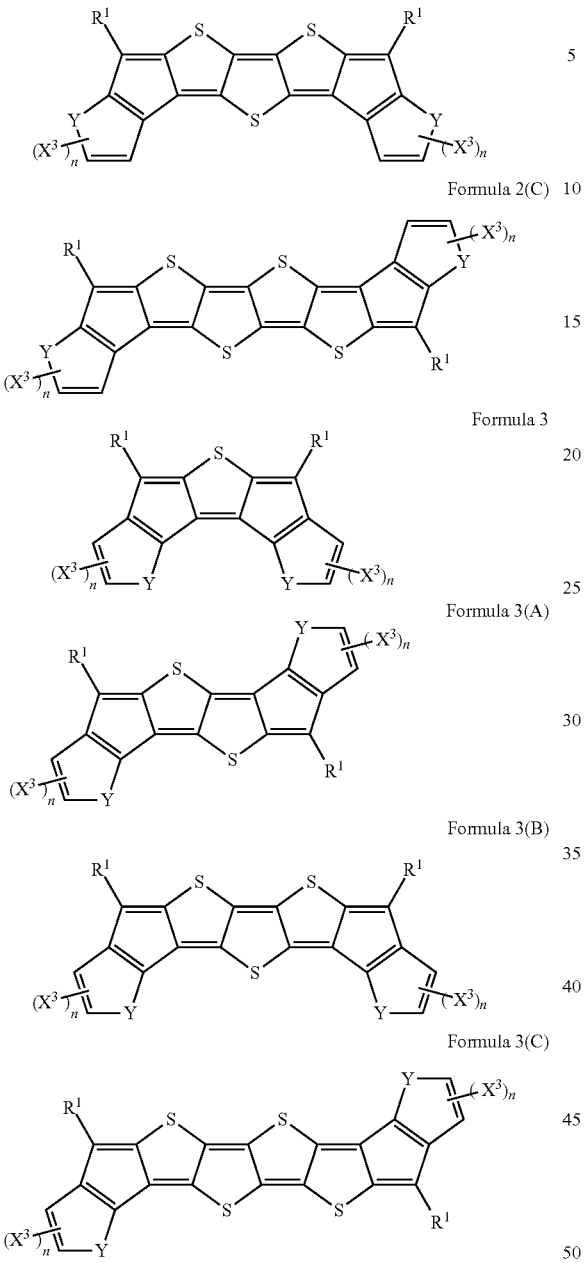

Formula 2(B)
Formula 2(C)
Formula 3
Formula 3(A)
Formula 3(B)
Formula 3(C)

According to any one of the formula provided above, each $R^1$ independently is selected from alkynyl, substituted alkynyl, aryl, substituted aryl, heteroaryl, or substituted heteroaryl; each Y independently is selected from sulfur, oxygen, or $NR^2$, wherein $R^2$ may be selected from hydrogen, alkyl, alkenyl, alkynyl, cycloalkyl, cycloalkenyl, aryl, and heteroaryl; each Z independently can be selected from carbon or nitrogen; each $X^3$ independently is selected from halogen, alkyl, alkenyl, alkynyl, aryl, heteroaryl, cycloalkyl, heteroalkyl, cycloheteroalkyl, amino, haloalkyl, alkoxy, hydroxy, amide, nitro, azide, carboxyl, ester, ether, thiol, thioether, and cyano; each n independently can be 0, 1, 2, 3, or 4; and each m independently can be 0 to 10, such as 0, 1, 2, 3, 4, 5, 6, 7, 8, 9, or 10. In some embodiments, m is 0 or 1 for Formula 1(A) and m is 1 or 2 for Formula 1(B).

Also disclosed herein are embodiments of a novel dione precursor that may be used to synthesize compounds having a Formula 2 and/or Formula 3. The novel precursor has a Formula 4, illustrated below.

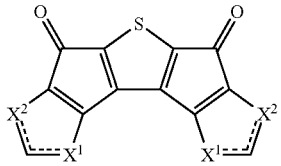

Formula 4

With reference to Formula 4, each of $X^1$ and $X^2$ independently is selected from carbon, sulfur, oxygen, or $NR^2$, wherein $R^2$ may be selected from hydrogen, alkyl, alkenyl, alkynyl, cycloalkyl, cycloalkenyl, aryl, and heteroaryl. At least one olefin is present in the ring bearing $X^1$ and $X^2$, with the position of this olefin being selected to accommodate the valency of each one of $X^1$ and $X^2$.

The compounds disclosed herein have important chemical, electrical, and structural characteristics, which make them unique compounds for semiconductor applications. In particular disclosed embodiments, the compounds may be used in electronic and/or electrooptical devices.

The foregoing will become more apparent from the following detailed description, which proceeds with reference to the accompanying figures.

DETAILED DESCRIPTION

Terminology

Figure 1:
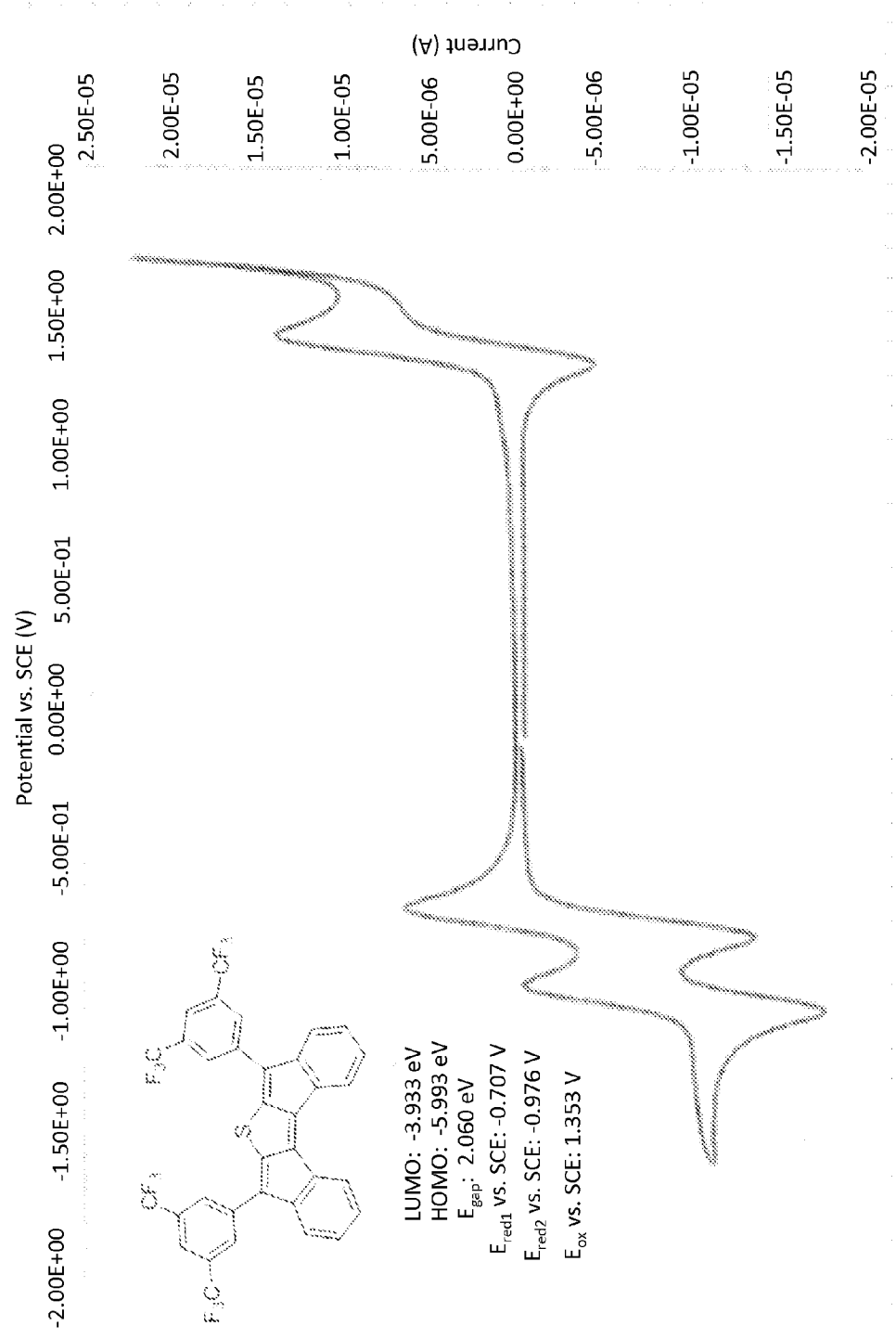
FIG. 1 is an image of a current-voltage curve for a particular embodiment of the disclosed compounds having a Formula 1(A).

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods, as known to those of ordinary skill in the art. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided:

The term "alkyl" can refer to a branched or unbranched saturated hydrocarbon group of 1 to 50 carbon atoms, such as 1 to 25 carbon atoms, or 1 to 15 carbon atoms. In an independent embodiment, alkyl can include, but is not limited to, methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group can be a saturated branched or unbranched hydrocarbon having from 1 to 10 carbon atoms, such as 1 to 4 carbon atoms. In an independent embodiment, an alkyl groups may be a "substituted alkyl" wherein one or more hydrogen atoms are substituted with a substituent other than hydrogen, such as those disclosed herein.

The term "alkylaryl" can refer to a group in which an alkyl group is substituted for a hydrogen atom of an aryl group. An example is —Ar—R, wherein Ar is an arylene group and R is an alkyl group.

The term "alkynyl" can refer to a hydrocarbon group of 2 to 50 carbon atoms, such as 2 to 25 carbon atoms, or 2 to 15 carbon atoms, and a structural formula comprising at least one carbon-carbon triple bond.

The term "alkenyl" can refer to a hydrocarbon group of 2 to 50 carbon atoms, such as 2 to 25 carbon atoms, or 2 to 15 carbon atoms and a structural formula comprising at least one carbon-carbon double bond.

The term "alkoxy" can refer to a straight, branched or cyclic hydrocarbon configuration and combinations thereof, including from 1 to 20 carbon atoms, such as from 1 to 10 carbon atoms, or from 1 to 4 carbon atoms, which includes an oxygen atom at the point of attachment. In an independent embodiment, an "alkoxy group" is represented by the formula —OR, where R can be an alkyl group, optionally substituted with any one of the substituents disclosed herein, with examples including, but not limited to, an alkenyl, alkynyl, aryl, aralkyl, cycloalkyl, halogenated alkyl, or heterocycloalkyl group as described herein. In an independent embodiment, an alkoxy group can be selected from methoxy, ethoxy, n-propoxy, i-propoxy, n-butoxy, i-butoxy, sec-butoxy, tert-butoxy cyclopropoxy, cyclohexyloxy, and the like.

The term "amine" or "amino" can refer to a group of the formula —NRR', where R and R' can be, independently, hydrogen or an alkyl, alkenyl, alkynyl, aryl, aralkyl, cycloalkyl, halogenated alkyl, aryl, heteroaryl, or heterocycloalkyl group. In an independent embodiment, an "alkylamino" or "alkylated amino" can refer to —NRR', wherein at least one of R or R' is an alkyl.

The term "aralkyl" can refer to an alkyl group that has at least one hydrogen atom replaced by an aryl group. An example of an aralkyl group is a benzyl group.

The term "aryl" can refer to any carbon-based aromatic group. In an independent embodiment, an aryl group can be, but is not limited to, phenyl, naphthyl, etc. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "cycloalkyl" can refer to a non-aromatic carbon-based ring composed of at least three carbon atoms to 15 carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous. "Heterocycloalkyl" and "heterocyclic" can be used interchangeably herein.

The terms "halogenated alkyl" or "haloalkyl group" can refer to an alkyl group as defined above with one or more hydrogen atoms present on these groups substituted with a halogen (F, Cl, Br, I).

The term "heteroaryl" can refer to an aromatic group that has at least one heteroatom incorporated within the ring of the aromatic group. Examples of heteroatoms include, but are not limited to, nitrogen, oxygen, sulfur, and phosphorous.

The term "hydroxyl" is represented by the formula —OH.

The term "thioether" can refer to a —S—R group, wherein R may be, for example, alkyl, or aryl.

The term "thiol" can refer to —SH.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated herein. In an independent embodiment, the term "substituted" can refer to replacing at least one hydrogen atom of the particular substituent with a different group, such as but not limited to, halogen, alkyl, alkenyl, alkynyl, aryl, heteroaryl, cycloalkyl, heteroalkyl, cycloheteroalkyl, amino, haloalkyl, alkoxy, hydroxy, amide, nitro, azide, carboxyl, ester, ether, thiol, thioether, and cyano.

Introduction

Compounds comprising thieno-based structures and other quinoidal molecules based on the indenofluorene skeleton, or derivatives thereof, can be attractive alternative structural motifs. In some embodiments, every atom in the core unit of a fully conjugated diindenothiophene, as disclosed herein, can be sp2 hybridized. Fully-conjugated diindenothiophene compounds comprising a core ring structure can alter the HOMO-LUMO energy gaps relative to other non-heteroatom containing compounds. Moreover, the disclosed compounds expand the range of wavelength absorption of related compounds. For instance, in certain embodiments of the fully-conjugated core ring structure disclosed herein have red-shifted electronic absorptions (smaller band gap) and electrochemical reductions relative to thieno-containing molecules that are not fully conjugated.

Disclosed herein are embodiments of quinoidal molecules based on the indenofluorene skeleton. Certain of the compound embodiments disclosed herein exhibit absorption profiles and amphoteric redox behavior that make the compounds useful for the applications disclosed herein. Certain exemplary compounds include fully conjugated indacenedithiophenes, where thiophenes replace the outer benzene rings of indeno[1,2-b]fluorenes. Also disclosed are embodiments of compounds where the bridging sp2 carbon units in indeno[2,1-c]fluorene and fluoreno[4,3-c]fluorene is exchanged with isoelectronic sulfur atoms. Sulfur incorporation into the framework of polycyclic hydrocarbon can provide a versatile method to promote good solid-state ordering and improve stability at ambient conditions.

Compounds

Disclosed herein are embodiments of thieno-containing compounds. In some embodiments, the thieno-containing compounds can be diindenothiophene compounds having any one of the following formulas. The compounds disclosed herein can have 1 to 10 central sulfur-containing rings, such as 1 to 8, 1 to 6, or 1-4 central sulfur-containing rings.

Formula 1(A)

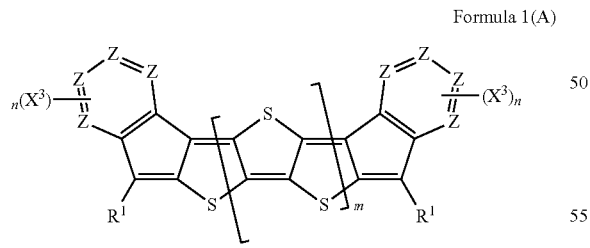

Formula (1)B

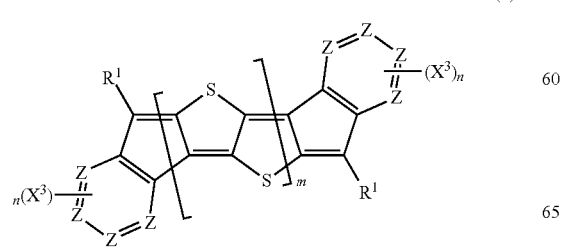

Formula 1(A)(i)

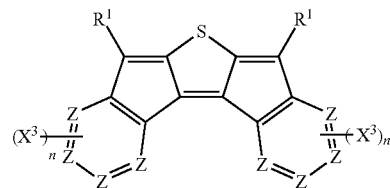

Formula 1(B)(i)

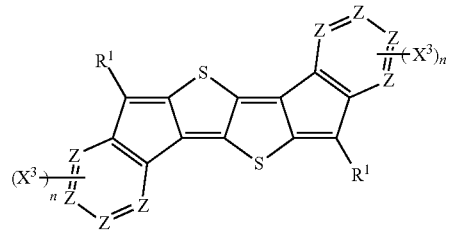

Formula 1(A)(ii)

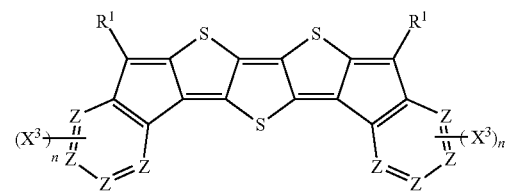

Formula 1(B)(ii)

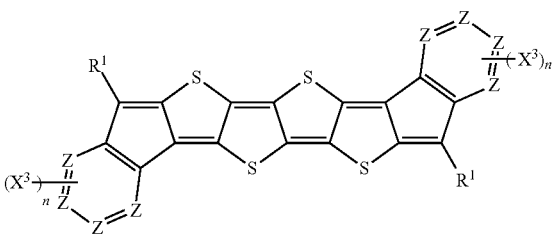

Formula 2

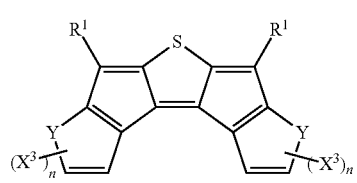

Formula 2(A)

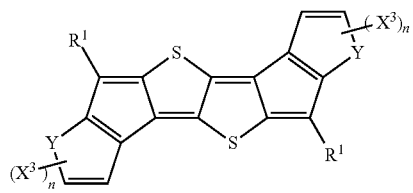

Formula 2(B)

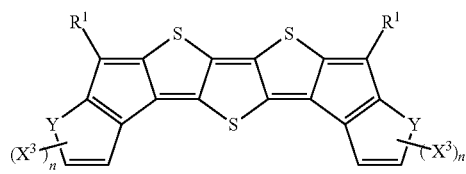

-continued

Formula 2(C)

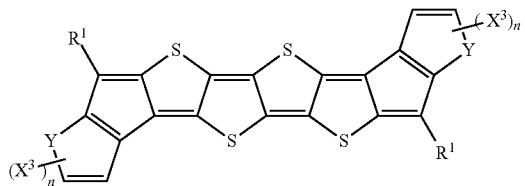

Formula 3

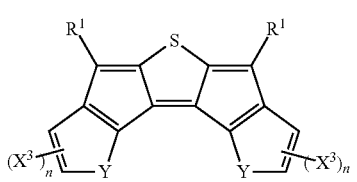

Formula 3(A)

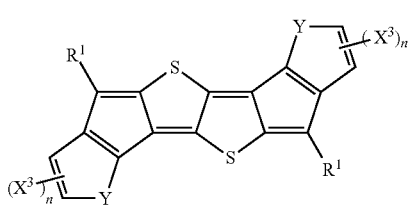

Formula 3(B)

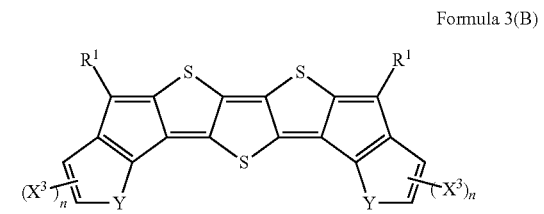

Formula 3(C)

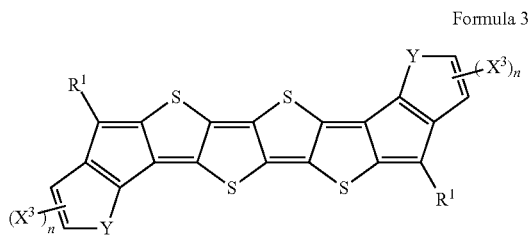

According to any one of the formula provided above, each $R^1$ independently is selected from alkynyl, substituted alkynyl, aryl, substituted aryl, heteroaryl, or substituted heteroaryl; each Y independently is selected from sulfur, oxygen, or $NR^2$, wherein $R^2$ may be selected from hydrogen, alkyl, alkenyl, alkynyl, cycloalkyl, cycloalkenyl, aryl, and heteroaryl; each Z independently can be selected from carbon or nitrogen; each $X^3$ independently is selected from halogen, alkyl, alkenyl, alkynyl, aryl, heteroaryl, cycloalkyl, heteroalkyl, cycloheteroalkyl, amino, haloalkyl, alkoxy, hydroxy, amide, nitro, azide, carboxyl, ester, ether, thiol, thioether, and cyano; each n independently can be 0, 1, 2, 3, or 4; and each m independently can be 0 to 10, such as 0, 1, 2, 3, 4, 5, 6, 7, 8, 9, or 10. In some embodiments, m is 0 or 1 for Formula 1(A) and m is 1 or 2 for Formula 1(B).

In particular disclosed embodiments, each Z is carbon, and each $R^1$ independently may be substituted alkynyl, which includes alkynyl silanes having a formula

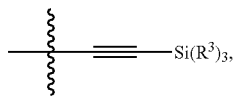

wherein each $R^3$ independently may be selected from alkyl, alkenyl, alkynyl, alkoxy, or aryl. In particular disclosed embodiments, each $R^3$ independently is selected from $C_{1-10}$alkyl or $C_{1-10}$alkoxy. In exemplary embodiments, each $R^3$ is isopropyl, methyl, or ethyl. In other embodiments, the compound may comprise one Z variable on each ring that is nitrogen, with the others being carbon. In yet other embodiments, the compound may comprise two Z variables on each ring that are nitrogen, with the others being carbon.

In other disclosed embodiments, each $R^1$ independently may be selected from substituted aryl, which includes aryl groups comprising one or more, such as 1, 2, 3, 4, or 5 substituents selected from hydrogen, halogen, alkyl, alkenyl, alkynyl, aryl, heteroaryl, cycloalkyl, heteroalkyl, cycloheteroalkyl, amino, haloalkyl, alkoxy, hydroxy, amide, nitro, azide, carboxyl, ester, ether, thiol, thioether, and cyano.

In particular disclosed embodiments, each $R^1$ independently may be selected from substituted aryl, which is substituted with from 1 to 5 substituents selected from fluoro, chloro, bromo, iodo, trifluoromethyl, methyl, or combinations thereof.

Exemplary compounds of the present disclosure are provided below.

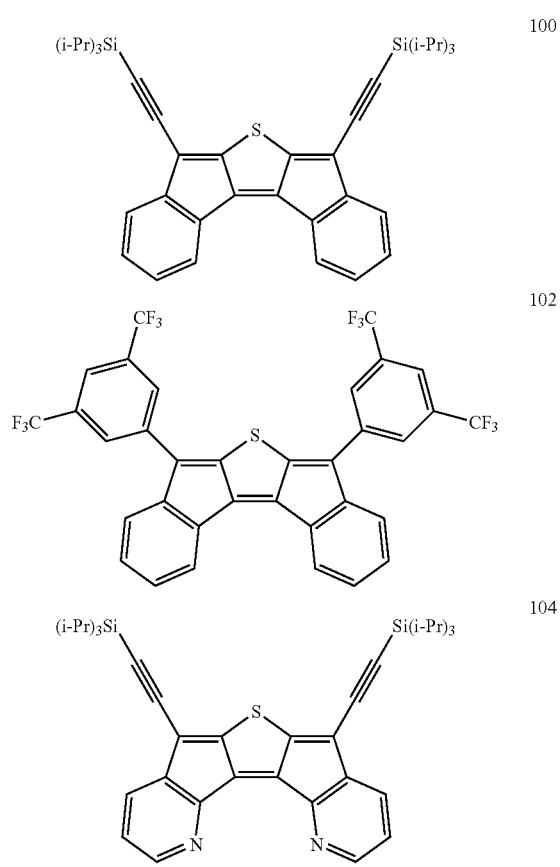

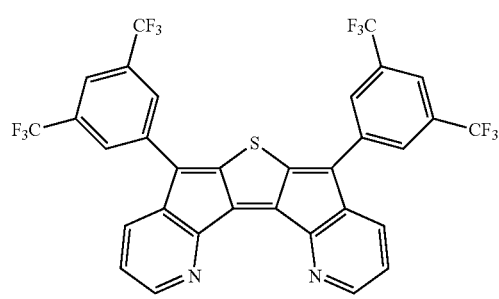
106
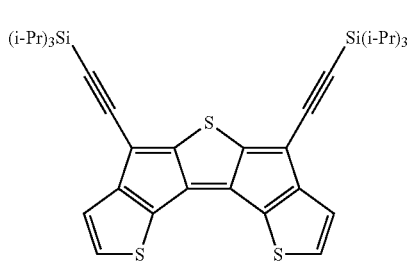
108
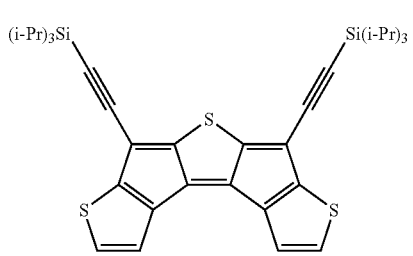
110
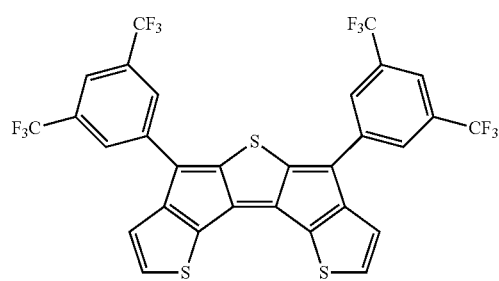
112
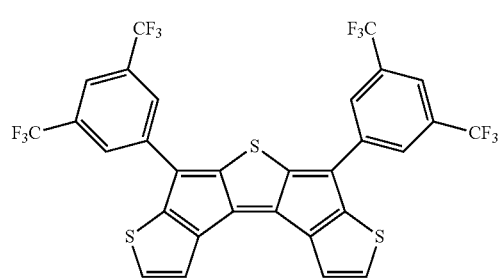
114
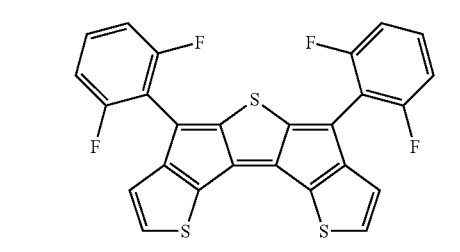
116
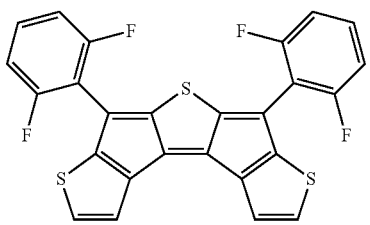
118
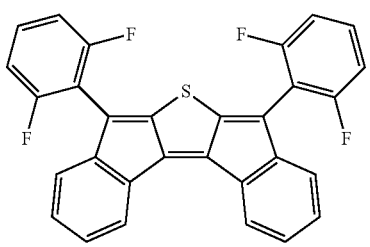
120
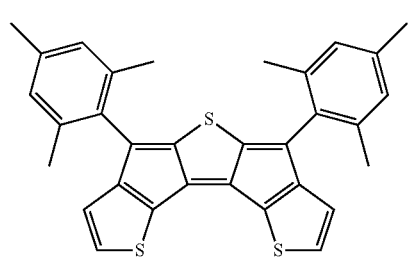
122
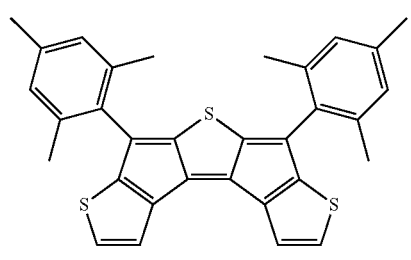
124
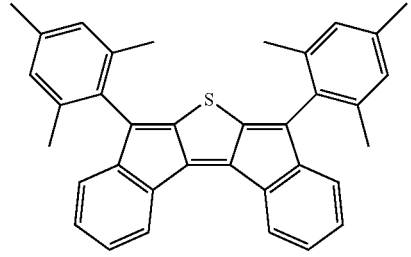
126
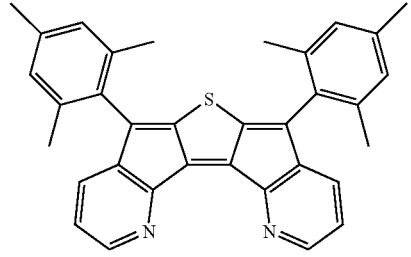
128

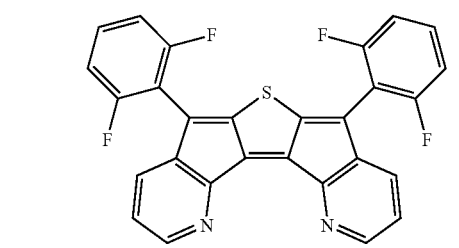
130
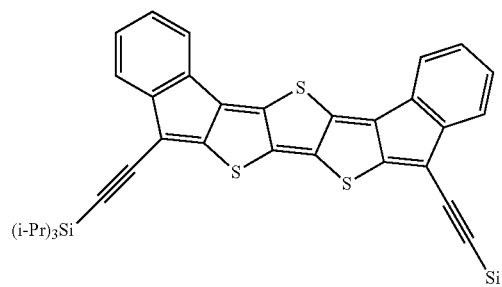
132
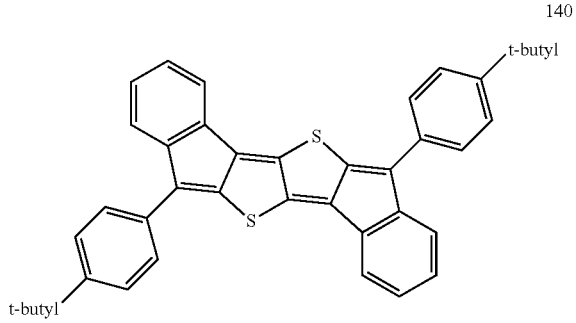
140
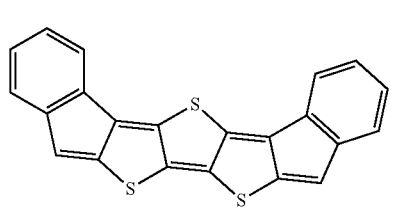
142
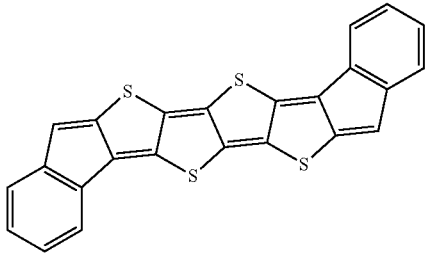
144
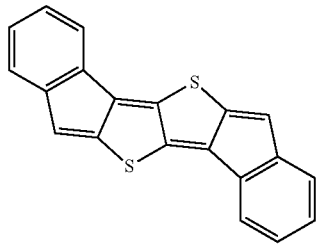
146
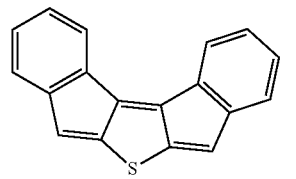
148
134
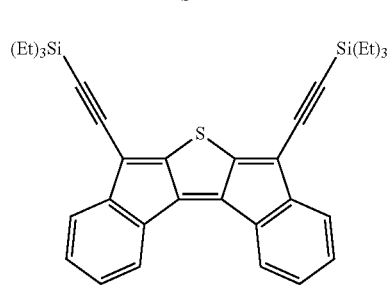
150
136
138

-continued

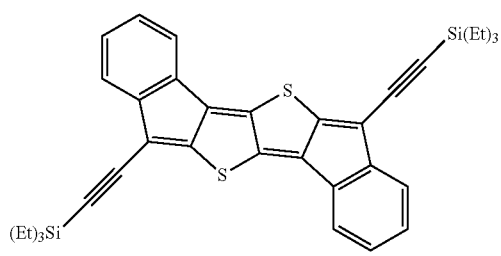
152

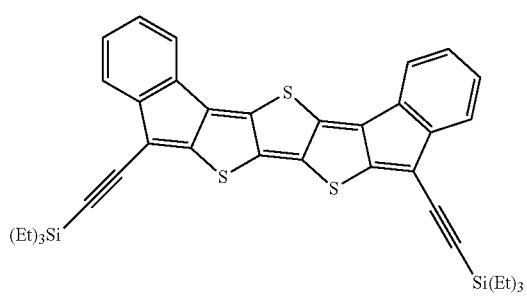
154

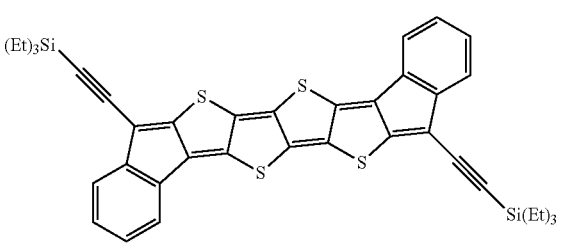
156

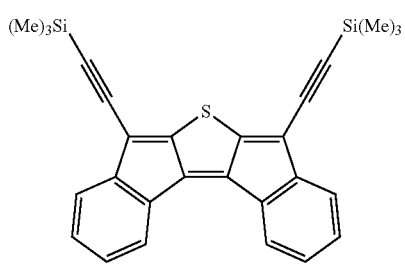
158

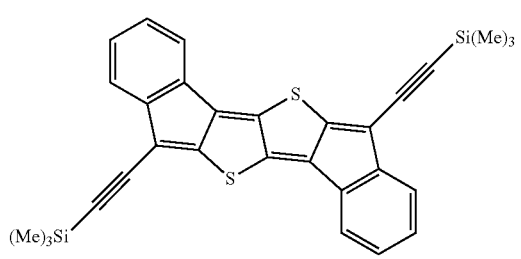
160

-continued

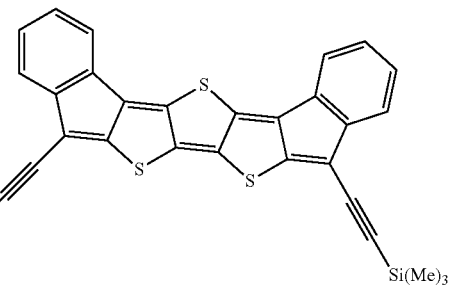
162

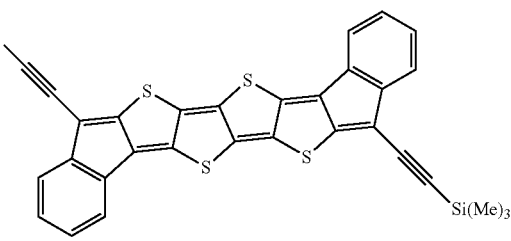
164

Also disclosed herein are methods of making and characterizing the compound embodiments disclosed herein. In some embodiments, the methods disclosed herein provide new methods for making quinoidal thienoacenes through the fusion of electron-accepting indene fragments to a thienoacene core. In some embodiments, methods for making compounds having (trialkylsilyl)ethynyl groups to favor solid-state order can be used, as well as methods for making compounds having aryl and substituted aryl groups, which can facilitate tuning the electronics of the compounds.

In particular disclosed embodiments, thieno-containing compounds disclosed herein can be synthesized from dione precursors. For example, compounds having a Formula 1(A) (e.g., compounds having a Formula 1(A)(i)) can be synthesized from a dione precursor 1 having the structure illustrated below.

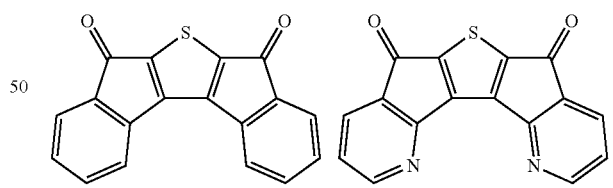

Dione precursors

In particular disclosed embodiments, compounds having a Formula 1(A) (e.g., compounds having a Formula 1(A)(i)) can be synthesized according to the method illustrated in Scheme 1. First, the dione precursor is subjected to a nucleophilic addition reaction wherein a suitable lithiated nucleophile adds into the carbonyl group of the dione, which is subsequently protonated using an acidic work-up step. Addition of heat and a Lewis acid, such as $SnCl_2$, $AlCl_3$, $BF_3OEt_2$, and the like, then provides the desired thieno-containing compound.

Scheme 1

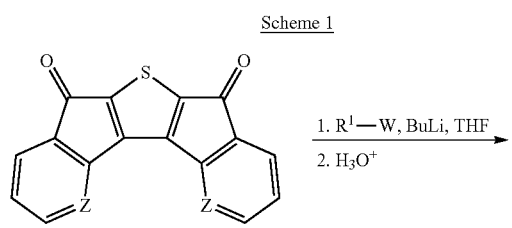

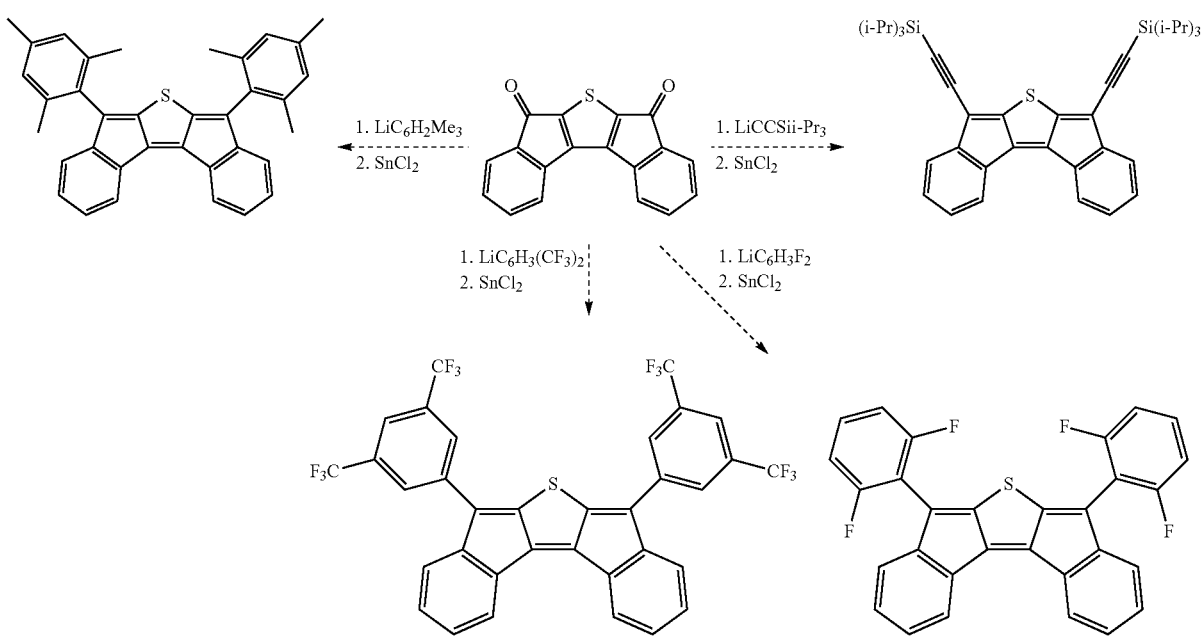

thieno-containing compound. In another embodiment, the dione precursor is exposed to $LiC_6H_3F_2$ and then $SnCl_2$ to provide the di-fluorophenyl functionalized thieno-containing compound illustrated in Scheme 2. In yet another embodiment, the dione precursor may be exposed to $LiC_6H_3(CF_3)_2$ and $SnCl_2$ to provide yet another embodiment of the thieno-containing compounds disclosed herein. In yet a further embodiment, the dione precursor may be exposed to $LiC_6H_2Me_3$ and $SnCl_2$ to provide yet another embodiment of the thieno-containing compounds.

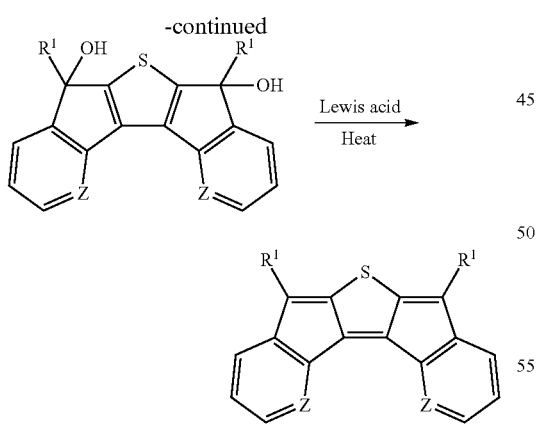

-continued

In other disclosed embodiments, compounds having Formulas 2 and 3 may be made starting with the novel dione precursor of Formula 4 (provided below). This dione precursor may be exposed to similar conditions described above in Scheme 1 in order to provide compounds having a Formula 2 and/or Formula 3.

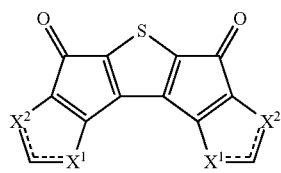

Formula 4

With reference to Scheme 1, $R^1$ is as disclosed herein and W may be selected from a suitable leaving group, such as a halogen (e.g., bromine, fluorine, chlorine, iodine) or triflate.

Particular disclosed compound embodiments may be synthesized using the method provided below in Scheme 2. The dione precursor is exposed to $LiCCSii\text{-}Pr_3$ and then $SnCl_2$ to provide a TIPS-functionalized arylalkyne species of the With reference to Formula 4, each of $X^1$ and $X^2$ independently is selected from carbon, sulfur, oxygen, or $NR^2$, wherein $R^2$ may be selected from hydrogen, alkyl, alkenyl, alkynyl, cycloalkyl, cycloalkenyl, aryl, and heteroaryl.

Exemplary methods of making embodiments of compounds having Formulas 2 and/or 3 are provided below in Schemes 3 and 4. Methods of making other compounds disclosed herein also are provided below in Schemes 5-11.

Scheme 3
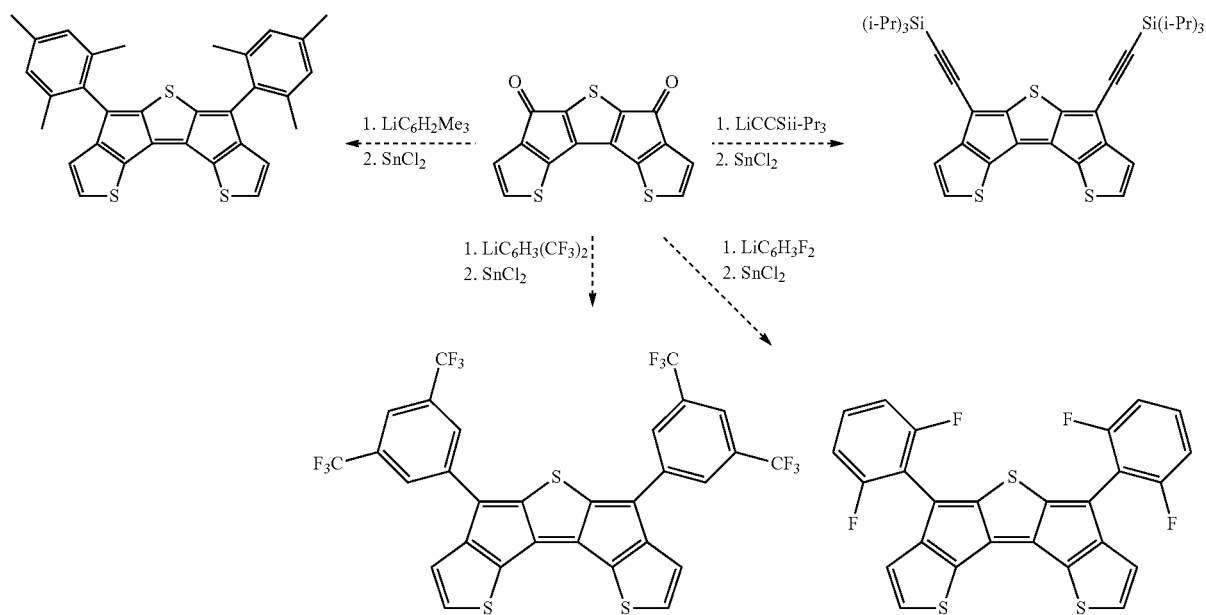
Scheme 4
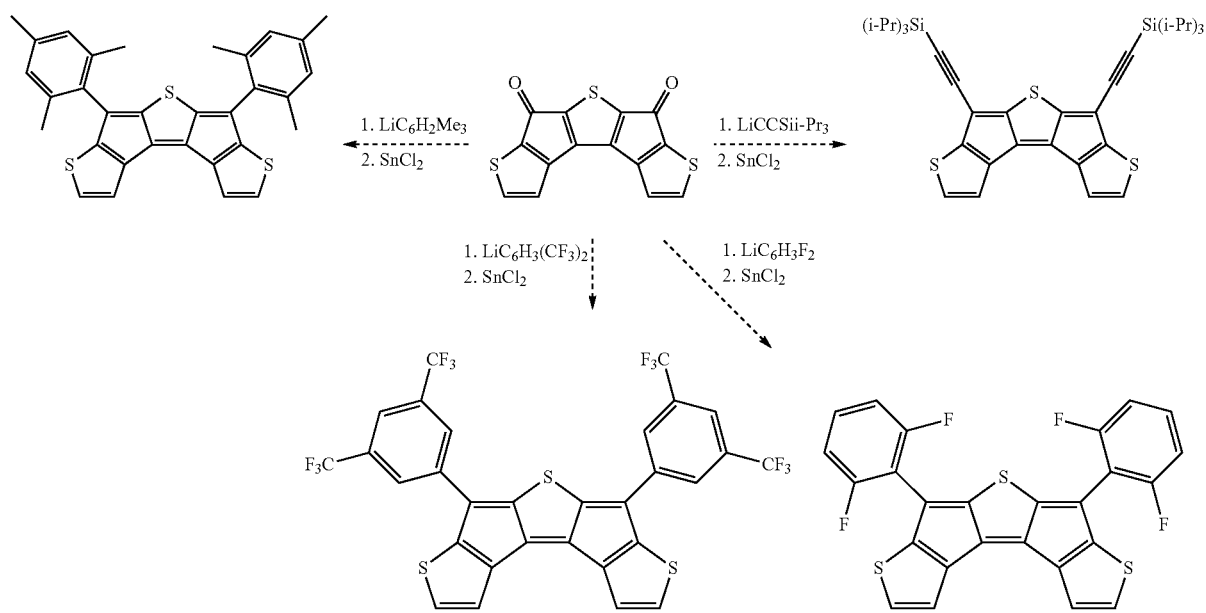
Scheme 5
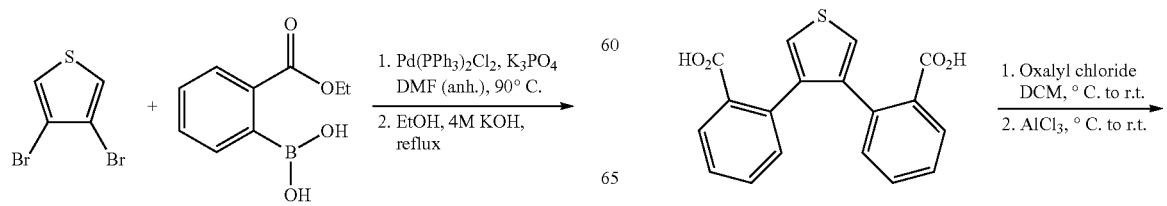
-continued

-continued
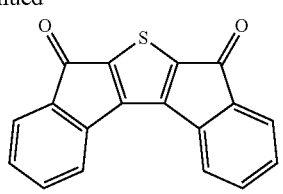
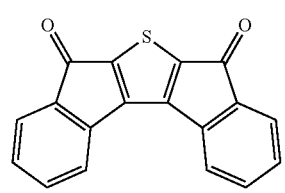
1. R—Li, THF, -78° C. to r.t.
2. SnCl$_2$, CF$_3$CO$_2$H, toluene, rt to Δ
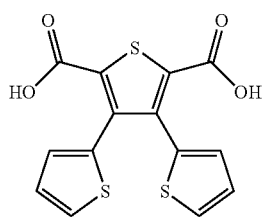
Scheme 6
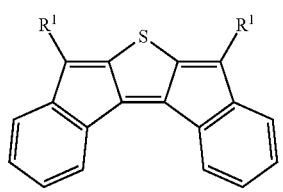
1. Pd(PPh$_3$)$_2$Cl$_2$, K$_3$PO$_4$
   DMF (anh.), 90° C.
2. EtOH, 4M KOH, reflux
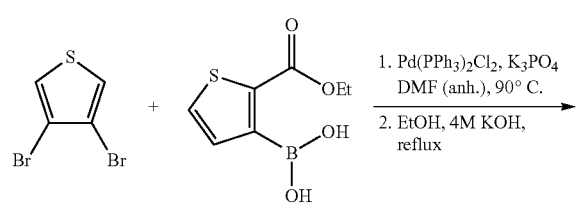
1. Oxalyl chloride
   DCM, ° C. to r.t.
2. AlCl$_3$, ° C. to r.t.
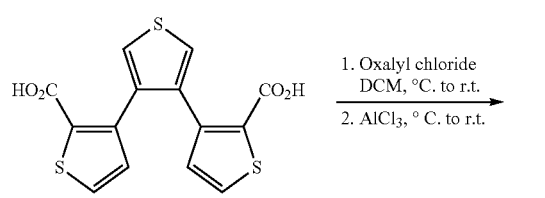
Scheme 7
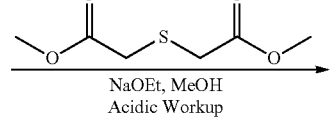
NaOEt, MeOH
Acidic Workup
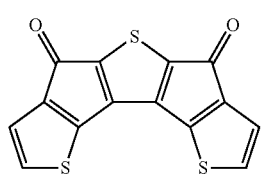
1. Oxalyl chloride
   DCM, ° C. to r.t.
2. AlCl$_3$, ° C. to r.t.
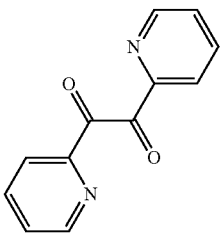
Scheme 8
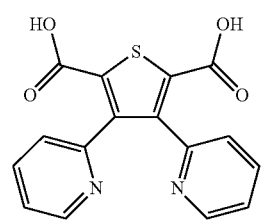
NaOEt, MeOH
Acidic Workup
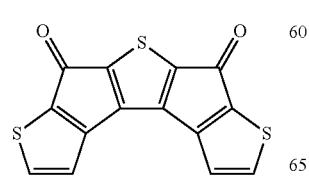
LDA
THF, -78° C. to r.t.

Scheme 9
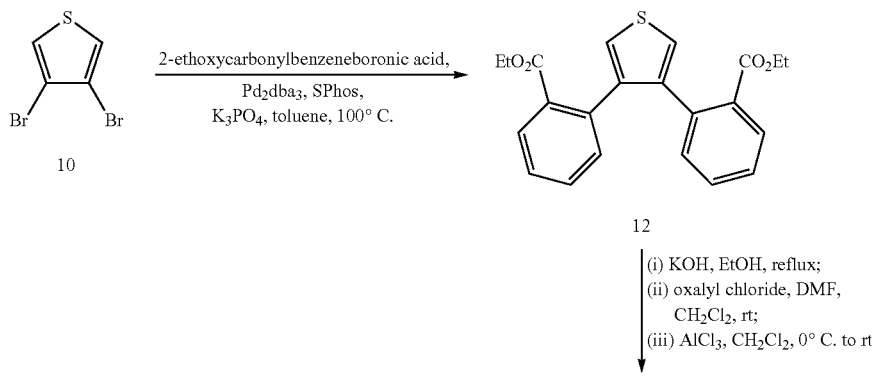
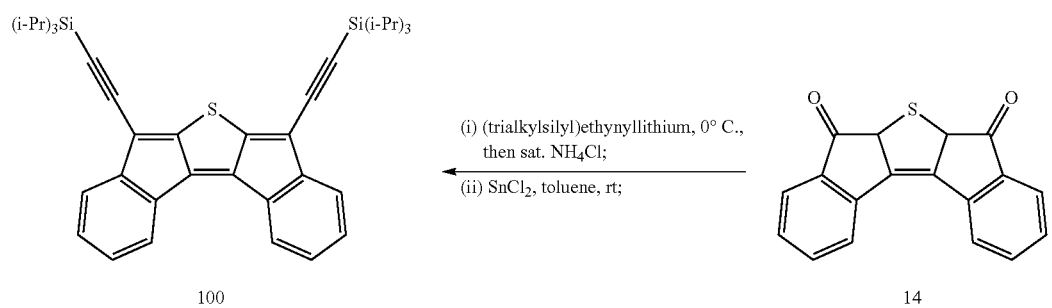
Scheme 10
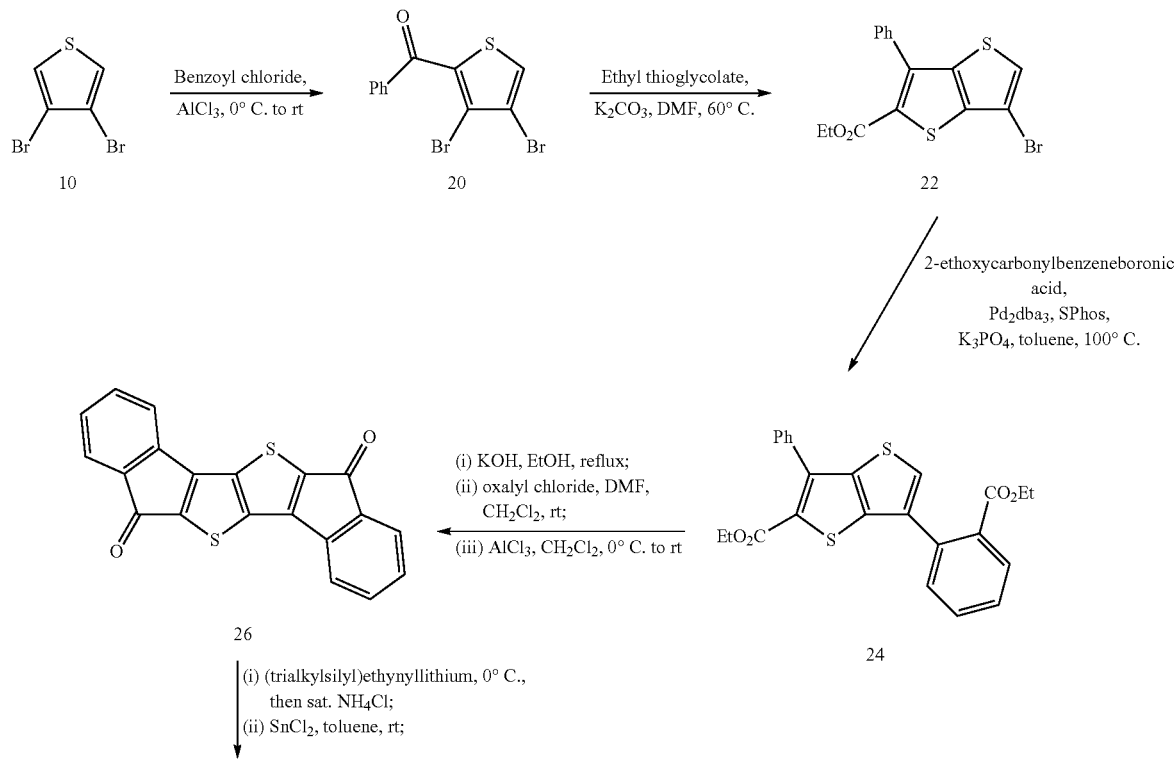

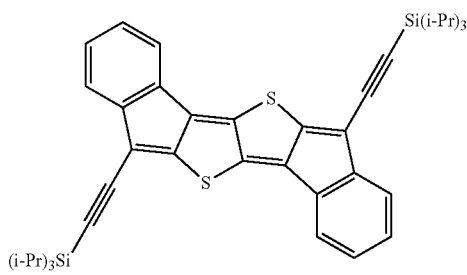

138

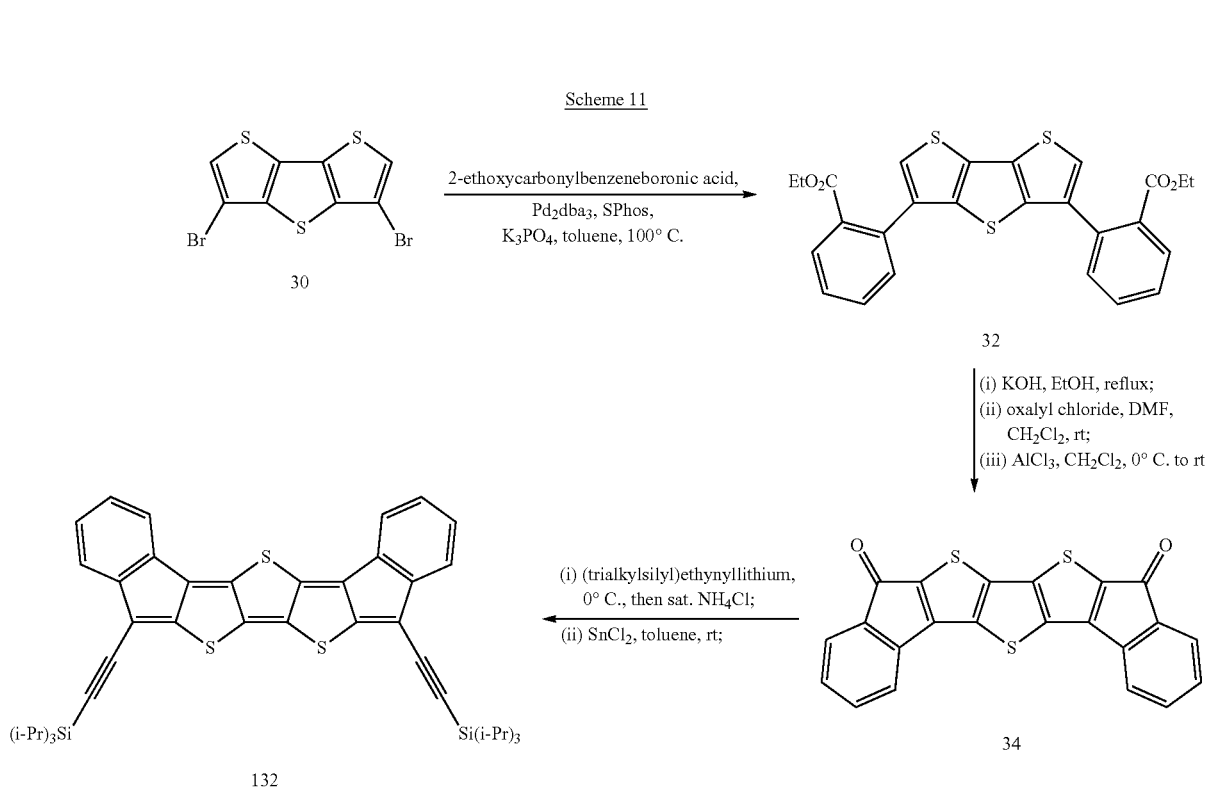

Scheme 11

Compound Applications

Figure 2:
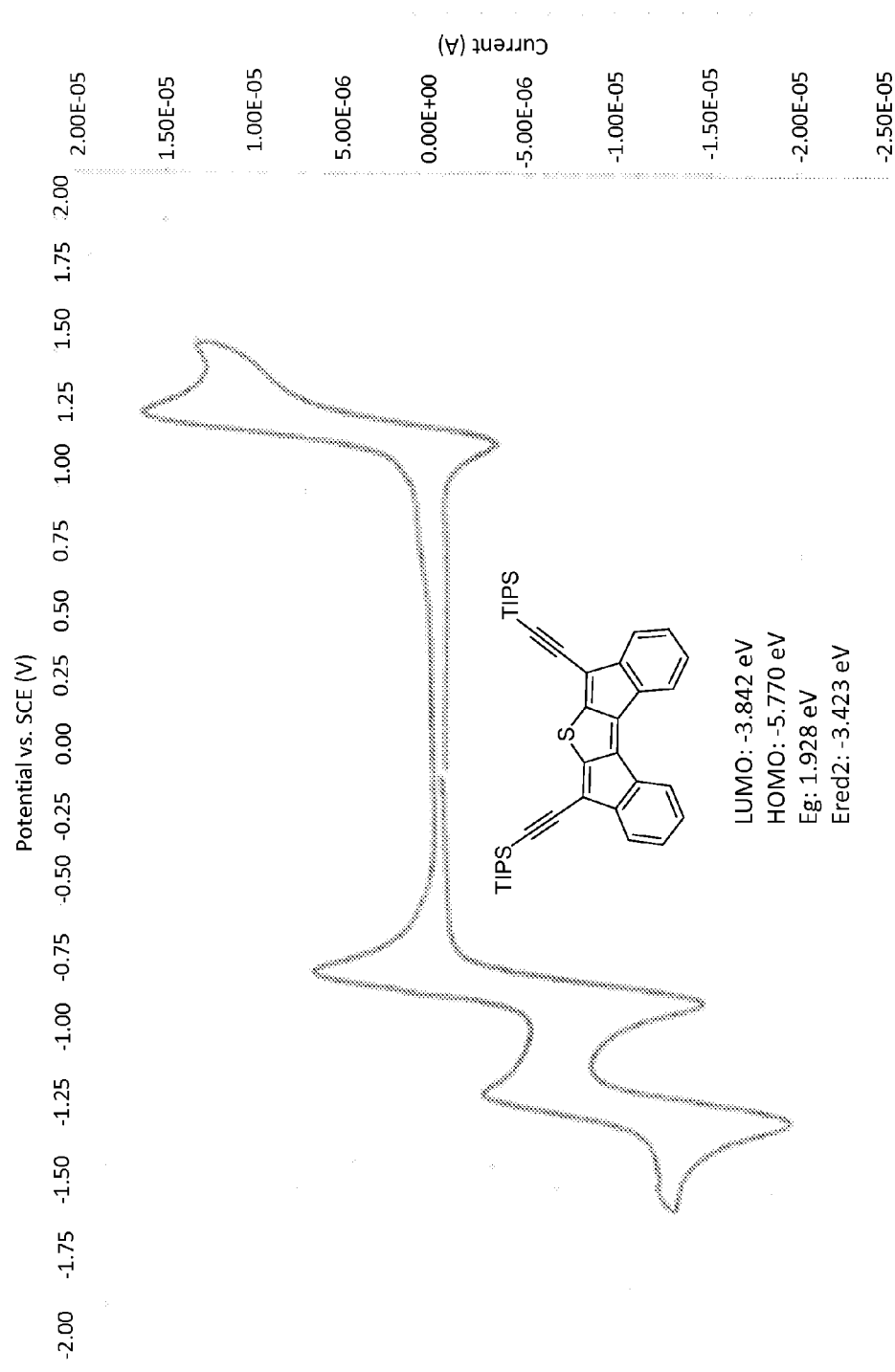
FIG. 2 is an image of a current-voltage curve for a particular embodiment of the disclosed compounds having a Formula 1(A).
Figure 3:
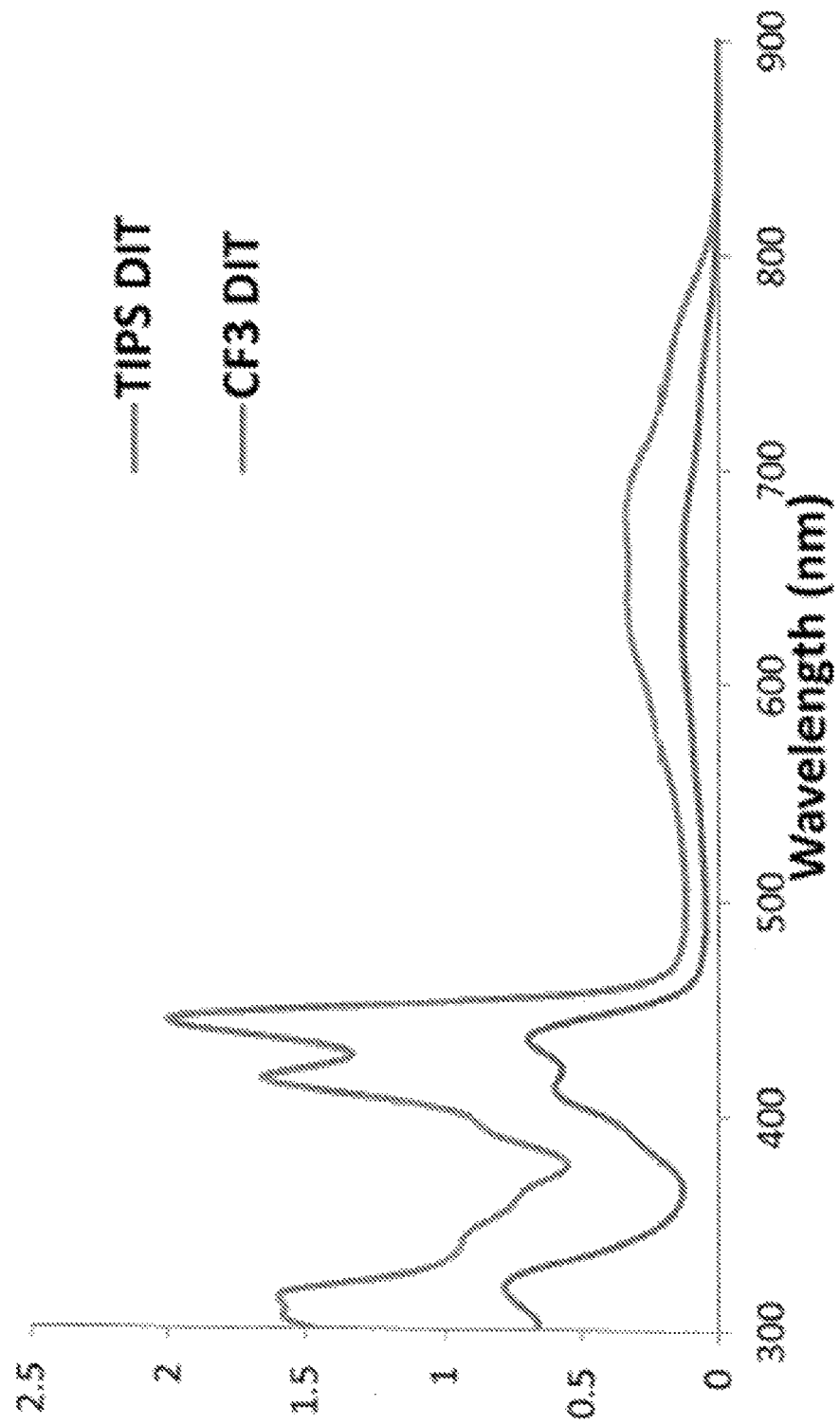
FIG. 3 is an image of a UV-vis spectrum obtained from analyzing particular embodiments of the disclosed compounds having a Formula 1(A).

The thieno-containing compounds disclosed herein may be used in semiconductor applications. Additionally, they may be used in an apparatus comprising, consisting essentially of, or consisting of electronic or electrooptical devices such as, for example, an organic light-emitting diode (OLED), an organic field-effect transistor (OFET), or an organic photovoltaic cell (OPV). Electrical and chemical properties of certain compound embodiments are illustrate in FIGS. 1-3. The thieno-containing compounds disclosed herein may be used as organic semiconductors in the form of thin organic layers or films, for example, less than 30 microns thick. In some embodiments, the semiconducting layer not greater than 1 micron thick, although it may be thicker if required. For various electronic device applications, the thickness may also be less than about 1 micron thick. For use in an OFET, the layer thickness may typically be 500 nm or less, in an OLED it can be 100 nm or less. The exact thickness of the layer will depend, for example, upon the requirements of the electronic device in which the layer is used. In some embodiments, the thin organic layers or films comprising, consisting essentially of, or consisting of one or more of the thieno-containing compounds can be formed by spin-coating, dip-coating, or spraying a solution of the thieno-containing compounds onto a portion of the electronic or electrooptical device of the apparatus embodiments disclosed herein.

In some embodiments, the active semiconductor channel between the drain and source in an OFET may comprise, consist essentially of, or consist of a layer of one or more of the compounds disclosed herein. In other embodiments, a hole injection or transport layer, and or an electron blocking layer in an OLED device may comprise, consist essentially of, or consist of a layer that includes one or more compounds disclosed herein.

In some embodiments, an OFET may comprise, consist essentially of, or consist of: a source electrode, a drain electrode, a gate electrode, a semiconducting layer, one or more gate insulator layers, and (optionally) a substrate, wherein the semiconductor layer comprises, consists essentially of, or consists of one or more of the thieno-containing compounds as described herein.

In certain embodiments the photovoltaic cell includes an anode, a cathode, and a semiconductor layer or film that comprises, consists essentially of, or consists of at least one or more of the thieno-containing compounds disclosed herein.

EXAMPLES

General Information

Air sensitive manipulations were performed by standard Schlenk line technique. THF and toluene were refluxed with sodium benzophenone ketyl for 24 hour prior to distillation and use. $CH_2Cl_2$ was distilled from calcium hydride. All other reagents were used without prior purification. 2-Ethoxycarbonylbenzeneboronic acid was purchased from Synthonix, Inc. (Trialkylsilyl)acetylenes were purchased from GFS Chemicals. Chromatography was performed on 230-400 mesh silica gel purchased from Aldrich. $^1H$ and $^{13}C$ NMR spectra were recorded in $CDCl_3$ using a Varian Inova 500 ($^1H$: 500.11 MHz, $^{13}C$: 125.75 MHz) or Bruker Avance-III-HD 600 ($^1H$: 599.98 MHz, $^{13}C$: 150.87 MHz) NMR spectrometer. Chemical shifts (δ) are expressed in ppm relative to the residual chloroform ($^1H$: 7.26 ppm, $^{13}C$: 77.16 ppm) reference. UV-Vis spectra were recorded on a HP 8453 UV-Vis spectrometer. High resolution mass spectra were recorded on a JEOL MS-Route mass spectrometer.

X-Ray Crystallography.

Diffraction intensities for 100, 138, 150, 14 and 26 were collected at 100(2) K and for 132 at 150(2) K on a Bruker Apex2 CCD diffractometer with a micro-focus IµS source using CuKα radiation λ=1.54178 Å or a sealed X-ray tube with a triumph monochromator, MoKα radiation λ=0.71073 Å (14 only). Absorption corrections were applied by SADABS. Structures were solved by direct methods and Fourier techniques and refined on $F^2$ using full matrix least-squares procedures. All non-H atoms were refined with anisotropic thermal parameters. All H atoms were refined in calculated positions in a rigid group model. The Flack parameter for non-centrosymmetrical structure of 14 is 0.00(15). The structures of 138 and 150 have two symmetrically independent molecules. One of terminal –i-Pr groups in 132 is disordered over two positions in ratio 42/58. X-ray diffraction from crystals of 138, 150 and 26 at high angles were very weak; even with a strong Incoatec IµS Cu source we could collected data only up to $2\theta_{max}$=114.98°, 120.0° and 132.0°, respectively. Calculations were performed by the Bruker SHELXTL (v. 6.10) package.

Cyclic Voltammetry.

Electrochemical experiments were conducted in a traditional 3-electrode geometry using a Solartron 1287 potentiostat. Electrolyte solutions (0.1 M) were prepared from HPLC-grade $CH_2Cl_2$ and anhydrous $Bu_4NBF_4$, and the solutions were freeze-pump-thaw degassed (3×) prior to analysis. Cyclic voltammetry was conducted under a nitrogen atmosphere. The working electrode was a glassy carbon electrode (3-mm diameter), with a Pt-coil counter electrode and Ag wire pseudo reference. The ferrocene/ferrocenium (Fc/Fc$^+$) couple was used as an internal standard following each experiment. Potential values were re-referenced to SCE using a value of 0.46 (V vs. SCE) for the Fc/Fc$^+$ couple in $CH_2Cl_2$. When necessary, potentials were re-referenced to NHE using SCE=−0.24 (V vs. NHE). LUMO and HOMO levels were approximated using SCE=−4.68 eV vs. vacuum. Cyclic voltammetry experiments were conducted at sweep rates of 50 (reported), 75, 100 and 125 mV s$^{-1}$. Particular scan rates show quasi-reversible kinetics with no alteration of peak splitting with scan rate. $E_{1/2}$ values were calculated assuming $E_{1/2} \approx E^{o\prime}=(E_{anodic}+E_{cathodic})/2$ based on these observations for reversible couples; for irreversible couples the $E^{o\prime}$ value is estimated as the potential at peak current. The $E_{a,c}$ peak splitting of the Fc/Fc$^+$ couple was similar to that of the analyte (~100 mV). The anodic peak current increases linearly with the square root of the scan rate in the range 50 to 125 mV s$^{-1}$, indicating a diffusion-controlled process. Analyte concentrations were ca. 1-5 mM.

Electronic Paramagnetic Resonance.

Figure 12:
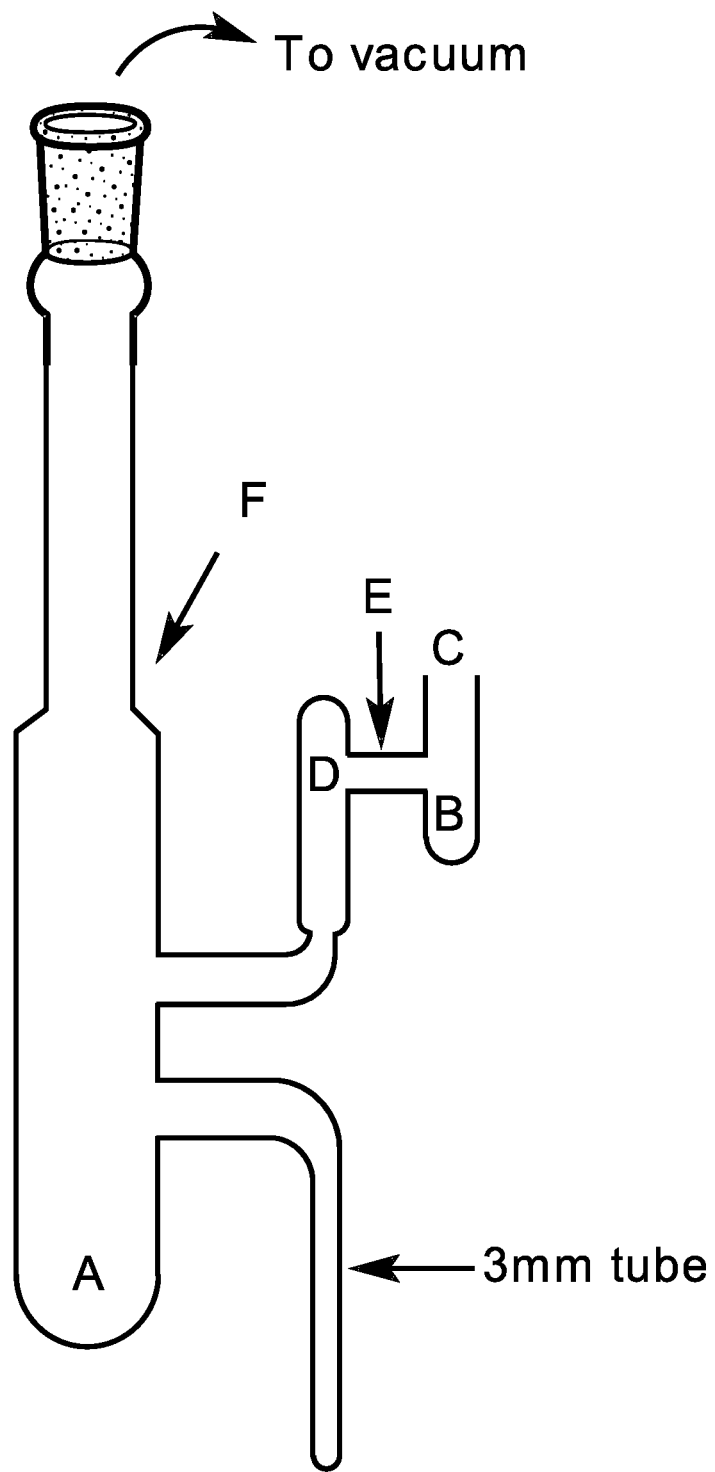
FIG. 12 is a front view of an apparatus used to generate anion radicals of exemplary compounds disclosed herein.

An apparatus (FIG. 12) was constructed from borosilicate glass and dried in a 100° C. oven. The apparatus was then cooled to room temperature under nitrogen and approximately 0.05 mg of the thieno-containing compounds was collected on a melting point capillary that was open on both ends and deposited at point A (FIG. 12). Potassium metal was added at point B and then opening C, as illustrated in FIG. 12, was sealed with an oxygen/natural gas torch. Vacuum was pulled (ca. 10$^{-6}$ torr) and K metal was sublimed with a Bunsen burner, resulting in a metal mirror inside D (FIG. 12). The apparatus was then sealed at point E (FIG. 12). Dry THF (approx. 1 mL) from a NaK still was directly distilled through the vacuum system to A (FIG. 12) and the apparatus was sealed at point F (FIG. 12). Controlled exposure to the potassium mirror resulted in formation of thieno-containing radical anion, from which the EPR spectra in FIGS. 10A-10C were obtained. The EPR spectra were collected on a Bruker EMX-080 spectrometer.

EPR Computational Details.

To determine the hyperfine coupling constants for the hydrogen and silicon nuclei coupled with the anion radical, the EPR spectra were simulated with the EasySpin package utilizing MATLAB code. DFT calculations were performed for the gas phase molecules using Gaussian09 Revision C.01 and the results were used to assign the HFCC and carbon spin density locations (Table 6). These computations were carried out at the UB3W91/6-311++G(2df,2pd)//UCAM-B3LYP/6-31++G(d,p) level of theory.

Geometry Calculations.

DFT calculations were performed for gas phase molecules using the Gaussian09 Revision C.01. Harmonic frequency analyses, performed at the same level of theory as the minimization, were used to confirm minimized structures.

Compounds.

Exemplary compound embodiments and methods of making such compounds are disclosed below.

In some embodiments, the compounds were made using the following steps. First, a Suzuki-Miyaura cross-coupling of 3,4-dibromothiophene and commercially available 2-ethoxycarbonylbenzeneboronic acid was performed (Schemes 9-11). In some embodiments, using Buchwald's SPhos ligand can facilitate efficient coupling of the electron-rich bromothiophene with the electron-poor arylboronic acid.

Next, saponification of diester 12, followed by formation of the acid chloride and Friedel-Crafts acylation provided dione 14 in good yield (Scheme 9). It was determined that 3,4-dibromothiophene could be mono-acylated to give 20 in 92% yield (Scheme 10).

Condensation with ethyl thioglycolate in the presence of potassium carbonate furnished thienothiophene 22 in 80% yield (Scheme 10). This method can be used to avoid preparing unsubstituted thieno[3,2-b]thiophene either through traditional methods known in the art, or the Matzger route disclosed by J. T. Henssler and A. J. Matzger, Org. Lett., 2009, 11, 3144-3147, the relevant portion of which is incorporated herein by reference. Suzuki-Miyaura cross-coupling provided diester 24 in quantitative yield (Scheme 10).

Compound 26 was made using the conditions described in Scheme 10, resulting in 79% yield over four steps. As illustrated in Scheme 11, dione 34 was prepared in an analogous manner via diester 32 starting from 3,5-dibromo-dithieno[3,2-b:20,30-d]thiophene (Scheme 11).

In some embodiments, the synthesis of diones 14, 26 and 34 can be performed on multi-gram scale with no silica gel chromatography. Nucleophilic addition of (trialkylsilyl)ethynyllithium proceeded quantitatively despite poor solubility of the dione starting materials in some embodiments.

Reduction of the respective diols by anhydrous $SnCl_2$ in toluene provided compounds 100, 150, 138, and 132 in modest to very good yield. Interestingly, in some embodiments, the reduction to 132 is complete within minutes while the reduction to 100 and 150 can require several hours to reach full conversion. The final compounds were stable toward silica gel and ambient conditions. No measures to protect the compounds from air or water were taken and no significant decomposition was observed in solution or in the solid-state.

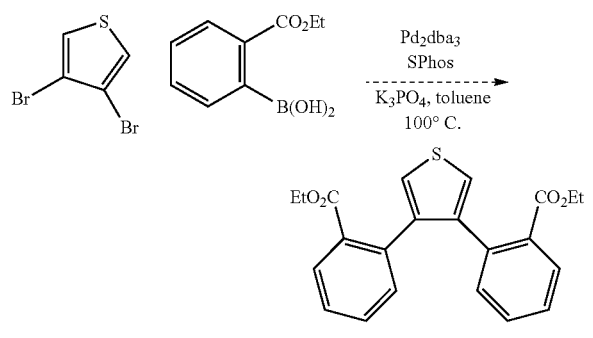

Diethyl 2,2'-(thiophene-3,4-diyl)dibenzoate (12)

In a dry glass pressure vessel, 2-ethoxycarbonyl-benzeneboronic acid (6.0 g, 31 mmol), $Pd_2dba_3$ (120 mg, 0.124 mmol), SPhos (100 mg, 0.248 mmol), anhydrous $K_3PO_4$ (10.5 g, 49.6 mmol) and toluene (35 mL) were combined. The mixture was sparged with nitrogen (10 min) then 3,4-dibromothiophene (3.0 g, 12.4 mmol) was added via syringe. The vessel was sealed and heated at 100° C. for 16 hours. Upon cooling to room temperature, the reaction was diluted with $CH_2Cl_2$ then filtered. The organics were washed with brine then dried over $MgSO_4$. Volatiles were removed under reduced pressure to give an orange oil in quantitative yield. This material can be used directly or purified by silica gel chromatography (20% EtOAc/hexanes) (v/v). $^1H$ NMR (500 MHz, $CDCl_3$) δ 7.70 (dd, J=7.7, 1.5 Hz, 2H), 7.35 (td, J=7.5, 1.5 Hz, 2H), 7.30 (td, J=7.6, 1.5 Hz, 2H), 7.26 (dd, J=7.5, 1.4 Hz, 2H), 7.20 (s, 2H), 4.08 (q, J=7.2 Hz, 4H), 1.12 (t, J=7.1 Hz, 6H); $^{13}C$ NMR (126 MHz, $CDCl_3$) δ 167.92, 141.38, 136.60, 131.98, 131.74, 130.87, 129.40, 127.11, 122.62, 60.84, 13.84. HRMS (ES+) calcd for $C_{22}H_{21}O_4S$ $(M+H)^+$ 381.1161. found 381.1168.

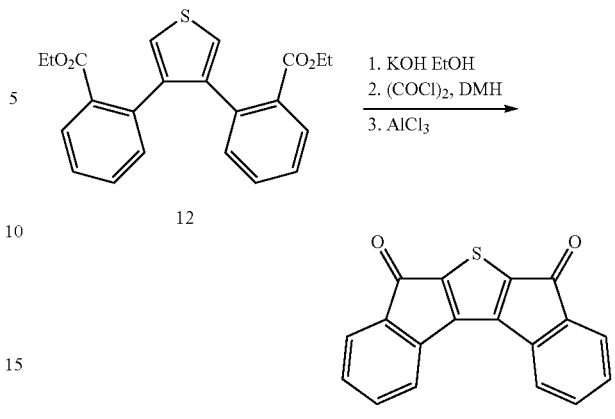

Diindeno[2,1-b:1',2'-d]thiophene-5,7-dione (14)

To a solution of the crude diester 12 (4.4 g) in ethanol (100 mL) was added aqueous KOH (115 mmol, 5 M). The reaction was heated at reflux for 16 hours then cooled to room temperature. The volume was reduced in vacuo (30 mL) and acidified with conc. HCl. The diacid was collected, washed with water and dried. To a suspension of the diacid in $CH_2Cl_2$ (100 mL) was added 5 drops DMF. Oxalyl chloride (4.0 mL, 46 mmol) was added dropwise via syringe. The reaction was stirred at room temperature for 3 hours then the volatiles were removed in vacuo. $CH_2Cl_2$ (100 mL) was added and the flask was cooled to 0° C. $AlCl_3$ (9.25 g, 69 mmol) was added and the reaction was stirred at 0° C. for 16 hours. The dark solution was poured onto ice and the precipitate was collected by filtration then washed with water. Recrystallization from $CHCl_3$ (1.5 L) provided the title compound as orange needles (1.71 g, 46% from 3,4-dibromothiophene). $^1H$ NMR (600 MHz, $CDCl_3$) δ 7.64 (d, J=7.2 Hz, 2H), 7.54 (t, J=7.5 Hz, 2H), 7.46 (d, J=7.3 Hz, 2H), 7.34 (t, J=7.5 Hz, 2H); limited solubility of the title compound hindered acquisition of $^{13}C$ NMR spectra; UV-Vis $(CHCl_3)\lambda_{max}$: 313, 440 (br) nm; HRMS (EI+) calcd for $C_{18}H_8O_2S$ $(M^+)$ 289.0245. found 288.0240.

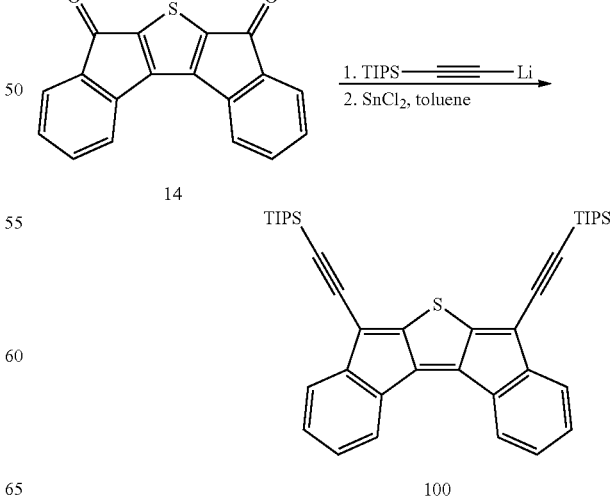

Compound 100

In a dry two-neck flask, (triisopropylsilyl)acetylene (0.8 mL, 3.45 mmol) was added to THF (5 mL) and cooled to 0° C. A solution of n-butyllithium (3.1 mmol, 1.6 M) was added dropwise then stirred for 5 minutes. In a second flask, dione 14 (200 mg, 0.69 mmol) was suspended in THF (25 mL) at 0° C. The (triisopropylsilyl)ethynyllithium solution was transferred via syringe to the dione suspension and stirred for 30 minutes. The reaction was quenched with saturated NH$_4$Cl solution (50 mL). The organics were extracted with EtOAc (2×50 mL), washed with brine and dried over MgSO$_4$. The volatiles were removed under reduced pressure, then the crude material was passed through a short plug of silica, eluting first with hexanes then EtOAc. The polar fractions were combined and reduced in vacuo. Toluene (15 mL) was added and the solution was degassed thoroughly under dynamic vacuum. Finely ground SnCl$_2$ (400 mg, 10.4 mmol) was added then further degassed under dynamic vacuum. The slurry was stirred for 3 hours at room temperature, then poured onto a plug of silica and eluted with 1:1 CH$_2$Cl$_2$/hexanes. Removal of the volatiles under reduced pressure provided the title compound (270 mg, 63%) as a green solid. $^1$H NMR (500 MHz, CDCl$_3$) δ 7.51 (d, J=7.3 Hz, 2H), 7.20 (td, J=7.5, 1.0 Hz, 2H), 7.13 (d, J=7.3 Hz, 2H), 7.07 (td, J=7.5, 1.2 Hz, 2H), 1.17 (s, 42H); $^{13}$C NMR (126 MHz, CDCl$_3$) δ 153.77, 148.89, 144.03, 130.77, 130.19, 125.78, 124.37, 120.68, 116.32, 105.90, 99.70, 18.73, 11.28; UV-Vis (CH$_2$Cl$_2$) $\lambda_{max}$ (ε): 266 (36000), 303 (30000), 311 (30300), 416 (31600), 443 (38400), 655 (br, 6400), 765 (sh, 6000) nm; HRMS (ES+) calcd for C$_{40}$H$_{51}$SSi$_2$ (M+H)$^+$ 619.3250. found 619.3243.

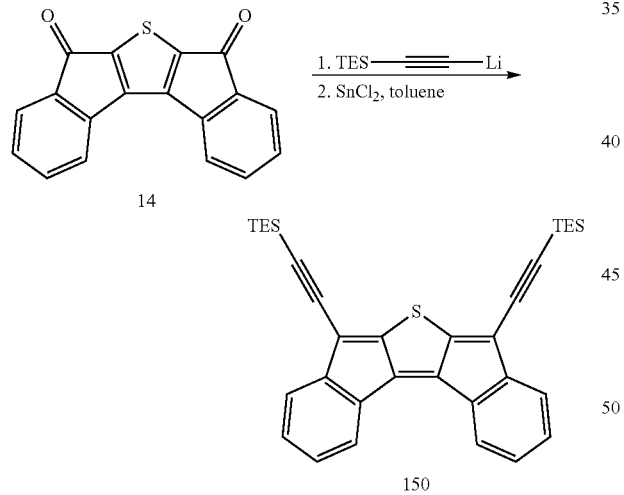

Compound 150

The procedure for 150 was adapted with (triethylsilyl)acetylene (521 mg, 3.71 mmol), n-butyllithium (3.34 mmol, 1.6 M) and 14 (214 mg, 0.74 mmol) to provide the title compound (147 mg, 37%) as a green solid. $^1$H NMR (500 MHz, CDCl$_3$) δ 7.47 (d, J=7.3 Hz, 2H), 7.19 (td, J=7.5, 1.0 Hz, 2H), 7.11 (d, J=7.4 Hz, 2H), 7.06 (td, J=7.5, 1.1 Hz, 2H), 1.14 (t, J=7.9 Hz, 18H), 0.77 (q, J=7.9 Hz, 12H); $^{13}$C NMR (126 MHz, CDCl$_3$) δ 153.79, 148.73, 144.01, 130.66, 130.11, 125.80, 124.35, 120.62, 116.17, 106.53, 99.06, 7.63, 4.48; HRMS (ES+) calcd for C$_{34}$H$_{38}$SSi$_2$ (M$^+$) 534.2233. found 534.2208.

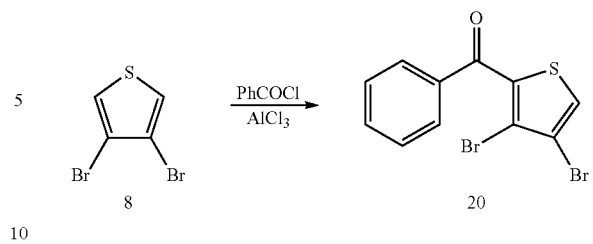

2-Benzoyl-3,4-dibromothiophene (20)

AlCl$_3$ (15 g, 125 mmol) was added in three portions to a stirred solution of 3,4-dibromothiophene (10.0 g, 41.3 mmol) and benzoyl chloride (8.7 g, 62 mmol) in CH$_2$Cl$_2$ (100 mL) at 0° C. The cooling bath was removed and the reaction was stirred for 16 hours. The dark solution was poured onto ice, diluted with CH$_2$Cl$_2$ (100 mL) and washed successively with aqueous NaOH (1 M) and brine. The organic phases were combined and dried over MgSO$_4$. Removal of volatiles by reduced pressure provided the title compound (13.13 g, 92%) as a yellow solid. $^1$H NMR (500 MHz, CDCl$_3$) δ 7.88-7.84 (m, 2H), 7.67 (s, 1H), 7.67-7.63 (m, 1H), 7.52 (dd, J=8.5, 7.1 Hz, 2H); $^{13}$C NMR (126 MHz, CDCl$_3$) δ 187.38, 136.87, 136.82, 133.42, 129.86, 128.56, 128.08, 118.19, 116.67; HRMS (ES+) calcd for C$_{11}$H$_6$SBr$_2$ (M+), 343.8506. found 343.8521.

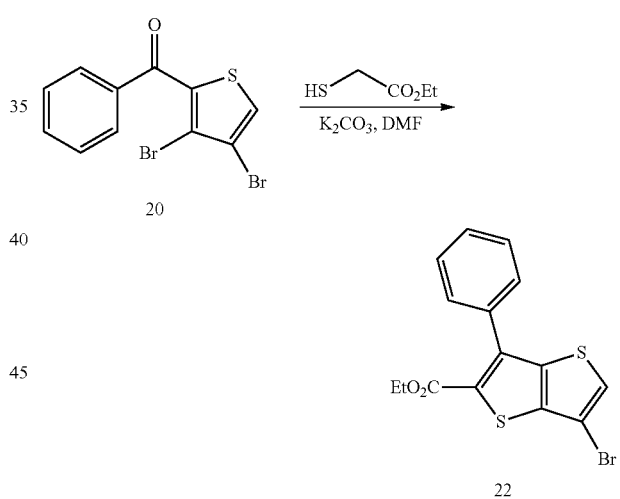

Ethyl 6-bromo-3-phenylthieno[3,2-b]thiophene-2-carboxylate (22)

To a solution of 20 (13.13 g, 37.9 mmol) in DMF (50 mL) was added K$_2$CO$_3$ (15.7 g, 113.8 mmol) and the reaction was rigorously degassed under dynamic vacuum. With stirring, ethyl thioglycolate (4.79 g, 39.8 mmol) was added dropwise via syringe and then the reaction was heated at 60° C. for 1 day. After cooling, the mixture was poured into water (100 mL). The solids were collected and washed with water. Recrystallization from ethanol (500 mL) provided 22 (11.2 g, 80%) as tan needles. $^1$H NMR (500 MHz, CDCl$_3$) δ 7.60-7.55 (m, 2H), 7.53-7.45 (m, 4H), 4.30 (q, J=7.1 Hz, 2H), 1.29 (t, J=7.1, 3H); $^{13}$C NMR (126 MHz, CDCl$_3$) δ 162.08, 141.75, 141.14, 140.77, 133.72, 129.21, 129.05, 128.82, 128.30, 128.17, 103.14, 61.36, 14.08; HRMS (ES+) calcd for $C_{15}H_2S_2O_2Br$ (M+H)+366.9462. found 366.9454.

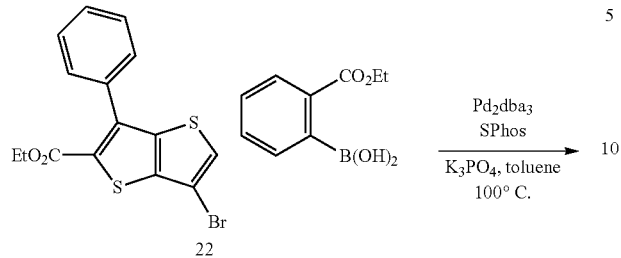

Diester 24

In a dry glass pressure vessel, 2-ethoxycarbonylbenzeneboronic acid (581 mg, 2.99 mmol), Pd$_2$dba$_3$ (25 mg, 0.027 mmol), SPhos (22 mg, 0.054 mmol), anhydrous K$_3$PO$_4$ (1.15 g, 5.44 mmol), 22 (1.00 g, 2.72 mmol) and toluene (10 mL) were combined. The mixture was sparged with nitrogen (10 minutes). The vessel was sealed and brought to 100° C. for 16 hours. Upon cooling to room temperature the reaction was diluted with CH$_2$Cl$_2$ then filtered. The organics were washed with brine and dried over MgSO$_4$. Removal of volatiles under reduced pressure provides the title compound in quantitative yield. This material can be used directly or purified by silica gel chromatography (20% EtOAc/hexanes) (v/v) to give a yellow solid. $^1$H NMR (500 MHz, CDCl$_3$) 8.01 (dd, J=7.8, 1.4 Hz, 1H), 7.66-7.63 (m, 2H), 7.61 (dd, J=7.4, 1.4 Hz, 1H), 7.57 (dd, J=7.6, 1.5 Hz, 1H), 7.55-7.47 (m, 4H), 7.45 (s, 1H), 4.26 (q, J=7.1 Hz, 2H), 4.18 (q, J=7.1 Hz, 2H), 1.25 (t, J=7.1 Hz, 3H), 1.06 (t, J=7.1 Hz, 3H); $^{13}$C NMR (126 MHz, CDCl$_3$) δ 167.58, 162.35, 141.73, 141.01, 140.94, 134.82, 134.78, 134.28, 131.91, 131.07, 130.61, 130.55, 129.17, 128.61, 128.44, 128.21, 127.88, 127.84, 61.23, 61.09, 14.10, 13.71; HRMS (ES+) calcd for $C_{24}H_{21}S_2O_4$ (M+H)$^+$437.0881. found 437.0875.

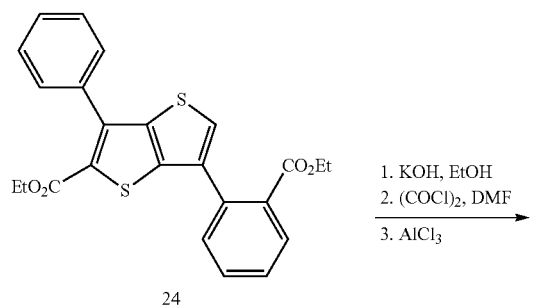

Indeno[2,1-b]indeno[1',2':4,5]thieno[2,3-d]thiophene-6,12-dione (26)

To a solution of 24 (0.98 g, 2.25 mmol) in ethanol (100 mL) was added aqueous KOH (12 mmol, 1.5 M). The reaction was heated at reflux for 16 hours then cooled to room temperature. The volume was reduced in vacuo (to 20 mL) and acidified with concentrated HCl. The diacid was collected, washed with water and dried. To a suspension of the diacid in CH$_2$Cl$_2$ (100 mL) was added DMF (5 drops). Oxalyl chloride (1.0 mL, 11.2 mmol) was added dropwise via syringe. The reaction was stirred at room temperature for 3 hours then the volatiles were removed in vacuo. CH$_2$Cl$_2$ (50 mL) was added and the flask was cooled to 0° C. AlCl$_3$ (3.0 g, 22.3 mmol) was added as a solid. The reaction was allowed to warm to room temperature and stir for 16 hours. The dark solution was poured onto ice and the precipitate was collected by filtration. Successive washes with water and acetone gave the title compound (630 mg, 79%) as a magenta solid. Limited solubility hindered acquisition of NMR spectra; UV-Vis (CHCl$_3$) λ$_{max}$: 370, 490, 522 (sh) nm; HRMS (EI+) calcd for $C_{20}H_8O_2S_2$(M$^+$) 343.9966. found 343.9959.

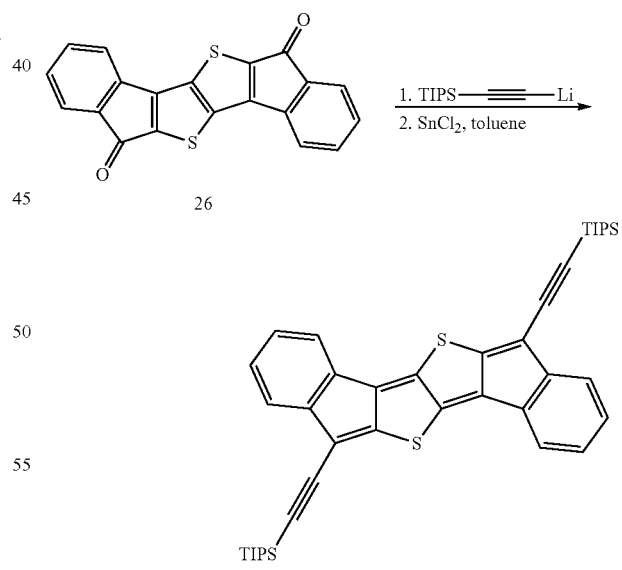

Compound 138

To a solution of (triisopropylsilyl)acetylene (527 mg, 2.9 mmol) in THF (5 mL) at 0° C. was added n-butyllithium (2.6 mmol, 1.6 M in hexanes) dropwise. In a separate flask, 26 (200 mg, 0.58 mmol) was suspended in THF (25 mL) at 0° C. The (triisopropylsilyl)ethynyllithium solution was transferred to the dione suspension via syringe then sonicated for 10 minutes. After quenching with a saturated NH$_4$Cl solution, the organics were extracted with Et$_2$O and dried over MgSO$_4$. The volume was reduced in vacuo and passed through a short plug of silica, eluting with EtOAc. Volatiles were removed under reduced pressure. Toluene (15 mL) was added and the flask was rigorously degassed under dynamic vacuum. Finely ground SnCl$_2$ (250 mg, 1.25 mmol) was added and the reaction was stirred for 3 hours. The mixture was passed through a plug of silica (CH$_2$Cl$_2$/hexanes). Evaporation of the volatiles provided the title compound (260 mg, 66%) as a dark blue solid. $^1$H NMR (500 MHz, CDCl$_3$) δ 7.36 (d, J=7.3 Hz, 2H), 7.28-7.24 (m, 2H), 7.22 (dd, J=7.5, 1.1 Hz, 2H), 7.12 (td, J=7.3, 1.4 Hz, 2H), 1.21 (s, 42H); $^{13}$C NMR (126 MHz, CDCl$_3$) δ 150.07, 147.30, 146.98, 139.43, 129.62, 128.82, 125.51, 122.65, 120.76, 114.77, 105.47, 99.95, 18.76, 11.30; UV-Vis (CH$_2$Cl$_2$) λ$_{max}$ (ε): 267 (22100), 444 (13100), 477 (11800), 652 (br, 15100) nm; HRMS (ES+) calcd for C$_{42}$H$_{50}$S$_2$Si$_2$ (M$^+$) 674.2893. found 674.2892.

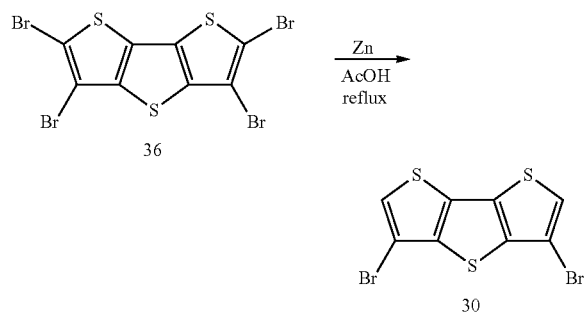

3,5-Dibromodithieno[3,2-b:2',3'-d]thiophene

In a 3-neck flask, tetrabromodithieno[3,2-b:2',3'-d]thiophene[1] (2.7 g, 5.3 mmol) in glacial AcOH (150 mL) was brought to reflux. Zn powder (3.44 g, 53 mmol) was added to the suspension. The reaction was refluxed for a further 30 min and then hot filtered through a fritted funnel. The solution was allowed to cool to room temperature, then the crude product was precipitated by the addition of water. The solids were collected by filtration. Recrystallization from chloroform provided the title compound as colorless needles (450 mg, 24%). $^1$H NMR (500 MHz, CDCl$_3$/CS$_2$) δ 7.31 (s); $^{13}$C NMR (126 MHz, CDCl$_3$/CS$_2$) δ 142.74, 130.84, 123.16, 103.90.

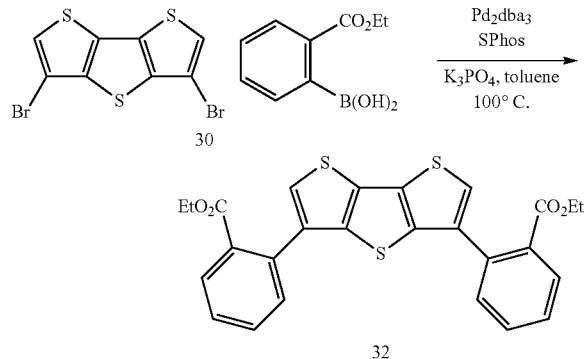

Diester 14

In a dry glass pressure vessel, 3,5-dibromodithieno[3,2-b:2',3'-d]thiophene (450 mg, 1.27 mmol), 2-ethoxycarbonyl-benzeneboronic acid (754 mg, 3.18 mmol), Pd$_2$dba$_3$ (12 mg, 0.013 mmol), SPhos (24 mg, 0.05 mmol), anhydrous K$_3$PO$_4$ (1.0 g, 5.1 mmol) and toluene (15 mL) were combined and sparged with nitrogen (10 min). The vessel was sealed and brought to 100° C. for 24 hours. Upon cooling to room temperature the reaction was diluted with CH$_2$Cl$_2$ then filtered. The organics were washed with brine and dried over MgSO$_4$. Removal of volatiles under reduced pressure provided the title compound in quantitative yield. This material can be used directly or purified by silica gel chromatography (20% EtOAc/hexanes) (v/v) to give a yellow solid. $^1$H NMR (500 MHz, CDCl$_3$) δ 7.94 (d, J=7.8 Hz, 2H), 7.58-7.54 (m, 4H), 7.50-7.42 (m, 2H), 7.23 (s, 2H), 4.12 (q, J=7.2 Hz, 4H), 1.01 (t, J=7.2 Hz, 6H); $^{13}$C NMR (126 MHz, CDCl$_3$) δ 167.76, 142.24, 135.53, 135.00, 131.73, 131.27, 130.42, 130.40, 130.18, 128.25, 122.45, 61.13, 13.75; HRMS (ES+) calcd for C$_{26}$H$_{21}$S$_3$O$_4$ (M+H)$^+$ 493.0602. found 493.0601.

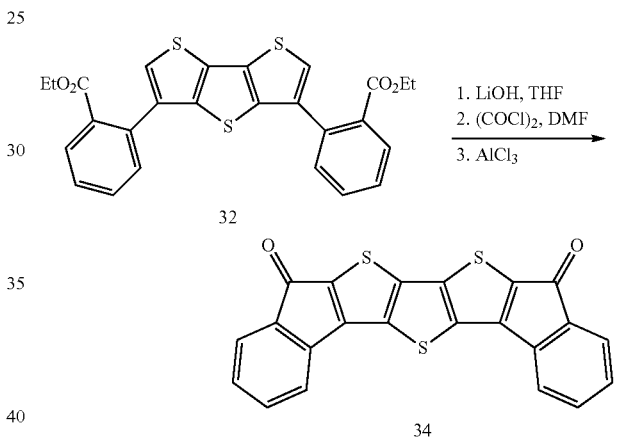

Diindenodithieno[3,2-b:2',3'-d]thiophene-3,13-dione (34)

To a solution of 32 (0.50 g, 2.25 mmol) in ethanol (100 mL) was added aqueous KOH (14.3 mmol, 1.4 M). The reaction was heated at reflux for 16 hours then cooled to room temperature. The volume was reduced in vacuo (to 15 mL) and acidified with conc. HCl. The diacid was collected, washed with water and dried. To a suspension of the diacid in CH$_2$Cl$_2$ (100 mL) was added DMF (5 drops). Oxalyl chloride (0.35 mL, 11.2 mmol) was added dropwise via syringe. The reaction was stirred at room temperature for 3 hours then the volatiles were removed in vacuo. CH$_2$Cl$_2$ (50 mL) was added and the flask was cooled to 0° C. AlCl$_3$ (1.0 g, 22.3 mmol) was added as a solid and the reaction was stirred for 1 hour. The dark solution was poured onto ice and the precipitate was collected by filtration. Successive washes with water and acetone gave the title compound (328 mg, 81%) as a red solid. Limited solubility hindered acquisition of NMR spectra; UV-Vis (CHCl$_3$) λ$_{max}$: 296, 481, 514 nm; HRMS (EI+) calcd for C$_{22}$H$_8$O$_2$S$_3$ (M$^+$) 399.9686. found 399.9700.

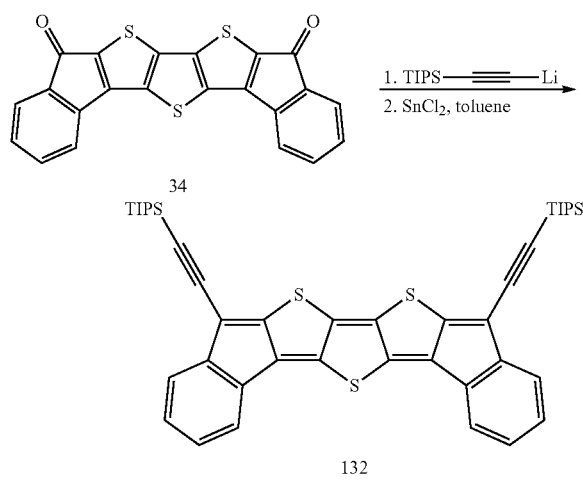

Compound 132

To a solution of (triisopropylsilyl)acetylene (227 mg, 1.25 mmol) in THF (5 mL) at 0° C. was added n-butyllithium (1.12 mmol, 1.5 M in hexanes) dropwise. In a separate flask, 34 (100 mg, 0.25 mmol) was suspended in THF (25 mL) and cooled to 0° C. The (triisopropylsilyl)ethynyllithium solution was transferred to the dione suspension via syringe then sonicated for 10 minutes. After quenching with a saturated NH$_4$Cl solution, the organics were extracted with Et$_2$O and dried over MgSO$_4$. The volume was reduced in vacuo and passed through a short plug of silica, eluting with EtOAc. Volatiles were removed under reduced pressure. Toluene (15 mL) was added and the flask was rigorously degassed under dynamic vacuum. Finely ground SnCl$_2$ (250 mg, 1.25 mmol) was added and the reaction was stirred for 10 minutes. The mixture was passed through a plug of silica (CH$_2$Cl$_2$/hexanes). Evaporation of the volatiles provided the title compound (131 mg, 72%) as a deep purple solid. $^1$H NMR (500 MHz, CDCl$_3$) δ 7.31 (d, J=7.3 Hz, 2H), 7.25 (d, J=7.4 Hz, 2H), 7.19 (t, J=7.5 Hz, 2H), 7.07 (t, J=7.5 Hz, 2H), 1.21 (s, 42H); $^{13}$C NMR (126 MHz, CDCl$_3$) δ 148.91, 146.56, 143.92, 142.96, 138.51, 129.20, 128.52, 125.08, 122.04, 120.72, 113.17, 105.36, 100.45, 18.78, 11.34; UV-Vis (CH$_2$Cl$_2$) λ$_{max}$ (ε): 256 (32300), 320 (8000), 513 (27600), 553 (39400), 683 (19600), 740 (sh, 16600) nm; HRMS (ES+) calcd for C$_{44}$H$_{51}$S$_3$Si$_2$ (M+H)$^+$ 731.2691. found 731.2711.

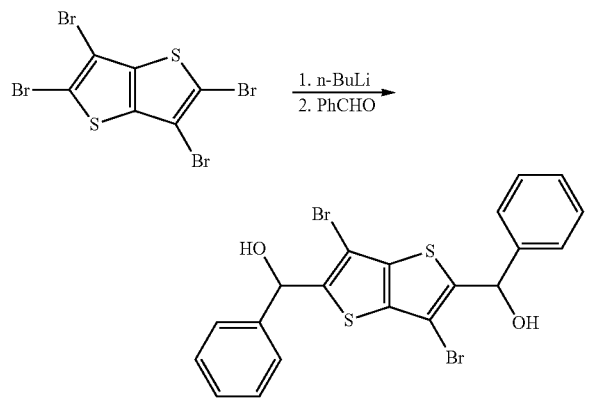

(3,6-dibromothieno[3,2-b]thiophene-2,5-diyl)bis (phenylmethanol)

To a suspension of tetrabromothieno[3,2-b]thiophene (4.56 g, 10 mmol) in THF (100 mL) at 0° C. was added n-butyllithium (11 mmol, 1.6M in hexanes) dropwise via addition funnel. The reaction was stirred for 30 minutes. Benzaldehyde (1.33 g, 12.5 mmol) was added quickly via syringe. The reaction was stirred for 30 minutes then poured into water (100 mL). The organics were extracted with diethyl ether, washed with brine and dried over MgSO$_4$. Volatiles were removed in vacuo to provide the title compound as a mixture of diastereomers (2.76 g, 54% yield).

$^1$H NMR (500 MHz, DMSO-d$_6$) δ 7.47-7.40 (m, 4H), 7.36 (m, 4H), 7.32-7.25 (m, 2H), 6.72 (m, 2H), 6.00 (m, 2H). $^{13}$C NMR (126 MHz, DMSO-d$_6$) δ 152.04, 151.98, 147.90, 147.84, 141.72, 141.69, 133.62, 133.59, 132.95, 132.91, 131.55, 131.53, 104.78, 104.74, 75.56, 75.54.

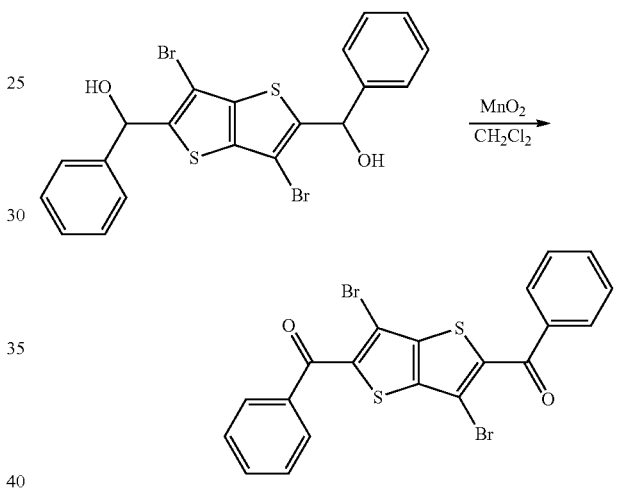

(3,6-dibromothieno[3,2-b]thiophene-2,5-diyl)bis (phenylmethanone)

The crude diol was suspended in CH$_2$Cl$_2$ (50 mL). Activated manganese(IV) oxide was added and the reaction was stirred for 2 days at room temperature under a nitrogen atmosphere. The slurry was passed through a pad of celite with CH$_2$Cl$_2$. Evaporation of volatile components provided the title compound in quantitative yield. $^1$H NMR (500 MHz, CDCl$_3$) δ 7.93-7.80 (m, 4H), 7.68-7.62 (m, 2H), 7.52 (d, J=8.5 Hz, 4H). $^{13}$C NMR (126 MHz, CDCl$_3$) δ 187.38, 136.82, 133.42, 129.86, 128.56, 128.08, 118.19, 116.67.

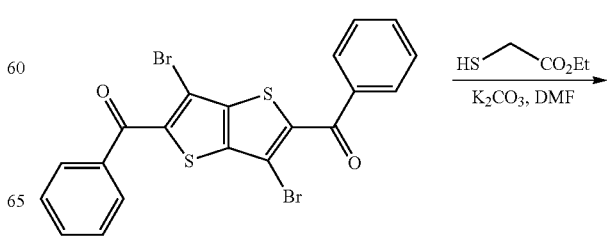

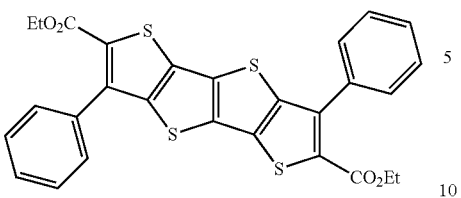

diethyl 3,7-diphenylthieno[2',3':4,5]thieno[3,2-b]thieno[2,3-d]thiophene-2,6-dicarboxylate The procedure for diester 14k was adapted. (3,6-dibromothieno[3,2-b]thiophene-2,5-diyl)bis(phenylmethanone) (1.28 g, 2.53 mmol), DMF (25 mL), ethyl thioglycolate (625 mg, 5.18 mmol), potassium carbonate (2.0 g, 15 mmol) provided the title compound as yellow solids (840 mg, 61%). $^1$H NMR (500 MHz, CDCl$_3$) δ 7.66-7.60 (m, 4H), 7.57-7.47 (m, 6H), 4.30 (q, J=7.1 Hz, 4H), 1.28 (t, J=7.1 Hz, 6H). $^{13}$C NMR (126 MHz, CDCl$_3$) δ 161.94, 144.26, 141.74, 135.19, 133.70, 133.67, 129.06, 128.93, 128.36, 128.13, 61.36, 14.09.

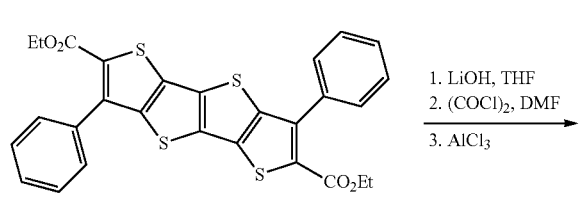

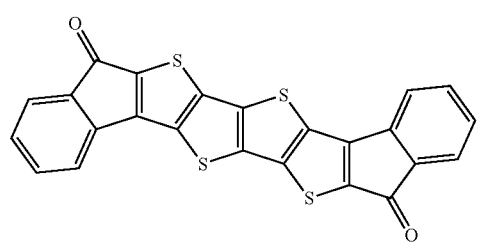

The title compound was prepared analogously to same 3 steps as dione 34.

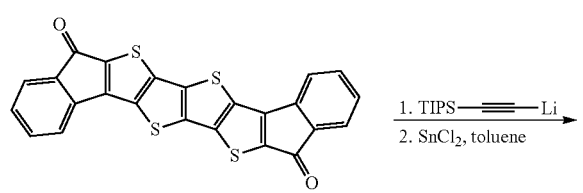

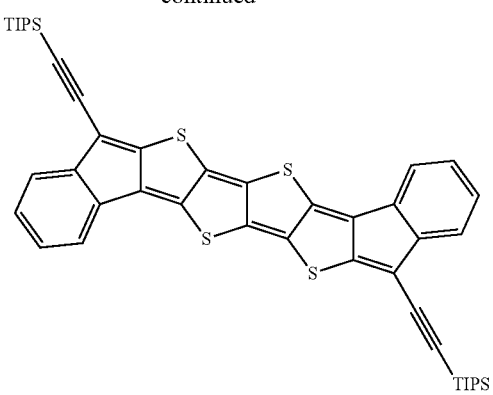

Compound 136. This compound was made using steps similar to those described above for making Compound 132.

Figure 4A:
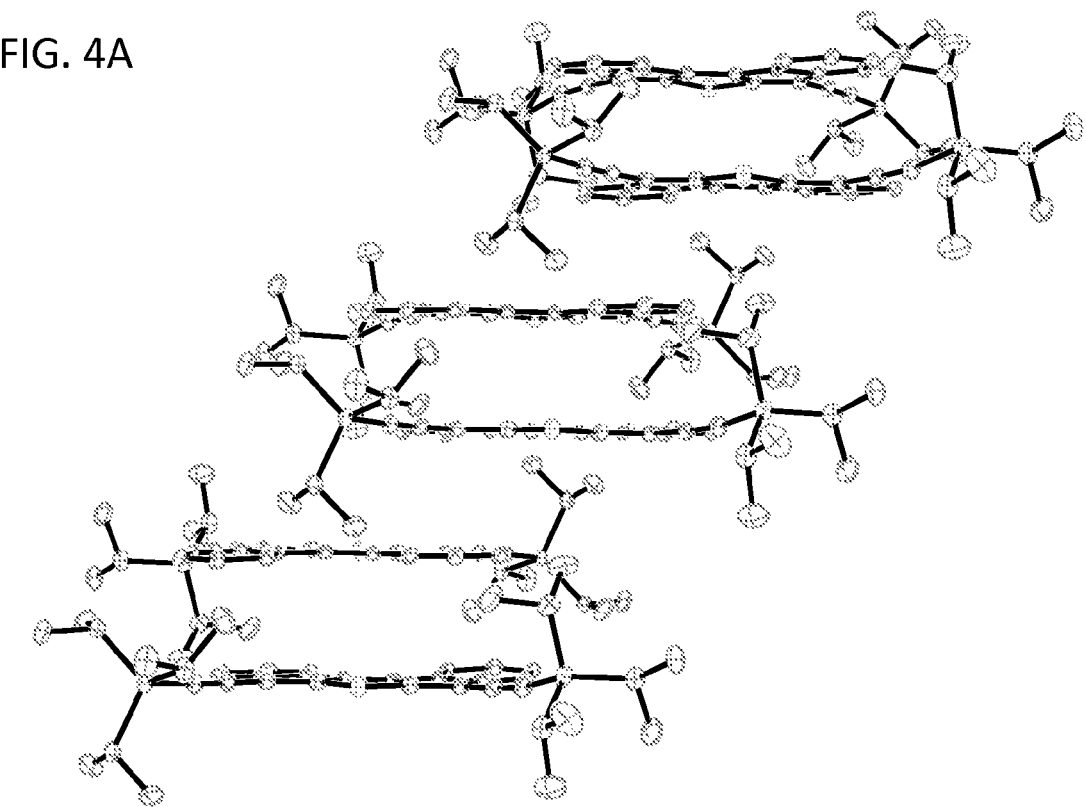
FIGS. 4A-4F are images illustrating the solid-state packing of exemplary compound embodiments.
Figure 4B:
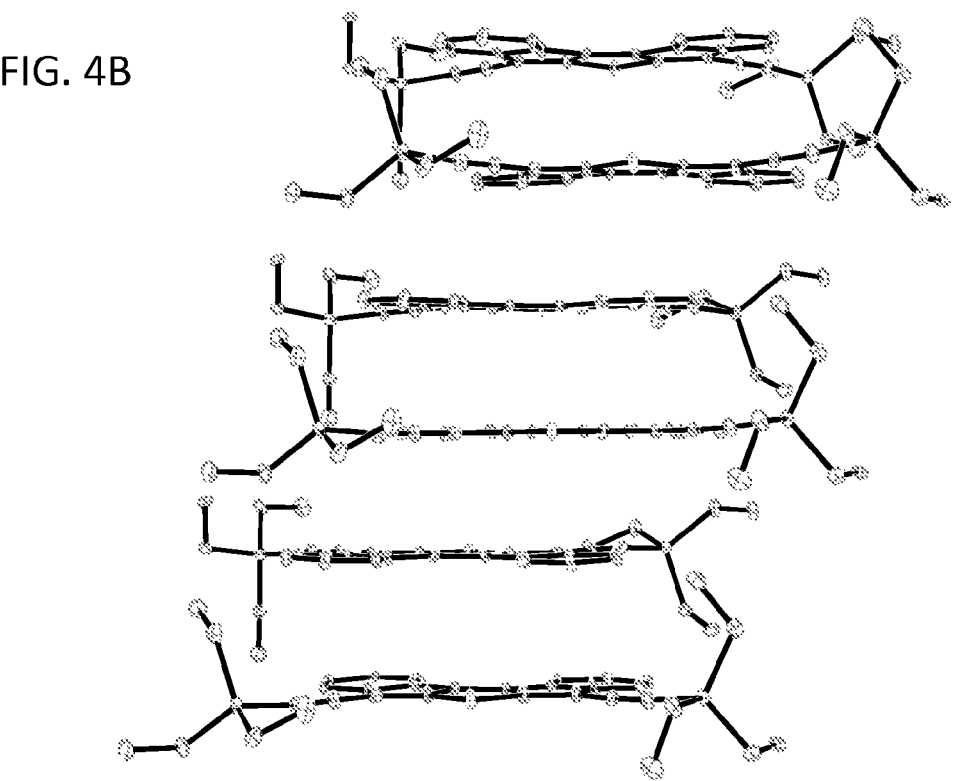
Figure 4C:
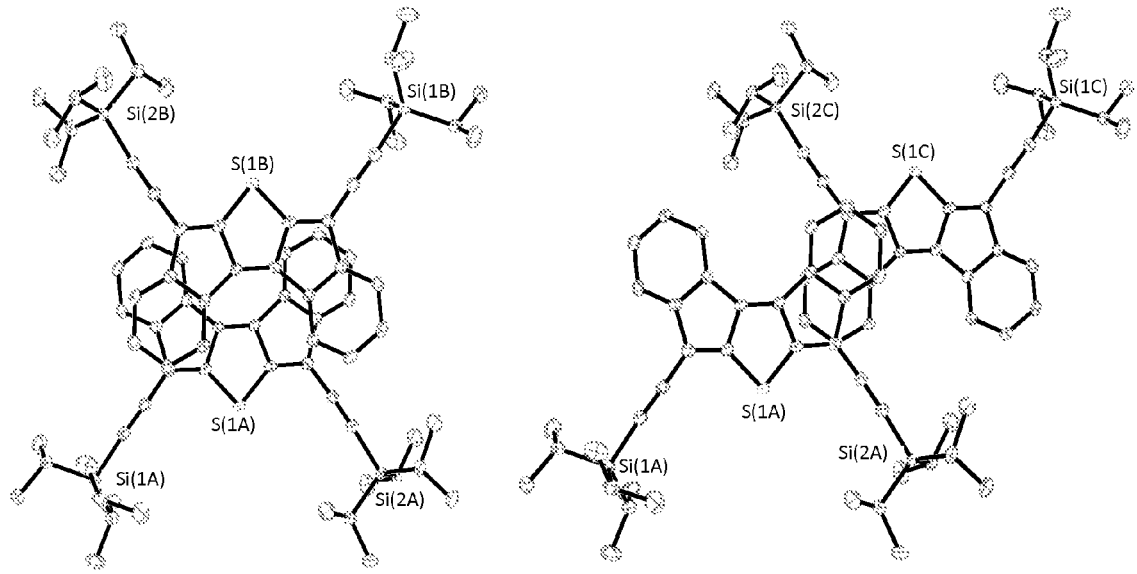
Figure 4D:
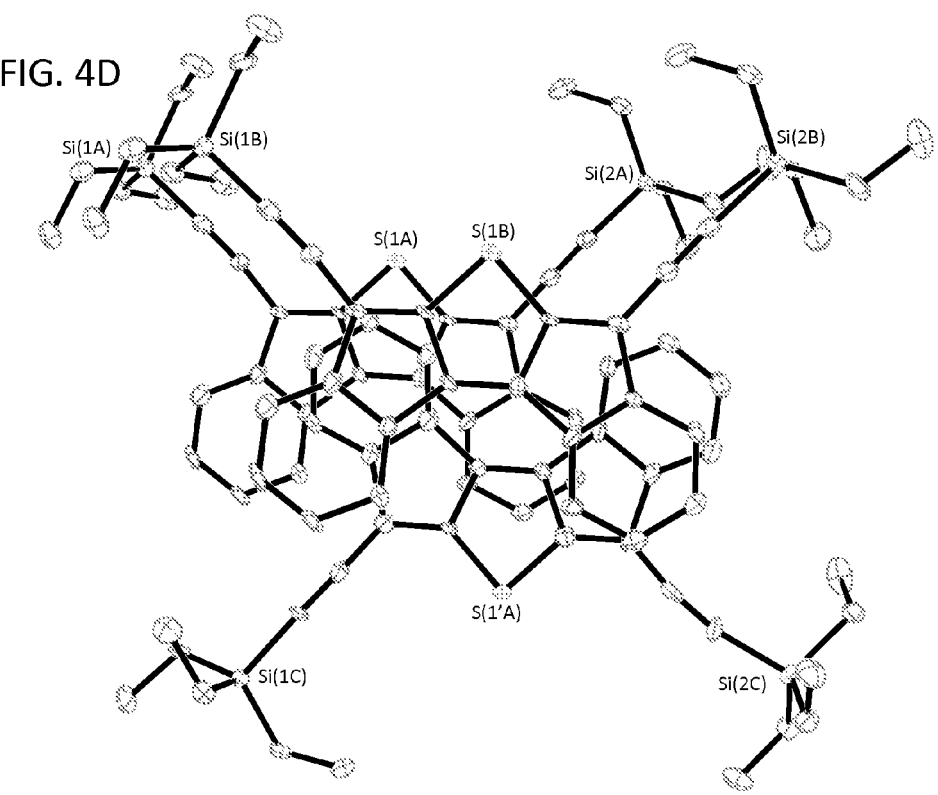
Figure 4E:
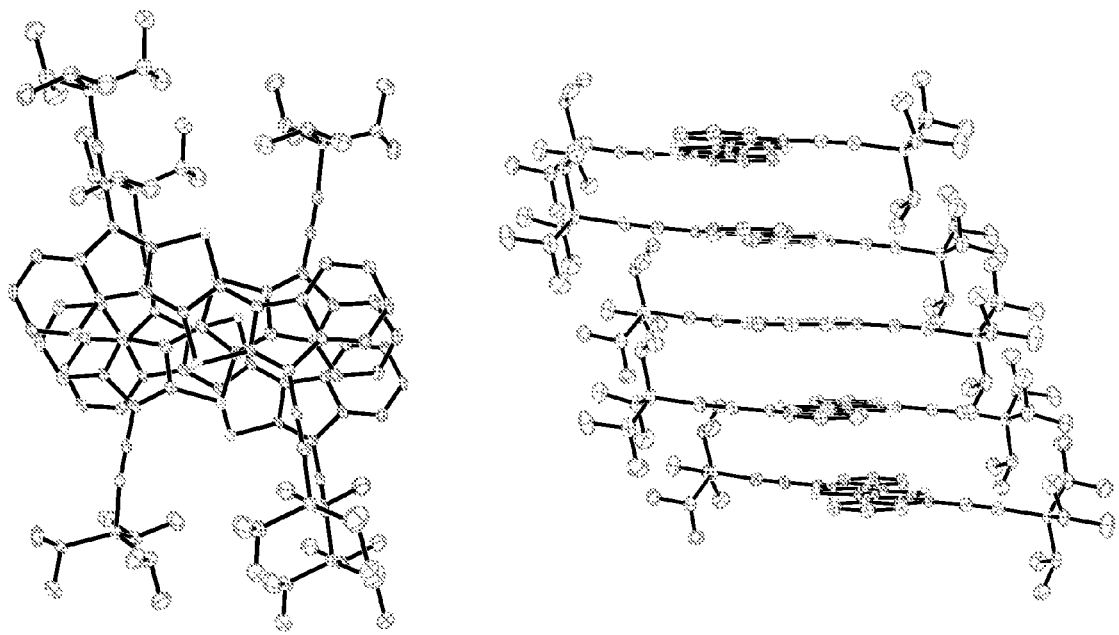
Figure 4F:
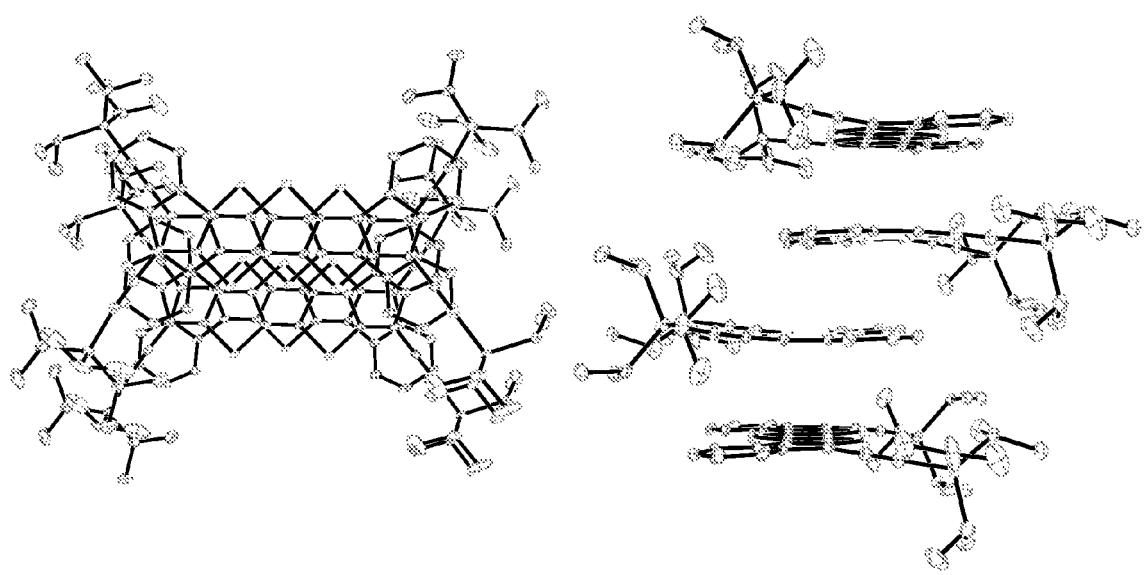

Single crystals of particular compounds disclosed herein sufficient for characterization by X-ray diffraction were obtained by slow evaporation from CH$_2$Cl$_2$. Compound 100 arranges into a pairwise slipped stacks with distances between average planes of 3.30 Å within the pair and 3.37 Å between adjacent pairs (FIG. 4A). Lateral (short-axis) slip of the core was found to be 1.06 Å in the pair and 5.82 Å between pairs. Compound 150 also packs in pairwise slipped stacks with the distance between average planes of the molecules of 3.43 Å in the pair and 3.34 Å between pairs (FIG. 4B). The smaller trialkylsilyl group altered the lateral slip to 2.52 Å in the pair and 2.55 Å between pairs. Additional stacking images of Compounds 100 and 150 also are illustrated in FIGS. 4C and 4D. Compound 138 forms an alternating 1D structure rather than the dimers seen with 100 due to its centrosymmetry (FIG. 4E). The distance between the average planes is 3.41 Å with a lateral slip of 1.46 Å between cores of the molecules. Spacing between neighboring 1D stacks was greater than van der Waals distance. 132 shows strong overlapping of the quinoidal cores with interplanar distance of 3.46° A and lateral slip of 1.79 Å and 1.23 Å (FIG. 4F). The 1D columns are essentially insulated from adjacent columns by the (triisopropylsilyl)ethynyl groups.

Table 1 summarizes the bond distances in the core of particular compound embodiments disclosed herein.

TABLE 1

Solid-state packing and bond distances in the quinoidal core[a]

|  | DI1T-TIPSE | DI1T-TESE | DI2T | DI3T |
|---|---|---|---|---|
| Interplanar distance[b] | 3.30, 3.37 | 3.43, 3.34 | 3.41 | 3.46 |
| Lateral slip[b] | 1.06, 5.82 | 2.52, 2.55 | 1.46 | 1.23, 1.79 |
| RMS deviation from planarity[b] | 0.042 | 0.026 | 0.013 | 0.026 |
| C(1)-C(2) | 1.365(3) [1.357] | 1.364 (12)[c] | 1.373(5) [1.360] | 1.368(4)[c] [1.361] |
| C(2)-C(3) | 1.454(2)[c] [1.456] | 1.454 (12)[c] | 1.447(5) [1.456] | 1.439(4)[c] [1.455] |
| C(3)-C(3a/4) | 1.359(3) [1.353] | 1.358 (11)[c] | 1.366(5) [1.351] | 1.367(4)[c] [1.352] |
| C(4)-C(4a/5) | — | — | 1.440(7) [1.461] | 1.437(4)[c] [1.454] |

TABLE 1-continued

Solid-state packing and bond distances in the quinoidal core[a]

|   | DI1T-TIPSE | DI1T-TESE | DI2T | DI3T |
|---|---|---|---|---|
| C(5)-C(5a) | — | — | — | 1.366(4)[c] [1.352] |

[a]All distances in Å; atom numbering is shown below; calculated (UCAM-B3LYP/6-31G (d, p)) bond lengths in brackets.
[b]Values determined omitting the (trialkylsilyl)ethynyl groups.
[c]Average value due to asymmetry in the solved crystal structure or crystallographically independent molecules

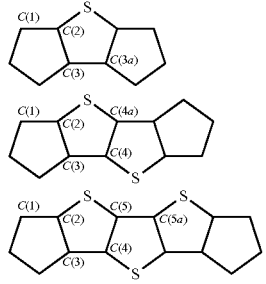

Figure 5A:
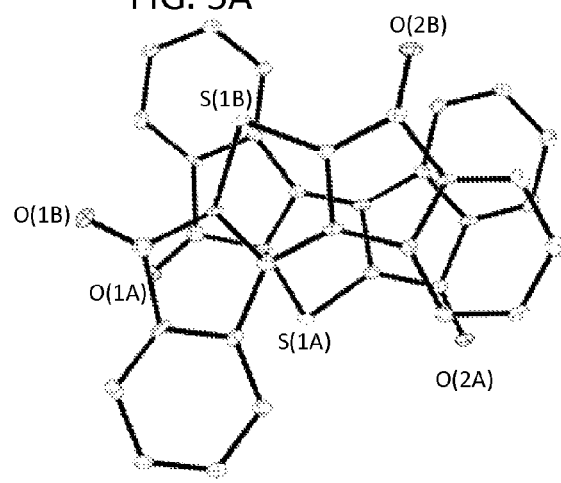
FIGS. 5A and 5B are images illustrating the solid-state packing of exemplary dione precursors disclosed herein.
Figure 5B:
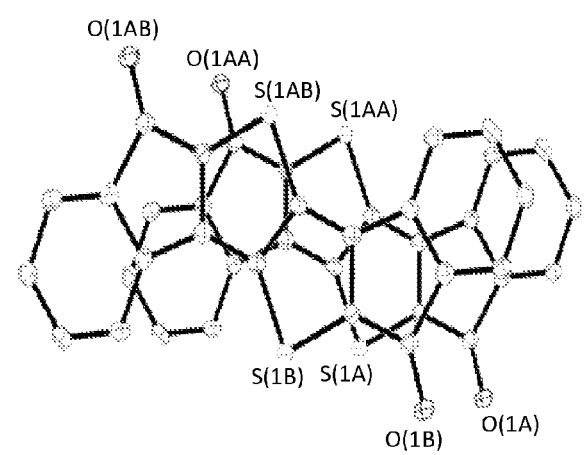
Figure 6A:
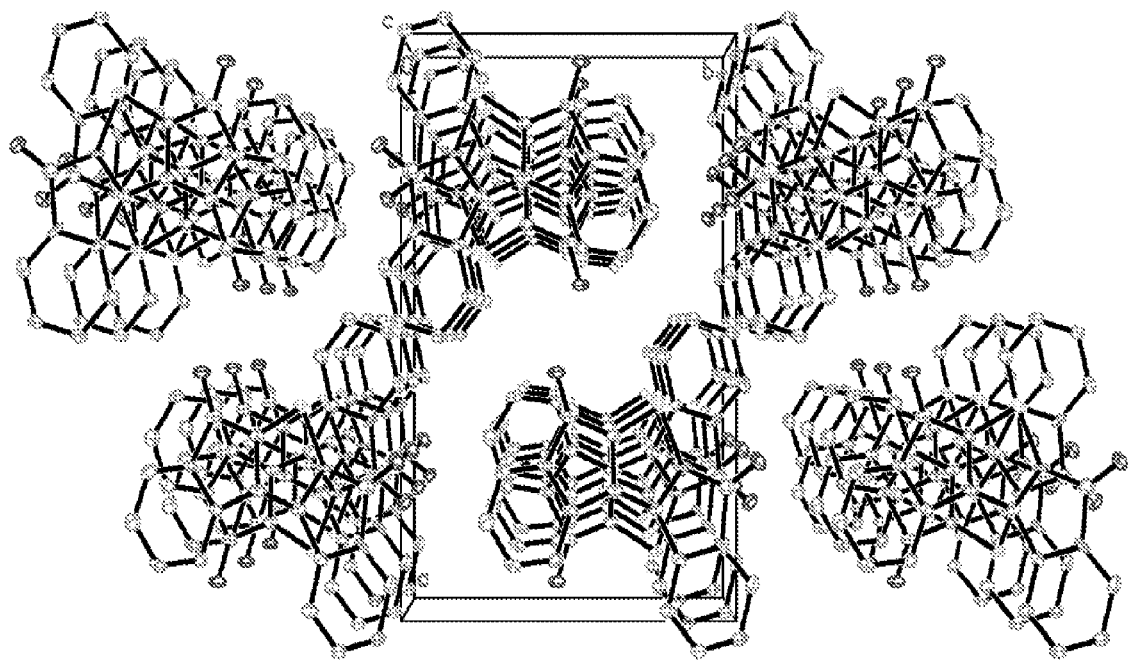
FIGS. 6A and 6B are expanded packing views of exemplary dione precursors disclosed herein.
Figure 6B:
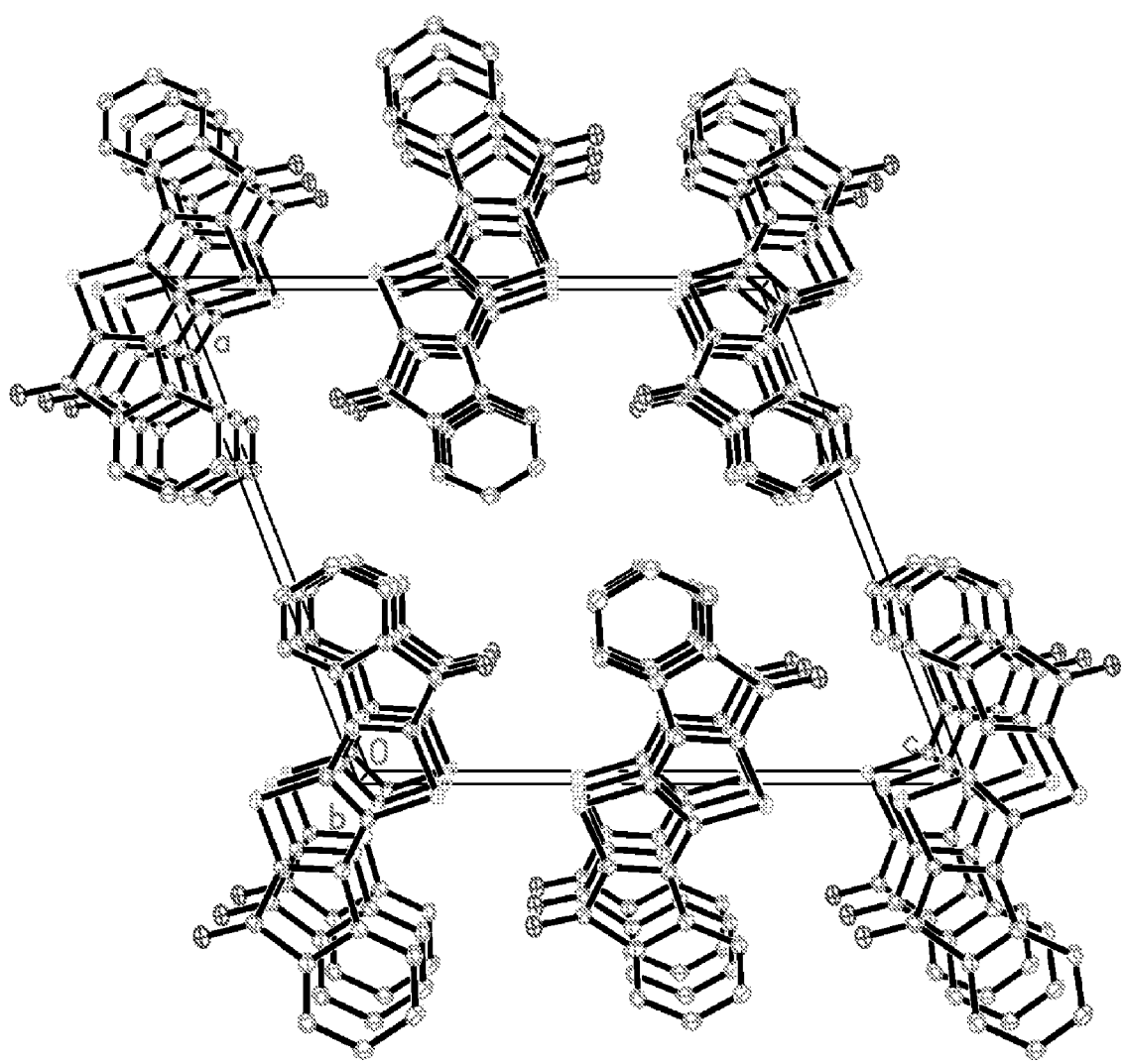

All three show distinct bond alternation with the "double" bonds averaging 1.36-1.37 Å and "single" bonds 1.44-1.45 Å, fully supporting the proposed quinoidal structures. These values are also in good agreement with those observed in their purely hydrocarbon analogues. The peripheral benzene rings in particular thieno-containing compounds have an average bond distance of 1.390 Å with a standard deviation of 0.006 Å. In some embodiments, the molecules are essentially planar, as the root-mean-square (RMS) deviation from the average molecular plane is negligible; 100 showed the greatest RMS deviation of only 0.042 Å. In addition to certain embodiments of the final compounds disclosed herein, single crystals suitable for X-ray diffraction of dione precursors 14 (FIG. 5A) and 26 (FIG. 5B) from CHCl$_3$/cyclohexane were obtained and upon slow cooling from refluxing nitrobenzene, respectively. Dione 14 alternates its orientation within the 1D stack such that the molecular arrangement would result in a net dipole; however, the dipole of the neighbouring stack balances the opposing dipole (see FIG. 6A). Dione 26 shows a more ordered 1D arrangement due to its centrosymmetry (see FIG. 6B). The distance between the average planes of 14 and 26 are essentially identical at 3.39 Å and 3.38 Å, respectively. Dione 14 has a significant RMS deviation from planarity of 0.079 Å while 26 is nearly planar at 0.027 Å. This is likely due to the steric crowding of the hydrogens in the bay region of 14. Interestingly, the carbonyl oxygens of 14 and 26 show a strong interaction with the bay carbons of adjacent stacks with distances of 3.25 Å for 9 and 3.28 Å for 26.

Figure 7:
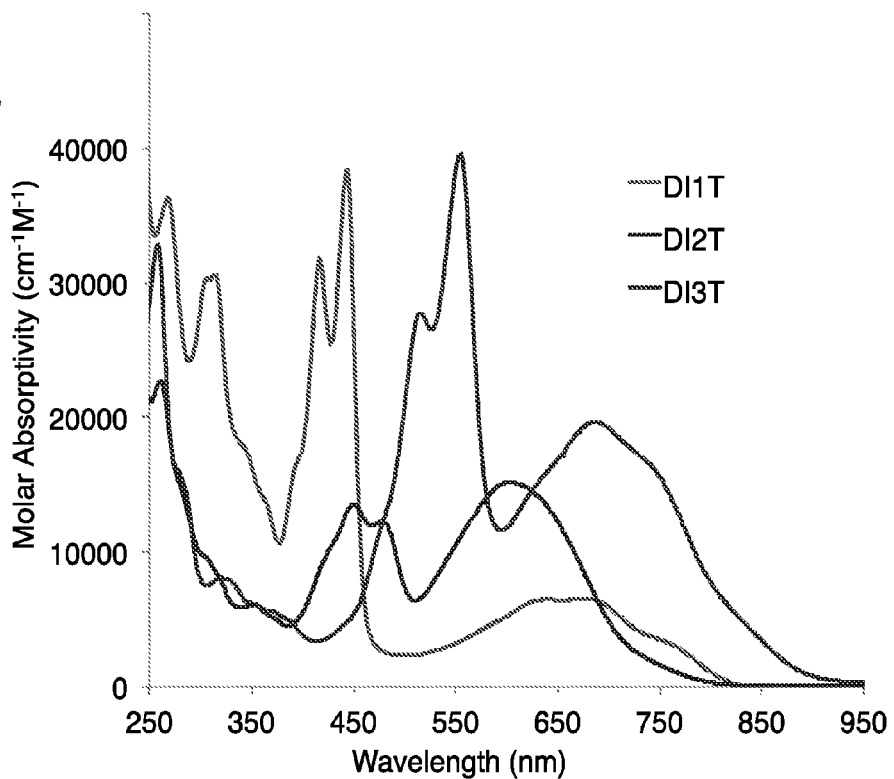
FIG. 7 is a combined electronic absorption spectrum illustrating spectra obtained from various compound embodiments disclosed herein.
Figure 8:
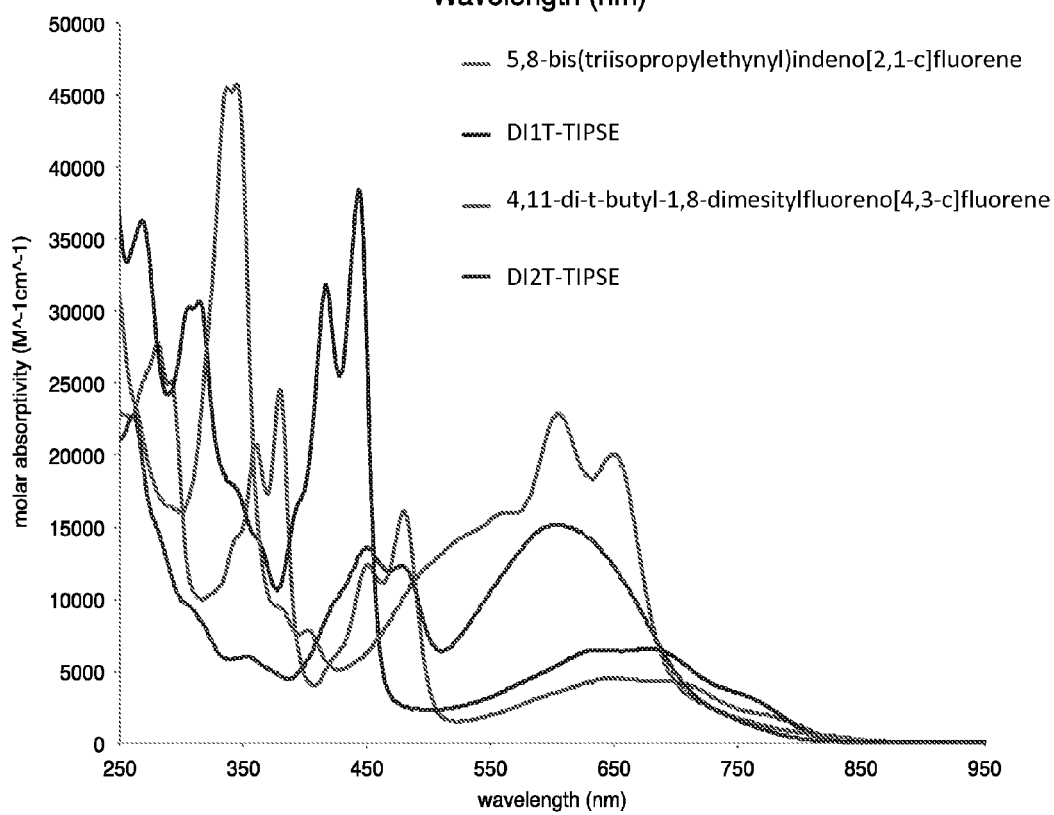
FIG. 8 is a combined electronic absorption spectrum comparing spectra obtained from various compound embodiments disclosed herein and spectra obtained from indeno[2,1-c]fluorene and fluoreno[3,4-c]fluorene cores.
Figure 9:
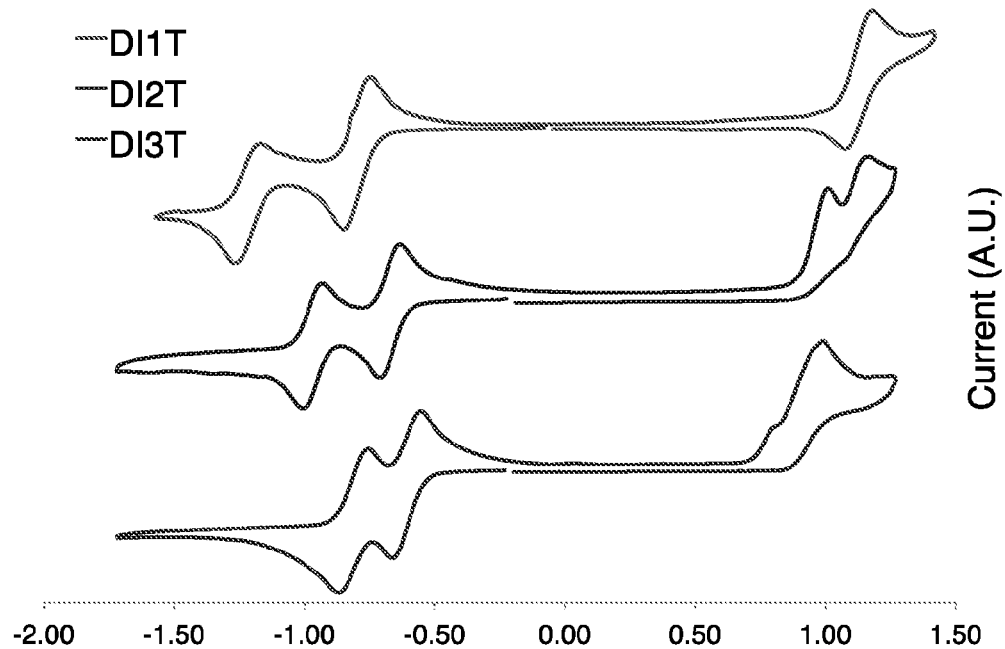
FIG. 9 is a combined cyclic voltammogram illustrating voltammograms obtained from various compound embodiments disclosed herein.

The deeply colored compound embodiments were characterized further by absorption spectroscopy (FIG. 7). All compounds exhibit strong, acene-like vibronic features from 350-600 nm and low energy absorptions reaching into the NIR (800-925 nm). The absorption edges are staggered, possibly as a result of the family's alternating axo/centrosymmetry. Interestingly, 100 and 138 exhibit similar absorbance profiles to the related indeno[2,1-c]fluorene and fluoreno[4,3-c]fluorene derivatives (FIG. 8). For particular compound embodiments, the high energy bands red shift by ca. 50-70 nm and the low energy bands blue shift by ca. 25-35 nm. Particular embodiments of the thieno-containing compounds disclosed herein are non-emissive. Particular thieno-containing compounds exhibit two reversible one electron reductions in solution as examined by cyclic voltammetry (FIG. 9 and Table 2).

TABLE 2

Electrochemical data for compounds (n = 1-3)[a]

| Compound | $E^1_{red}$ | $E^2_{red}$ | $E_{ox}$ | LUMO | HOMO | $E_{gap}$ |
|---|---|---|---|---|---|---|
| 100 | −0.80 | −1.22 | 1.13 | −3.84 | −5.77 | 1.93 |
| 138 | −0.67 | −0.97 | 1.02 | −3.97 | −5.66 | 1.69 |
| 132 | −0.61 | −0.81 | 0.99 | −4.03 | −5.63 | 1.60 |

[a]Values reported as the half-wave potential (vs. SCE) using the Fc/Fc+ couple (0.46 V) as an internal standard. HOMO and LUMO energy levels in eV were approximated using SCE ¼ 4.68 eV vs. vacuum (see ref. 23) and E½ values for reversible processes or Ep values for irreversible processes; Egap ¼ LUMO_HOMO. Calculated energy levels (B3LYP/6-31G(d, p)) in parentheses.

Figure 10A:
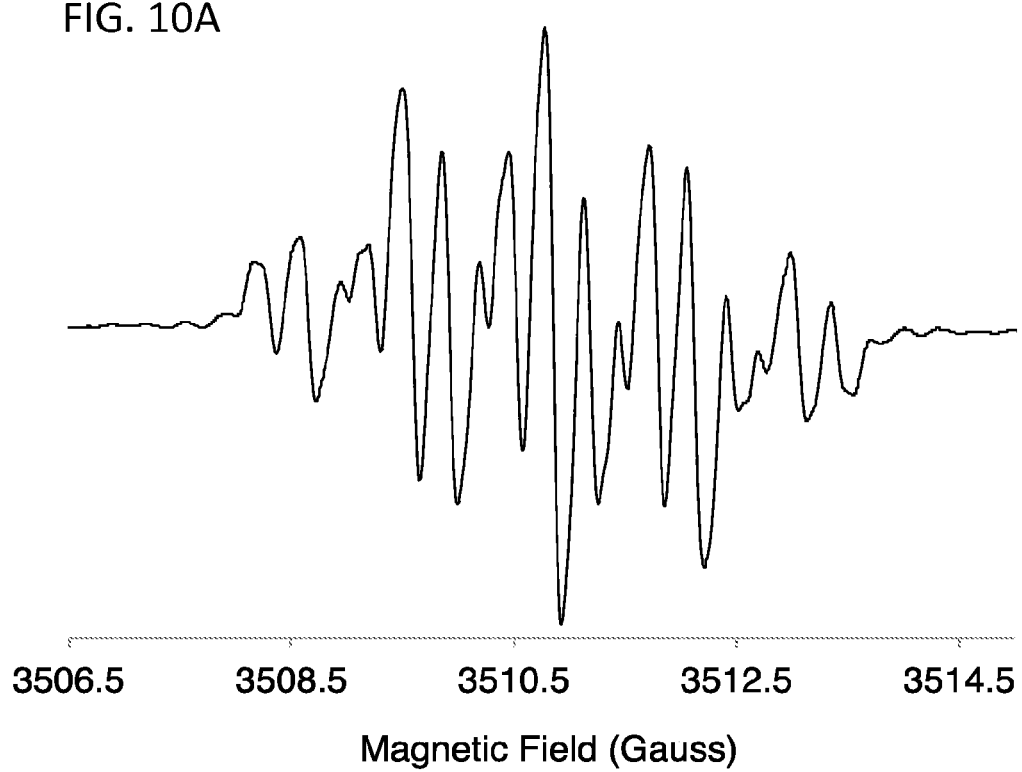
FIGS. 10A-10C are electron spin resonance spectra of radical anions of exemplary compound embodiments disclosed herein.
Figure 10B:
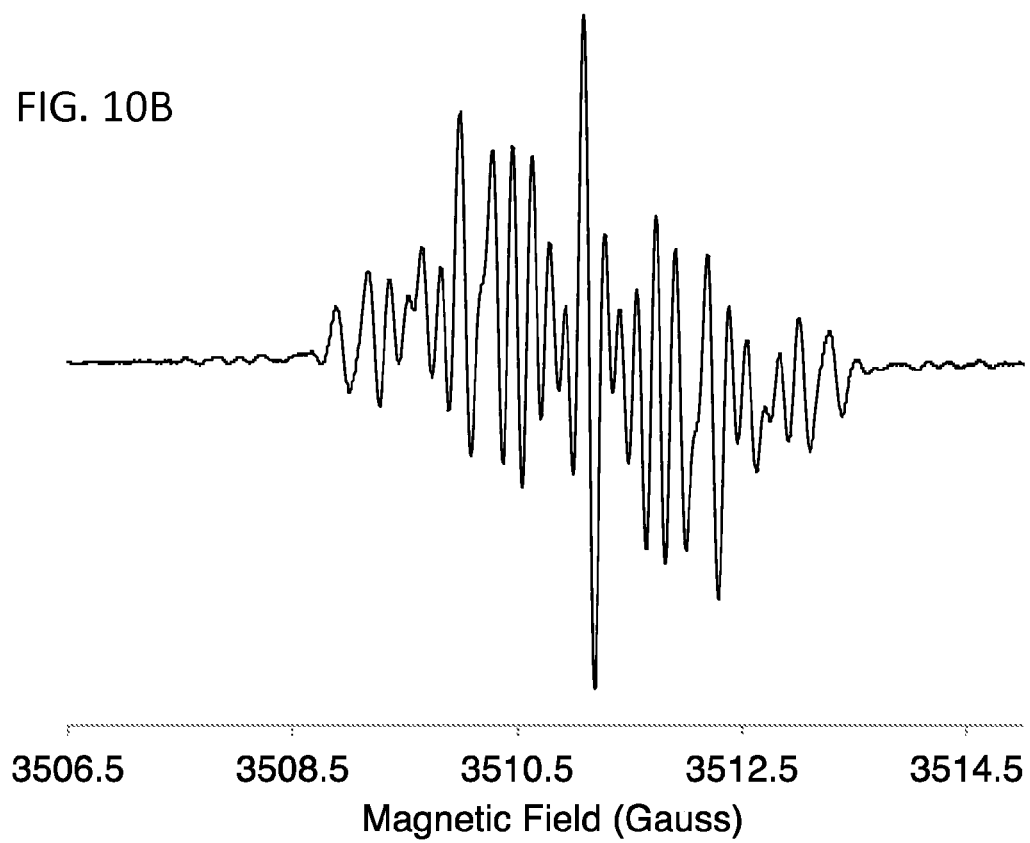
Figure 10C:
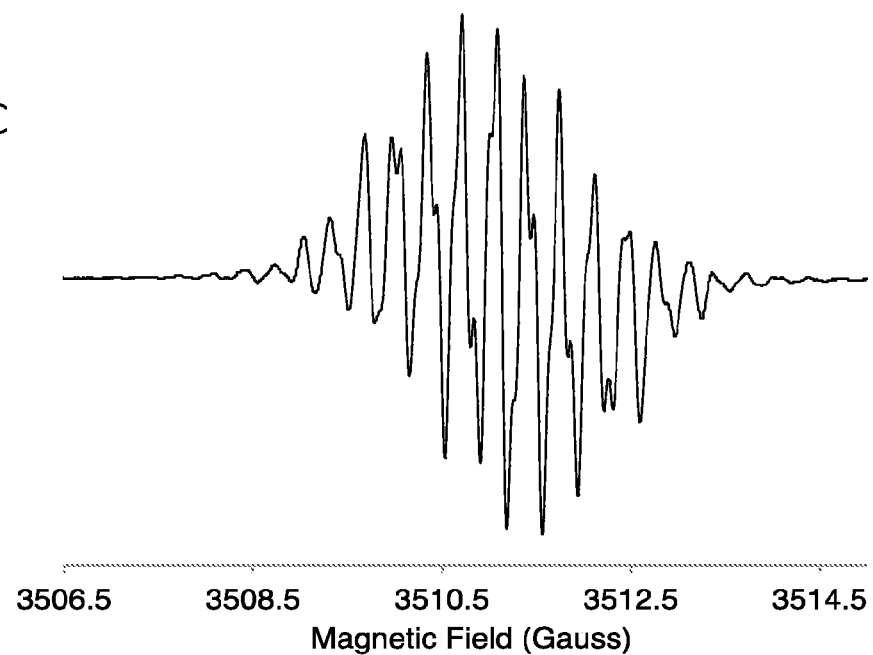

100 shows a reversible oxidation while the oxidation of 138 and 132 are essentially irreversible. The difference between $E_{red}^1$ and $E_{red}^2$ decreases by ca. 0.1 V upon sequential expansion of the quinoidal core. This is most likely due to the mitigation of columbic repulsion in the doubly reduced species. The values for $E_{ox}$ appear to approach a constant, indicating that incorporation of additional thiophene units does not alter the ionization potential to a large degree. LUMO and HOMO energy levels were derived from the $E_{red}^1$ and $E_{ox}$ values, respectively. $E_{gap}$ decreases over the series in nonlinear fashion. Particular embodiments of thieno-containing anion radicals were obtained by reduction of the neutral species with K metal in THF. The EPR spectrum of a blue solution of 100[*−] is shown in FIG. 10A; see ESI for the EPR spectra of 138[*−] (FIG. 10B) and 132[*−] (FIG. 10C). The hyperfine coupling constants (HFCCs) of the spin active nuclei were determined and experimental carbon spin densities (rc) were calculated by the McConnell equation (Tables 3 and 4). Due to the lack of spin active nuclei on the core of particular compound embodiments, $\rho_c$ could not be directly calculated. Very little spin density is contained within the fused benzene rings (0.004-0.044), with more contained in the ethynyl group (0.094-0.112). The approximate spin densities remaining in the core for 100, 138, and 132 are 0.59, 0.64, and 0.66, respectively, indicating that a majority of the spin density resides in the thienoacene unit.

TABLE 3

Carbon spin densities (ρc)a

| Position | Compound 100 | Compound 138 | Compound 132 |
|---|---|---|---|
| A | 0.034 | 0.022 | 0.024 |
| B | 0.012 | 0.016 | 0.014 |
| C | 0.044 | 0.029 | 0.028 |
| D | 0.004 | 0.010 | 0.010 |
| E | 0.112 | 0.103 | 0.094 |
| remainder | 0.59 | 0.64 | 0.66 |

[a]Labeling scheme:

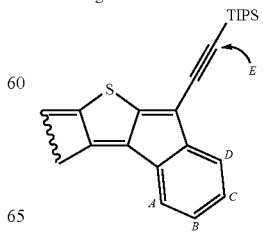

TABLE 4

Hyperfine Coupling Constants and Carbon spin densities (ρc).

|  | Compound 100 | Compound 138 | Compound 132 |
|---|---|---|---|
| C(A) | 0.034 | 0.022 | 0.024 |
| C(B) | 0.012 | 0.016 | 0.014 |
| C(C) | 0.044 | 0.029 | 0.028 |
| C(D) | 0.004 | 0.010 | 0.010 |
| C(E) | 0.112 | 0.103 | 0.094 |
| H(A) | 0.95 | 0.63 | 0.63 |
| H(B) | 0.35 | 0.46 | 0.38 |
| H(C) | 1.25 | 0.82 | 0.77 |
| H(D) | 0.11 | 0.28 | 0.27 |
| Si | 2.00 | 1.92 | 1.88 |
| QH | 28.1 | 28.2 | 26.6 |
| QSi | 17.9 | 18.6 | 20 |

<sup>a</sup>Labeling scheme:

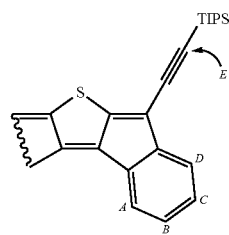

Figure 11A:
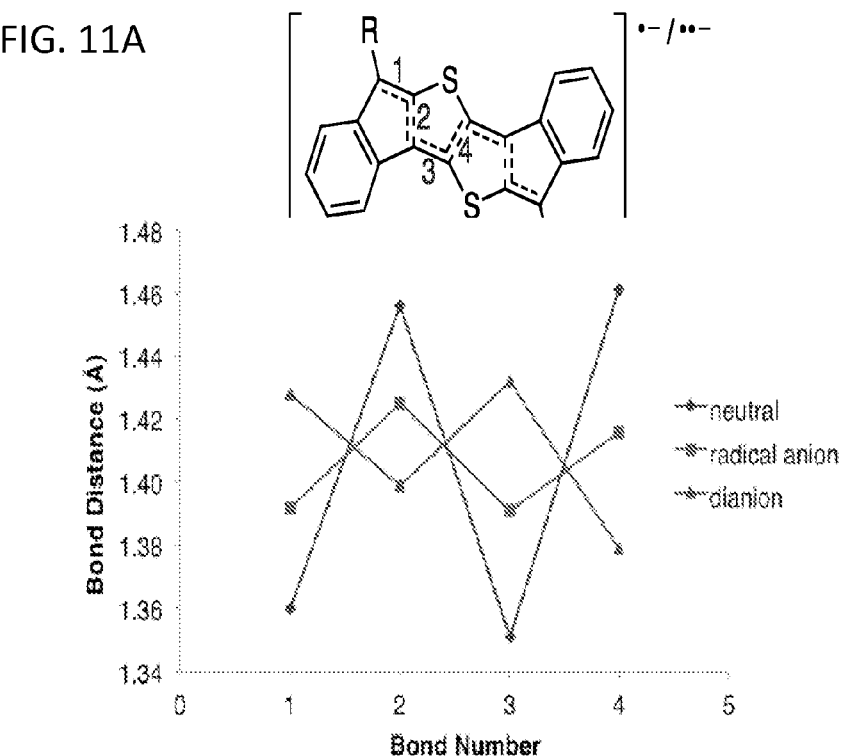
FIGS. 11A-11C are graphs (bond number vs. bond length in Angstroms) of bond distances upon reduction of exemplary compound embodiments disclosed herein.
Figure 11B:
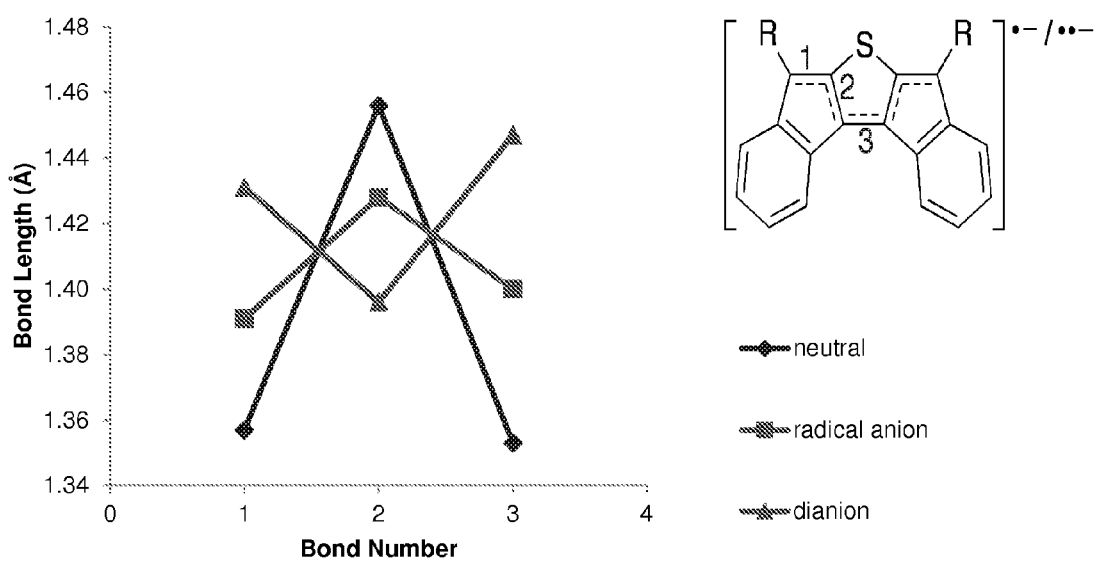
Figure 11C:
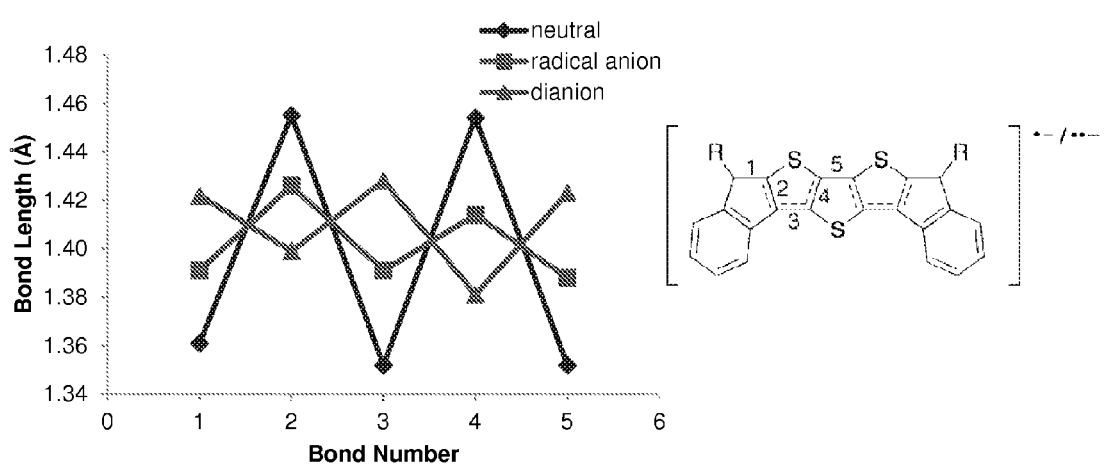

DFT calculations were performed to predict the geometry of the neutral, radical anion and dianion states of particular thieno-containing compounds. For computational ease, trimethylsilyl was used in place of the larger TIPS/TES groups. Bond distances in the core of 160 are shown in FIG. 11A and Table 5; values for compounds 158 and 162 are provided below in Tables 6 and 7 (see also FIGS. 11B and 11C). The calculations replicate the quinoidal character of the neutral thieno-containing compounds but overestimate the degree of bond alternation in 160 and 162 by as much as 0.02 Å compared to the solid state data (Table 1). Upon one electron reduction, the quinoidal bonds begin to homogenize as the unpaired electron is delocalized over the system. The dianion shows a reversal of the quinoidal pattern and thus the expected rearomatization of the central thiophenes. In accord with the CV experiments, the dianionic, fully aromatic species is stabilized with respect to the neutral state.

TABLE 5

Bond distances (Å) for Compound 158

| bond # | neutral | radical anion | dianion |
|---|---|---|---|
| 1 | 1.357 | 1.391 | 1.431 |
| 2 | 1.456 | 1.428 | 1.396 |
| 3 | 1.353 | 1.400 | 1.447 |

TABLE 6

Bond distances (Å) for Compound 160

| bond # | neutral | radical anion | dianion |
|---|---|---|---|
| 1 | 1.382 | 1.393 | 1.401 |
| 2 | 1.397 | 1.393 | 1.389 |
| 3 | 1.391 | 1.401 | 1.408 |
| 4 | 1.396 | 1.393 | 1.390 |
| 5 | 1.384 | 1.394 | 1.400 |
| 6 | 1.414 | 1.427 | 1.442 |
| 7 | 1.483 | 1.461 | 1.441 |
| 8 | 1.360 | 1.392 | 1.428 |
| 9 | 1.456 | 1.425 | 1.399 |
| 10 | 1.458 | 1.444 | 1.433 |
| 11 | 1.351 | 1.391 | 1.432 |
| 12 | 1.461 | 1.416 | 1.379 |

TABLE 7

Bond distances (Å) for Compound 162

| bond # | neutral | radical anion | dianion |
|---|---|---|---|
| 1 | 1.361 | 1.391 | 1.424 |
| 2 | 1.455 | 1.426 | 1.400 |
| 3 | 1.352 | 1.391 | 1.429 |
| 4 | 1.454 | 1.414 | 1.382 |
| 5 | 1.352 | 1.388 | 1.424 |

Methods characterizing the compound embodiments disclosed herein are described as well. In some embodiments, the methods of making the compounds can be used to rapidly make the compound embodiments disclosed herein; such methods being readily amenable to scalable procedures. In some embodiments, X-ray crystallography can be used to corroborate the presence of distinct quinoidal motifs and also can be used to show that compounds embodiments can be pack in progressively closer, pairwise 1D arrangements. Analysis of the reduced states by EPR spectra and DFT calculations indicate stable anionic species. The large degree of p-orbital overlap, NIR absorption and favorable electrochemical properties suggest great potential for application in organic electronics.

| Cartesian Coordinates | | | | | | |
|---|---|---|---|---|---|---|
| DI1T Neutral UCAM-B3LYP/6-31G(d, p) | | | | | | |

Zero-point correction = 0.448804 (Hartree/Particle)
Thermal correction to Energy = 0.481967
Thermal correction to Enthalpy = 0.482911
Thermal correction to Gibbs Free Energy = 0.379259
Sum of electronic and zero-point Energies = −2058.703728
Sum of electronic and thermal Energies = −2058.670565
Sum of electronic and thermal Enthalpies = −2058.669621
Sum of electronic and thermal Free Energies = −2058.773273
NIMAG = 0

| C | 1.93558 | 4.11556 | −0.0006 | C | 4.268 | 1.51855 | 0.00153 |
| C | 1.8226 | 2.73673 | 0.00025 | Si | 5.44268 | 2.93551 | −0.0004 |
| C | 3.21007 | 4.68787 | −0.0013 | C | −4.2719 | −1.517 | 0.0006 |
| C | 2.98224 | 1.92787 | 0.00039 | Si | −5.4389 | −2.9406 | −0.0005 |
| C | 4.24123 | 2.49387 | −0.0004 | C | −6.6374 | −2.732 | 1.43019 |

-continued

| Cartesian Coordinates | | | | | | | |
|---|---|---|---|---|---|---|---|
| C | 4.34546 | 3.88761 | −0.0013 | C | −4.4445 | −4.5199 | 0.20022 |
| H | 5.12629 | 1.86635 | −0.0006 | C | −6.3673 | −2.9522 | −1.6329 |
| H | 5.32724 | 4.34978 | −0.002 | C | 4.87476 | −4.1792 | −1.287 |
| H | 1.05689 | 4.7499 | −0.0007 | C | 5.44532 | −3.7152 | 1.7078 |
| H | 3.31141 | 5.76782 | −0.002 | C | 7.15304 | −2.2862 | −0.425 |
| C | 2.58279 | 0.49782 | 0.00128 | H | −3.8845 | −4.519 | 1.13918 |
| C | 0.67455 | 1.82696 | 0.00094 | H | −3.7274 | −4.6427 | −0.6159 |
| C | 1.22605 | 0.46961 | 0.00151 | H | −5.1025 | −5.3945 | 0.20288 |
| C | 3.4823 | −0.5911 | 0.00156 | H | −6.1106 | −2.7041 | 2.3877 |
| S | −0.0031 | −0.7843 | 0.00212 | H | −7.3485 | −3.5634 | 1.46294 |
| C | −1.2311 | 0.47082 | 0.00153 | H | −7.2107 | −1.8057 | 1.33711 |
| C | −0.6783 | 1.82761 | 0.00099 | H | 3.86916 | −4.5466 | −1.0656 |
| C | −1.8255 | 2.73845 | 0.00041 | H | 5.54809 | −5.0417 | −1.315 |
| C | −2.5878 | 0.50027 | 0.00113 | H | 4.85564 | −3.7361 | −2.2862 |
| C | −2.9859 | 1.93067 | 0.00049 | H | 4.45105 | −4.0803 | 1.97859 |
| C | −1.9371 | 4.11738 | −0.0002 | H | 5.75677 | −2.9976 | 2.4715 |
| C | −4.2443 | 2.49795 | −2E−05 | H | 6.13549 | −4.564 | 1.74364 |
| C | −3.2111 | 4.69094 | −0.0007 | H | 7.16412 | −1.8113 | −1.4098 |
| C | −4.3472 | 3.89178 | −0.0006 | H | 7.88358 | −3.101 | −0.4382 |
| H | −1.0578 | 4.75087 | −0.0003 | H | 7.49054 | −1.5201 | 0.30704 |
| H | −3.3114 | 5.77098 | −0.0012 | H | −6.9352 | −2.0287 | −1.7742 |
| H | −5.1299 | 1.87126 | 0.0001 | H | −7.0729 | −3.7881 | −1.6703 |
| H | −5.3286 | 4.35489 | −0.0011 | H | −5.6814 | −3.0548 | −2.478 |
| C | −3.4876 | −0.5882 | 0.00093 | | | | |

DI1T Radical Anion
UCAM-B3LYP/6-31++G(d, p)

Zero-point correction = 0.444806 (Hartree/Particle)
Thermal correction to Energy = 0.478102
Thermal correction to Enthalpy = 0.479046
Thermal correction to Gibbs Free Energy = 0.375054
Sum of electronic and zero-point Energies = −2058.828161
Sum of electronic and thermal Energies = −2058.794866
Sum of electronic and thermal Enthalpies = −2058.793921
Sum of electronic and thermal Free Energies = −2058.897913
NIMAG = 0

| C | 1.94799 | 4.11942 | 0.0031 | C | 4.28847 | −1.5201 | −0.0034 |
|---|---|---|---|---|---|---|---|
| C | 1.83308 | 2.73021 | 0.001 | Si | 5.42442 | −2.9367 | 0.00093 |
| C | 3.21242 | 4.70462 | 0.00361 | C | −4.2885 | −1.5201 | −0.0034 |
| C | 3.013 | 1.9249 | −0.0005 | Si | −5.4244 | −2.9367 | 0.00093 |
| C | 4.27089 | 2.52068 | −0.0002 | C | −5.7094 | −3.5493 | 1.76173 |
| C | 4.36507 | 3.91079 | 0.00198 | C | −4.6963 | −4.3416 | −1.0221 |
| H | 5.16532 | 1.90406 | −0.002 | C | −7.0806 | −2.4203 | −0.7378 |
| H | 5.34346 | 4.3834 | 0.00221 | C | 4.69622 | −4.3417 | −1.0219 |
| H | 1.06232 | 4.74584 | 0.00427 | C | 5.70953 | −3.5492 | 1.76176 |
| H | 3.30306 | 5.78712 | 0.00523 | C | 7.08056 | −2.4204 | −0.7379 |
| C | 2.62682 | 0.51601 | −0.0025 | H | −3.7256 | −4.6508 | −0.6222 |
| C | 0.70015 | 1.82703 | −0.0002 | H | −4.5411 | −4.0294 | −2.0592 |
| C | 1.23578 | 0.50367 | −0.0022 | H | −5.3581 | −5.2151 | −1.0228 |
| C | 3.50917 | −0.5773 | −0.0025 | H | −4.7663 | −3.8577 | 2.22313 |
| S | 0 | −0.7438 | −0.0041 | H | −6.3935 | −4.4055 | 1.77888 |
| C | −1.2358 | 0.50367 | −0.0022 | H | −6.1379 | −2.7582 | 2.38493 |
| C | −0.7002 | 1.82703 | −0.0002 | H | 3.72557 | −4.6509 | −0.6222 |
| C | −1.8331 | 2.73021 | 0.00101 | H | 5.35804 | −5.2151 | −1.0227 |
| C | −2.6268 | 0.51601 | −0.0025 | H | 4.54089 | −4.0295 | −2.0591 |
| C | −3.013 | 1.9249 | −0.0004 | H | 4.76637 | −3.8576 | 2.22323 |
| C | −1.948 | 4.11942 | 0.00311 | H | 6.13802 | −2.7581 | 2.38489 |
| C | −4.2709 | 2.52067 | −0.0002 | H | 6.39354 | −4.4054 | 1.77892 |
| C | −3.2124 | 4.70462 | 0.00363 | H | 6.95664 | −2.0751 | −1.7689 |
| C | −4.3651 | 3.91079 | 0.00201 | H | 7.78968 | −3.2558 | −0.7405 |
| H | −1.0623 | 4.74584 | 0.00428 | H | 7.52492 | −1.6004 | −0.1651 |
| H | −3.3031 | 5.78711 | 0.00525 | H | −7.525 | −1.6004 | −0.1649 |
| H | −5.1653 | 1.90406 | −0.002 | H | −7.7897 | −3.2558 | −0.7404 |
| H | −5.3435 | 4.3834 | 0.00224 | H | −6.9567 | −2.0749 | −1.7687 |
| C | −3.5092 | −0.5773 | −0.0025 | | | | |

DI1T Dianion
UCAM-B3LYP/6-31++G(d, p)

Zero-point correction = 0.442213 (Hartree/Particle)
Thermal correction to Energy = 0.475713
Thermal correction to Enthalpy = 0.476657
Thermal correction to Gibbs Free Energy = 0.372411
Sum of electronic and zero-point Energies = −2058.797119
Sum of electronic and thermal Energies = −2058.763620

-continued

Cartesian Coordinates

Sum of electronic and thermal Enthalpies = −2058.762676
Sum of electronic and thermal Free Energies = −2058.866921
NIMAG = 0

| | | | | | | | |
|---|---|---|---|---|---|---|---|
| C | −1.9614 | 4.10054 | 0.01211 | C | −4.3392 | −1.5161 | −0.0013 |
| C | −1.8437 | 2.70439 | 0.00652 | Si | −5.4709 | −2.8982 | −0.0031 |
| C | −3.2173 | 4.69851 | 0.01847 | C | 4.34126 | −1.5167 | −0.0284 |
| C | −3.044 | 1.90052 | 0.00746 | Si | 5.46945 | −2.9014 | 0.00762 |
| C | −4.2986 | 2.52313 | 0.01394 | C | 6.97412 | −2.5998 | −1.1068 |
| C | −4.3839 | 3.91054 | 0.01938 | C | 4.61708 | −4.4849 | −0.5823 |
| H | −5.2006 | 1.91486 | 0.01461 | C | 6.15385 | −3.2537 | 1.74296 |
| H | −5.3601 | 4.39176 | 0.02441 | C | −5.2536 | −4.0158 | 1.51347 |
| H | −1.0694 | 4.72052 | 0.01145 | C | −5.253 | −4.0117 | −1.5226 |
| H | −3.2978 | 5.78361 | 0.02274 | C | −7.2655 | −2.2894 | −0.0024 |
| C | −2.6724 | 0.50957 | 0.00102 | H | 4.26668 | −4.3738 | −1.6132 |
| C | −0.7216 | 1.80756 | −0.0006 | H | 3.74198 | −4.703 | 0.03801 |
| C | −1.2417 | 0.51219 | −0.0037 | H | 5.2941 | −5.3468 | −0.5373 |
| C | −3.5452 | −0.5711 | −0.0003 | H | 6.6607 | −2.4614 | −2.1464 |
| S | 0.00252 | −0.7285 | −0.0128 | H | 7.68083 | −3.4381 | −1.0663 |
| C | 1.24609 | 0.51285 | −0.0121 | H | 7.50346 | −1.6916 | −0.8 |
| C | 0.7254 | 1.80793 | −0.0054 | H | −4.2291 | −4.3988 | 1.56319 |
| C | 1.84709 | 2.7053 | −0.0054 | H | −5.9395 | −4.872 | 1.48701 |
| C | 2.67682 | 0.51087 | −0.0166 | H | −5.437 | −3.4538 | 2.43487 |
| C | 3.04781 | 1.90205 | −0.0123 | H | −4.2283 | −4.3942 | −1.5732 |
| C | 1.96399 | 4.10152 | −0.0001 | H | −5.4365 | −3.4474 | −2.4425 |
| C | 4.30196 | 2.52549 | −0.0139 | H | −5.9385 | −4.8683 | −1.4984 |
| C | 3.21951 | 4.70024 | −0.0018 | H | −7.4642 | −1.6743 | 0.88113 |
| C | 4.38655 | 3.91291 | −0.0087 | H | −7.9716 | −3.1288 | −0.0031 |
| H | 1.07167 | 4.72096 | 0.00517 | H | −7.4644 | −1.6727 | −0.8848 |
| H | 3.29943 | 5.78537 | 0.0022 | H | 6.68105 | −2.3767 | 2.13321 |
| H | 5.20432 | 1.91777 | −0.0197 | H | 6.85063 | −4.1018 | 1.74123 |
| H | 5.36254 | 4.39469 | −0.0101 | H | 5.33797 | −3.4796 | 2.43715 |
| C | 3.54968 | −0.5697 | −0.0211 | | | | |

DI2T Neutral
UCAM-B3LYP/6-31G(d, p)

Zero-point correction = 0.463062 (Hartree/Particle)
Thermal correction to Energy = 0.498623
Thermal correction to Enthalpy = 0.499567
Thermal correction to Gibbs Free Energy = 0.389852
Sum of electronic and zero-point Energies = −2533.040684
Sum of electronic and thermal Energies = −2533.005123
Sum of electronic and thermal Enthalpies = −2533.004179
Sum of electronic and thermal Free Energies = −2533.113894
NIMAG = 0

| | | | | | | | |
|---|---|---|---|---|---|---|---|
| C | 4.07561 | 3.49564 | −0.1123 | H | −1.7808 | −6.0079 | 0.20066 |
| C | 3.20184 | 2.42553 | −0.0779 | H | −4.216 | −5.6358 | 0.18502 |
| C | 1.80398 | 2.6386 | −0.0872 | C | 5.86787 | −0.1146 | 0.01072 |
| C | 1.28393 | 3.92068 | −0.131 | Si | 7.54086 | −0.8814 | 0.03869 |
| C | 1.18186 | 1.32102 | −0.0438 | C | 7.35853 | −2.6817 | 0.53848 |
| C | 2.17037 | 4.9984 | −0.1657 | C | 8.59984 | 0.0418 | 1.28481 |
| H | 0.21176 | 4.08979 | −0.1384 | C | 8.28952 | −0.7503 | −1.6786 |
| C | 3.54523 | 4.78691 | −0.1564 | H | 7.67699 | −1.2718 | −2.4189 |
| H | 1.78196 | 6.01058 | −0.2002 | H | 9.29024 | −1.1932 | −1.6993 |
| H | 4.2172 | 5.63849 | −0.1838 | H | 8.37893 | 0.29253 | −1.9945 |
| H | 5.14807 | 3.33146 | −0.105 | H | 8.16859 | −0.0112 | 2.288 |
| C | 3.47382 | 0.96806 | −0.0286 | H | 8.69798 | 1.09772 | 1.01872 |
| C | 2.26383 | 0.34784 | −0.0096 | H | 9.60609 | −0.3865 | 1.32941 |
| C | 4.7578 | 0.38065 | −0.0073 | H | 6.90672 | −2.7744 | 1.52967 |
| S | 1.69141 | −1.3132 | 0.04584 | H | 8.33457 | −3.176 | 0.56758 |
| C | 0.03465 | −0.7281 | 0.02395 | H | 6.72821 | −3.2276 | −0.1686 |
| C | −0.0335 | 0.73074 | −0.0255 | C | −5.8675 | 0.11525 | −0.0115 |
| S | −1.6902 | 1.31584 | −0.0472 | Si | −7.5425 | 0.8776 | −0.0383 |
| C | −2.2627 | −0.3452 | 0.0083 | C | −7.4762 | 2.49142 | 0.91892 |
| C | −1.1807 | −1.3184 | 0.04249 | C | −8.7505 | −0.3138 | 0.76682 |
| C | −1.8028 | −2.636 | 0.08627 | C | −8.0298 | 1.19393 | −1.8239 |
| C | −3.2006 | −2.423 | 0.07732 | H | −7.1792 | 2.32397 | 1.95761 |
| C | −1.2827 | −3.9181 | 0.13045 | H | −8.4563 | 2.97862 | 0.92488 |
| C | −3.4726 | −0.9655 | 0.02768 | H | −6.7596 | 3.18732 | 0.4746 |
| C | −4.0744 | −3.493 | 0.11253 | H | −7.3268 | 1.87389 | −2.3125 |
| C | −4.7568 | −0.3786 | 0.0062 | H | −9.0257 | 1.64477 | −1.879 |
| C | −2.1692 | −4.9958 | 0.16585 | H | −8.0505 | 0.26505 | −2.4001 |
| H | −0.2105 | −4.0872 | 0.13761 | H | −8.4685 | −0.5268 | 1.80141 |

-continued

| | | Cartesian Coordinates | | | | |
|---|---|---|---|---|---|---|
| C | −3.544 | −4.7843 | 0.15694 | H | −8.7896 | −1.2644 | 0.22808 |
| H | −5.1469 | −3.3288 | 0.10588 | H | −9.7607 | 0.10721 | 0.77492 |

DI2T Radical Anion
UCAM-B3LYP/6-31++G(d, p)

Zero-point correction = 0.459072 (Hartree/Particle)
Thermal correction to Energy = 0.494818
Thermal correction to Enthalpy = 0.495763
Thermal correction to Gibbs Free Energy = 0.385295
Sum of electronic and zero-point Energies = −2533.175198
Sum of electronic and thermal Energies = −2533.139451
Sum of electronic and thermal Enthalpies = −2533.138507
Sum of electronic and thermal Free Energies = −2533.248975
NIMAG = 0

| C | −4.2116 | −3.3893 | −0.0039 | H | 1.97134 | 5.958 | −0.0033 |
|---|---|---|---|---|---|---|---|
| C | −3.3164 | −2.3221 | −0.0048 | H | 4.40835 | 5.5279 | −0.0013 |
| C | −1.9111 | −2.5707 | −0.0059 | C | −5.8953 | 0.30046 | 0.00009 |
| C | −1.43 | −3.8785 | −0.0062 | Si | −7.5119 | 1.13178 | 0.00846 |
| C | −1.2578 | −1.2824 | −0.0064 | C | −7.2569 | 2.99101 | −0.1488 |
| C | −2.3368 | −4.9353 | −0.0054 | C | −8.4239 | 0.76311 | 1.61691 |
| H | −0.3611 | −4.073 | −0.0071 | C | −8.5597 | 0.52167 | −1.4353 |
| C | −3.7159 | −4.6907 | −0.0042 | H | −8.0665 | 0.73011 | −2.3896 |
| H | −1.9714 | −5.958 | −0.0056 | H | −9.5415 | 1.00827 | −1.4448 |
| H | −4.4084 | −5.5279 | −0.0036 | H | −8.7177 | −0.5596 | −1.3744 |
| H | −5.2819 | −3.2036 | −0.0031 | H | −7.8487 | 1.11356 | 2.47929 |
| C | −3.5467 | −0.8792 | −0.0047 | H | −8.5798 | −0.3132 | 1.73958 |
| C | −2.2839 | −0.2934 | −0.0058 | H | −9.404 | 1.25313 | 1.63854 |
| C | −4.8002 | −0.2434 | −0.0023 | H | −6.6515 | 3.3734 | 0.67866 |
| S | −1.6488 | 1.34103 | −0.0059 | H | −8.2151 | 3.52251 | −0.1439 |
| C | −0.0092 | 0.7077 | −0.0063 | H | −6.7363 | 3.2363 | −1.0794 |
| C | 0.0092 | −0.7077 | −0.0066 | C | 5.89532 | −0.3005 | 0.00024 |
| S | 1.6488 | −1.341 | −0.0064 | Si | 7.51189 | −1.1318 | 0.00841 |
| C | 2.28391 | 0.29341 | −0.0056 | C | 7.2569 | −2.991 | −0.1493 |
| C | 1.25784 | 1.28239 | −0.0059 | C | 8.42385 | −0.7635 | 1.61699 |
| C | 1.91111 | 2.57067 | −0.0049 | C | 8.55969 | −0.5212 | −1.4351 |
| C | 3.31637 | 2.32209 | −0.0038 | H | 6.65151 | −3.3736 | 0.67796 |
| C | 1.42996 | 3.87849 | −0.0047 | H | 8.2151 | −3.5224 | −0.1446 |
| C | 3.54674 | 0.87917 | −0.0042 | H | 6.7363 | −3.236 | −1.08 |
| C | 4.21158 | 3.38925 | −0.0025 | H | 8.06659 | −0.7294 | −2.3895 |
| C | 4.80016 | 0.24338 | −0.002 | H | 9.54159 | −1.0078 | −1.4448 |
| C | 2.33681 | 4.93528 | −0.0034 | H | 8.71774 | 0.56005 | −1.3739 |
| H | 0.36108 | 4.073 | −0.0055 | H | 7.8486 | −1.1143 | 2.47925 |
| C | 3.71593 | 4.69067 | −0.0023 | H | 8.57977 | 0.31278 | 1.73998 |
| H | 5.28184 | 3.20354 | −0.0017 | H | 9.40393 | −1.2535 | 1.6385 |

DI2T Dianion
UCAM-B3LYP/6-31++G(d, p)

Zero-point correction = 0.456790 (Hartree/Particle)
Thermal correction to Energy = 0.492717
Thermal correction to Enthalpy = 0.493661
Thermal correction to Gibbs Free Energy = 0.383872
Sum of electronic and zero-point Energies = −2533.159282
Sum of electronic and thermal Energies = −2533.123355
Sum of electronic and thermal Enthalpies = −2533.122411
Sum of electronic and thermal Free Energies = −2533.232201
NIMAG = 0

| C | 4.26785 | 3.38184 | −0.0167 | H | −2.0211 | −5.9497 | −0.0196 |
|---|---|---|---|---|---|---|---|
| C | 3.37813 | 2.29933 | −0.0183 | H | −4.4686 | −5.5193 | −0.0158 |
| C | 1.95863 | 2.55021 | −0.0205 | C | 5.94404 | −0.3115 | −0.0069 |
| C | 1.48655 | 3.86803 | −0.0211 | Si | 7.53776 | −1.1271 | 0.03143 |
| C | 1.30352 | 1.27556 | −0.0213 | C | 7.3303 | −2.9994 | −0.1297 |
| C | 2.38848 | 4.92602 | −0.0196 | C | 8.47601 | −0.7892 | 1.64397 |
| H | 0.41642 | 4.06204 | −0.0227 | C | 8.6621 | −0.5436 | −1.3787 |
| C | 3.77505 | 4.68087 | −0.0174 | H | 8.20645 | −0.7631 | −2.3494 |
| H | 2.02113 | 5.94968 | −0.0201 | H | 9.64427 | −1.0309 | −1.3395 |
| H | 4.46863 | 5.51933 | −0.0163 | H | 8.81583 | 0.53934 | −1.3262 |
| H | 5.33993 | 3.19867 | −0.0152 | H | 7.90266 | −1.1497 | 2.50394 |
| C | 3.60419 | 0.87589 | −0.018 | H | 8.63034 | 0.28624 | 1.7813 |
| C | 2.29996 | 0.29414 | −0.0201 | H | 9.45725 | −1.2801 | 1.65278 |
| C | 4.8411 | 0.23817 | −0.0118 | H | 6.70855 | −3.3903 | 0.68175 |
| S | 1.64345 | −1.33 | −0.0208 | H | 8.29894 | −3.5128 | −0.0991 |
| C | 0.00295 | −0.6893 | −0.0221 | H | 6.83564 | −3.2538 | −1.0723 |
| C | −0.0029 | 0.68926 | −0.0222 | C | −5.944 | 0.31148 | −0.007 |

Cartesian Coordinates

| | | | | | | | |
|---|---|---|---|---|---|---|---|
| S | −1.6435 | 1.33004 | −0.021 | Si | −7.5378 | 1.12706 | 0.03139 |
| C | −2.3 | −0.2941 | −0.0201 | C | −7.3305 | 2.99918 | −0.1325 |
| C | −1.3035 | −1.2756 | −0.0212 | C | −8.4749 | 0.79134 | 1.64505 |
| C | −1.9586 | −2.5502 | −0.0203 | C | −8.6631 | 0.5416 | −1.3771 |
| C | −3.3781 | −2.2993 | −0.0182 | H | −6.7081 | 3.3912 | 0.67798 |
| C | −1.4865 | −3.868 | −0.0207 | H | −8.2991 | 3.51256 | −0.1017 |
| C | −3.6042 | −0.8759 | −0.018 | H | −6.8366 | 3.25232 | −1.0758 |
| C | −4.2679 | −3.3818 | −0.0165 | H | −8.2082 | 0.75989 | −2.3485 |
| C | −4.8411 | −0.2382 | −0.0119 | H | −9.6453 | 1.02889 | −1.3378 |
| C | −2.3885 | −4.926 | −0.0192 | H | −8.8167 | −0.5413 | −1.3231 |
| H | −0.4164 | −4.062 | −0.0223 | H | −7.9009 | 1.15302 | 2.50412 |
| C | −3.7751 | −4.6809 | −0.017 | H | −8.6291 | −0.2839 | 1.78395 |
| H | −5.3399 | −3.1987 | −0.015 | H | −9.4561 | 1.28234 | 1.65392 |

DI3T Neutral
UCAM-B3LYP/6-31G(d, p)

Zero-point correction = 0.476970 (Hartree/Particle)
Thermal correction to Energy = 0.515018
Thermal correction to Enthalpy = 0.515962
Thermal correction to Gibbs Free Energy = 0.400435
Sum of electronic and zero-point Energies = −3007.373585
Sum of electronic and thermal Energies = −3007.335538
Sum of electronic and thermal Enthalpies = −3007.334594
Sum of electronic and thermal Free Energies = −3007.450121
NIMAG = 0

| | | | | | | | |
|---|---|---|---|---|---|---|---|
| C | −6.1443 | −2.2991 | 0.00174 | H | 5.16182 | −5.5592 | −0.0017 |
| C | −4.8936 | −1.7095 | 0.00162 | H | 7.19764 | −4.1713 | −0.0018 |
| C | −6.2237 | −3.6929 | 0.00177 | H | 7.04067 | −1.6878 | −0.0017 |
| C | −5.0747 | −4.478 | 0.00164 | C | 6.2035 | 1.73175 | −0.0013 |
| C | −3.7247 | −2.5061 | 0.0014 | Si | 7.38808 | 3.13245 | 0.00115 |
| C | −3.8103 | −3.8883 | 0.00143 | C | −6.2035 | 1.73175 | 0.00136 |
| C | −4.5107 | −0.2778 | 0.00156 | Si | −7.3881 | 3.13984 | −0.0012 |
| C | −2.5961 | −1.5857 | 0.00107 | C | 6.82671 | 4.39115 | 1.28349 |
| C | −3.1501 | −0.2407 | 0.00119 | C | 7.40236 | 3.91793 | −1.7079 |
| C | −5.4151 | 0.8062 | 0.00162 | C | 9.09226 | 2.47852 | 0.43185 |
| S | −1.9172 | 1.0119 | 0.00067 | C | −7.4031 | 3.91739 | 1.70815 |
| C | −1.2438 | −1.5725 | 0.00053 | C | −9.0921 | 2.47863 | −0.4328 |
| C | −0.6762 | −0.2344 | 0.00028 | C | −6.8262 | 4.39155 | −1.2829 |
| C | 0.67622 | −0.2344 | −0.0003 | H | 9.09687 | 2.00532 | 1.41742 |
| C | 1.24379 | −1.5725 | −0.0005 | H | 9.82886 | 3.28788 | 0.44578 |
| S | 0 | −2.8141 | −1E−05 | H | 9.42627 | 1.73598 | −0.2979 |
| C | 2.59609 | −1.5857 | −0.0011 | H | 5.82513 | 4.76729 | 1.05846 |
| C | 3.15007 | −0.2407 | −0.0012 | H | 7.50744 | 5.24775 | 1.31167 |
| S | 1.9172 | 1.0119 | −0.0007 | H | 6.80089 | 3.95047 | 2.28363 |
| C | 3.72473 | −2.5061 | −0.0014 | H | 8.0999 | 4.76071 | −1.7426 |
| C | 4.89364 | −1.7095 | −0.0016 | H | 6.41219 | 4.29148 | −1.9823 |
| C | 4.51073 | −0.2778 | −0.0016 | H | 7.70993 | 3.1969 | −2.47 |
| C | 5.41514 | 0.80619 | −0.0016 | H | −5.8247 | 4.76758 | −1.0573 |
| H | −2.9169 | −4.5049 | 0.00128 | H | −7.5069 | 5.2482 | −1.311 |
| H | −5.1618 | −5.5592 | 0.00167 | H | −6.8 | 3.95123 | −2.2832 |
| H | −7.0407 | −1.6878 | 0.00168 | H | −7.7108 | 3.19612 | 2.46988 |
| H | −7.1976 | −4.1713 | 0.00184 | H | −8.1006 | 4.76013 | 1.74286 |
| C | 3.81027 | −3.8883 | −0.0014 | H | −6.413 | 4.29091 | 1.98296 |
| C | 5.07472 | −4.478 | −0.0016 | H | −9.4264 | 1.7359 | 0.29667 |
| C | 6.22368 | −3.6929 | −0.0018 | H | −9.0963 | 2.00567 | −1.4184 |
| C | 6.14426 | −2.2991 | −0.0017 | H | −9.8287 | 3.28799 | −0.4468 |
| H | 2.91685 | −4.5049 | −0.0013 | | | | |

DI3T Radical Anion
UCAM-B3LYP/6-31++G(d, p)

Zero-point correction = 0.473045 (Hartree/Particle)
Thermal correction to Energy = 0.511285
Thermal correction to Enthalpy = 0.512229
Thermal correction to Gibbs Free Energy = 0.396153
Sum of electronic and zero-point Energies = −3007.518003
Sum of electronic and thermal Energies = −3007.479764
Sum of electronic and thermal Enthalpies = −3007.478820
Sum of electronic and thermal Free Energies = −3007.594896
NIMAG = 0

| | | | | | | | |
|---|---|---|---|---|---|---|---|
| C | 6.18998 | −2.3207 | 0.00125 | H | −2.9446 | −4.5042 | −0.0016 |
| C | 4.93936 | −1.7069 | 0.00111 | H | −5.1797 | −5.5737 | −0.0024 |
| C | 6.26311 | −3.711 | 0.00113 | H | −7.2332 | −4.1932 | −0.0024 |
| C | 5.10098 | −4.4931 | 0.00088 | H | −7.0906 | −1.7145 | −0.0015 |

-continued

| \multicolumn{6}{c|}{Cartesian Coordinates} |
|---|---|---|---|---|---|
| C | 3.75533 | −2.5031 | 0.00084 | C | −6.2351 | 1.73653 | 0.00022 |
| C | 3.84434 | −3.894 | 0.00074 | Si | −7.3848 | 3.14656 | 0.00125 |
| C | 4.56729 | −0.294 | 0.00106 | C | 6.23663 | 1.73618 | 0.00086 |
| C | 2.63834 | −1.5887 | 0.00071 | Si | 7.38182 | 3.15018 | −0.001 |
| C | 3.17681 | −0.2684 | 0.00089 | C | −7.1064 | 4.20854 | −1.53 |
| C | 5.45642 | 0.79531 | 0.00115 | C | −7.1108 | 4.20277 | 1.53725 |
| S | 1.93882 | 0.97404 | 0.00072 | C | −9.1554 | 2.50131 | −0.0025 |
| C | 1.24775 | −1.5716 | 0.00044 | C | 8.59216 | 2.9919 | −1.437 |
| C | 0.69588 | −0.2693 | 0.00049 | C | 8.35441 | 3.19731 | 1.61291 |
| C | −0.6923 | −0.269 | 0.00021 | C | 6.39797 | 4.74511 | −0.183 |
| C | −1.2448 | −1.571 | −0.0002 | H | −9.3457 | 1.8862 | −0.8873 |
| S | 0.00121 | −2.803 | −6E−05 | H | −9.8749 | 3.32761 | −0.002 |
| C | −2.6354 | −1.5875 | −0.0005 | H | −9.3483 | 1.88303 | 0.87963 |
| C | −3.1733 | −0.2669 | −0.0003 | H | −6.0798 | 4.58606 | −1.5615 |
| S | −1.9347 | 0.97487 | 0.00027 | H | −7.7853 | 5.06869 | −1.5429 |
| C | −3.7528 | −2.5014 | −0.001 | H | −7.273 | 3.62882 | −2.443 |
| C | −4.9364 | −1.7047 | −0.001 | H | −6.0843 | 4.58025 | 1.57305 |
| C | −4.5638 | −0.292 | −0.0005 | H | −7.2798 | 3.61954 | 2.44756 |
| C | −5.4529 | 0.79728 | −0.0002 | H | −7.7898 | 5.06278 | 1.5516 |
| H | 2.94626 | −4.5055 | 0.00053 | H | 5.829 | 4.74885 | −1.1176 |
| H | 5.18084 | −5.5761 | 0.00078 | H | 7.05952 | 5.61851 | −0.1834 |
| H | 7.09342 | −1.7177 | 0.00131 | H | 5.68434 | 4.85983 | 0.6385 |
| H | 7.23494 | −4.1965 | 0.0012 | H | 9.17031 | 2.06575 | −1.3606 |
| C | −3.8424 | −3.8923 | −0.0015 | H | 9.29665 | 3.83109 | −1.4552 |
| C | −5.0994 | −4.4907 | −0.002 | H | 8.06123 | 2.97196 | −2.3936 |
| C | −6.2611 | −3.7082 | −0.002 | H | 8.92847 | 2.2757 | 1.75039 |
| C | −6.1874 | −2.3178 | −0.0015 | H | 7.68187 | 3.29827 | 2.47015 |
| | | | | H | 9.05536 | 4.03957 | 1.62828 |

| \multicolumn{6}{c|}{DI3T Dianion UCAM-B3LYP/6-31++G(d, p)} |
|---|---|---|---|---|---|

Zero-point correction = 0.471050 (Hartree/Particle)
Thermal correction to Energy = 0.509493
Thermal correction to Enthalpy = 0.510437
Thermal correction to Gibbs Free Energy = 0.394727
Sum of electronic and zero-point Energies = −3007.516246
Sum of electronic and thermal Energies = −3007.477803
Sum of electronic and thermal Enthalpies = −3007.476858
Sum of electronic and thermal Free Energies = −3007.592569
NIMAG = 0

| C | 6.2363 | 2.32246 | −2E−05 | H | −2.9777 | 4.48604 | 0.00003 |
|---|---|---|---|---|---|---|---|
| C | 4.98782 | 1.68616 | −2E−05 | H | −5.2024 | 5.57339 | 0.00006 |
| C | 6.30279 | 3.70966 | −1E−05 | H | −7.2732 | 4.20154 | 0.00007 |
| C | 5.1298 | 4.48844 | −1E−05 | H | −7.1457 | 1.72617 | 0.00004 |
| C | 3.78808 | 2.48293 | −2E−05 | C | −6.2978 | −1.7343 | −1E−05 |
| C | 3.8806 | 3.87977 | −1E−05 | Si | −7.4386 | −3.1193 | 0 |
| C | 4.62741 | 0.29019 | −3E−05 | C | 6.29778 | −1.7343 | −2E−05 |
| C | 2.68036 | 1.57474 | −2E−05 | Si | 7.43866 | −3.1192 | 0.00003 |
| C | 3.20379 | 0.27583 | −3E−05 | C | −7.2103 | −4.2218 | 1.52162 |
| C | 5.50715 | −0.7913 | −2E−05 | C | −7.2115 | −4.2209 | −1.5225 |
| S | 1.95893 | −0.9587 | −3E−05 | C | −9.2245 | −2.4938 | 0.00088 |
| C | 1.25122 | 1.55585 | −2E−05 | C | 7.21083 | −4.2214 | 1.52195 |
| C | 0.71212 | 0.28281 | −3E−05 | C | 9.22451 | −2.4936 | 0.00035 |
| C | −0.7122 | 0.28281 | −2E−05 | C | 7.21131 | −4.2212 | −1.5222 |
| C | −1.2513 | 1.55585 | −1E−05 | H | −9.4183 | −1.8769 | 0.88414 |
| S | −1E−05 | 2.78121 | −1E−05 | H | −9.9377 | −3.3267 | 0.00097 |
| C | −2.6804 | 1.57475 | −1E−05 | H | −9.419 | −1.8765 | −0.8819 |
| C | −3.2038 | 0.27585 | −2E−05 | H | −6.1871 | −4.6083 | 1.56708 |
| S | −1.959 | −0.9587 | −3E−05 | H | −7.8985 | −5.0758 | 1.50656 |
| C | −3.7881 | 2.48295 | 0.00002 | H | −7.3862 | −3.6532 | 2.44028 |
| C | −4.9879 | 1.68618 | 0.00002 | H | −7.8998 | −5.0749 | −1.5074 |
| C | −4.6275 | 0.29021 | 0 | H | −6.1884 | −4.6074 | −1.569 |
| C | −5.5072 | −0.7913 | −1E−05 | H | −7.3882 | −3.6517 | −2.4407 |
| H | 2.97771 | 4.48603 | −1E−05 | H | 6.18813 | −4.6077 | −1.5684 |
| H | 5.20237 | 5.57337 | −1E−05 | H | 7.89956 | −5.0751 | −1.507 |
| H | 7.14565 | 1.72614 | −2E−05 | H | 7.38775 | −3.6522 | −2.4405 |
| H | 7.27315 | 4.20151 | −1E−05 | H | 7.38699 | −3.6526 | 2.44044 |
| C | −3.8806 | 3.87979 | 0.00003 | H | 7.89908 | −5.0754 | 1.50688 |
| C | −5.1298 | 4.48847 | 0.00005 | H | 6.18764 | −4.608 | 1.56781 |
| C | −6.3028 | 3.70969 | 0.00005 | H | 9.41844 | −1.8765 | 0.88345 |
| C | −6.2363 | 2.32249 | 0.00004 | H | 9.41871 | −1.8764 | −0.8826 |
| | | | | H | 9.93774 | −3.3265 | 0.0004 |

In view of the many possible embodiments to which the principles of the disclosed compounds, articles of manufacture, and methods may be applied, it should be recognized that the illustrated embodiments are only preferred examples of the invention and should not be taken as limiting the scope of the invention.

We claim:

1. A compound having a formula

Formula 1(A)

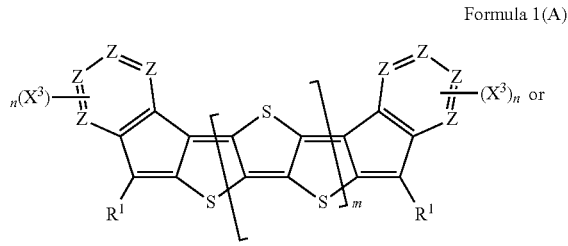

Formula (1)B

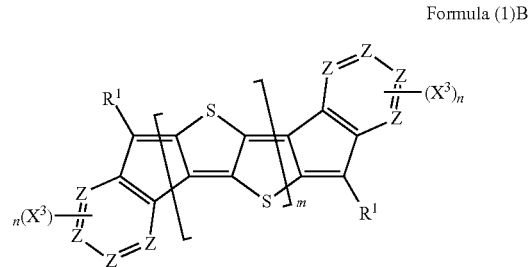

wherein each R¹ independently is alkynyl, substituted alkynyl wherein a hydrogen atom of the alkynyl group is replaced with a halogen, an alkyl group, an alkenyl group, an alkynyl group, an aryl group, a heteroaryl group, a cycloalkyl group, a heteroalkyl group, a cycloheteroalkyl group, an amino group, a haloalkyl group, an alkoxy group, a hydroxy group, an amide group, a ketone group, a nitro group, an azide group, a carboxyl group, an aldehyde group, an ester group, an ether group, a thiol group, a thioether group, or a cyano group, aryl, or substituted aryl wherein at least one hydrogen atom of the aryl group is replaced with a halogen, an alkyl group, an alkenyl group, an alkynyl group, an aryl group, a heteroaryl group, a cycloalkyl group, a heteroalkyl group, a cycloheteroalkyl group, an amino group, a haloalkyl group, an alkoxy group, a hydroxy group, an amide group, a ketone group, a nitro group, an azide group, a carboxyl group, an aldehyde group, an ester group, an ether group, a thiol group, a thioether group, or a cyano group; each Z independently is carbon or nitrogen; each X³ independently is halogen, alkyl, alkenyl, alkynyl, aryl, cycloalkyl, heteroalkyl, amino, haloalkyl, alkoxy, hydroxy, amide, nitro, azide, carboxyl, ester, ether, thiol, thioether, or cyano; each n independently is 0, 1, 2, 3, or 4; and each m independently is 0, 1, 2, 3, 4, 5, 6, 7, 8, 9, or 10.

2. The compound of claim 1, wherein one or more Z is carbon.

3. The compound of claim 1, wherein R¹ is aryl.

4. The compound of claim 1, wherein R¹ is substituted alkynyl.

5. The compound of claim 1, wherein R¹ is an alkynyl silane having a formula

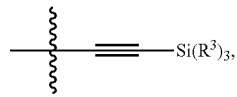

wherein each R³ independently is alkyl, alkenyl, alkynyl, alkoxy, or aryl.

6. The compound of claim 5, wherein each R³ independently is methyl, ethyl, or isopropyl.

7. The compound of claim 5, wherein each R³ independently is $C_{1-10}$alkyl or $C_{1-10}$alkoxy.

8. The compound of claim 1, wherein R¹ is substituted aryl.

9. The compound of claim 8, wherein R¹ is substituted aryl wherein the aryl group is substituted with 1 to 5 substituents, wherein each substituent independently is halogen, alkyl, alkenyl, alkynyl, aryl, heteroaryl, cycloalkyl, heteroalkyl, cycloheteroalkyl, amino, haloalkyl, alkoxy, hydroxy, amide, nitro, azide, carboxyl, ester, ether, thiol, thioether, or cyano.

10. The compound of claim 9, wherein R¹ is substituted aryl wherein the aryl group is substituted with 1 to 5 substituents, wherein each substituent independently is fluoro, bromo, iodo, chloro, trifluoromethyl, or methyl.

11. The compound of claim 1 having a structure

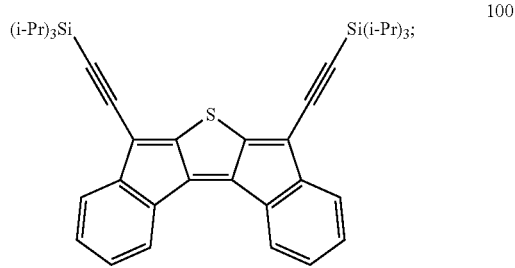

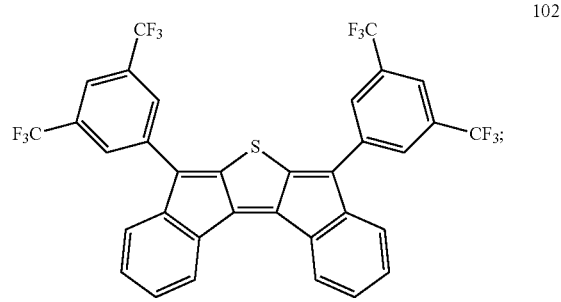

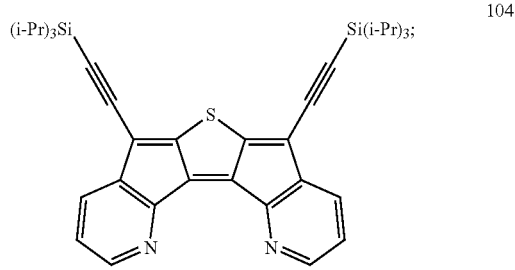

-continued
106
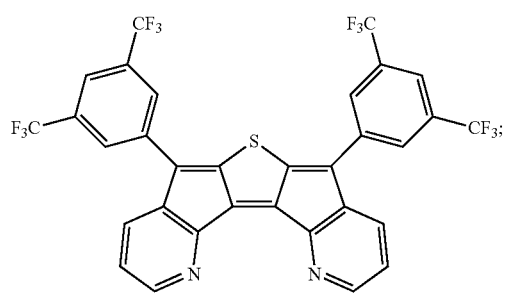
120
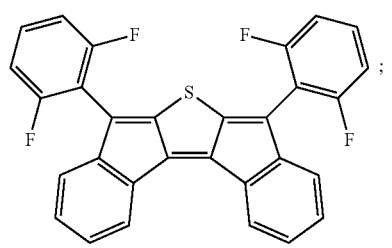
126
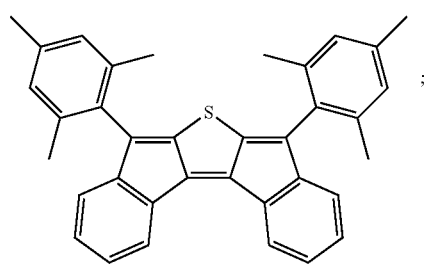
128
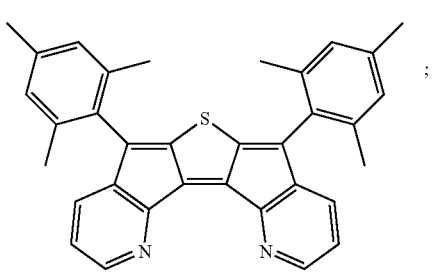
130
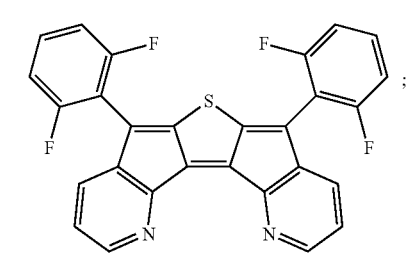
150
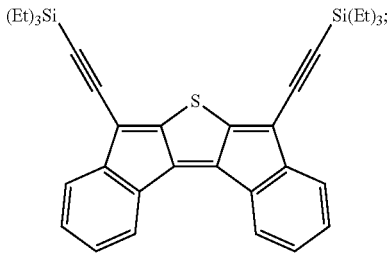
-continued
152
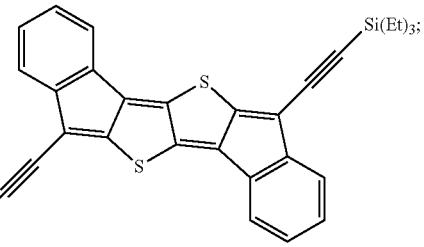
154
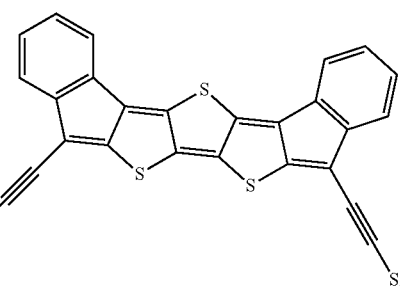
156
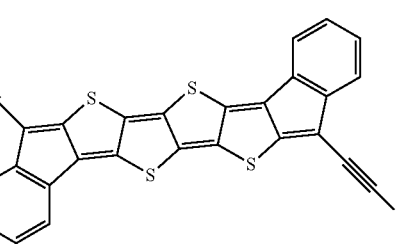
158
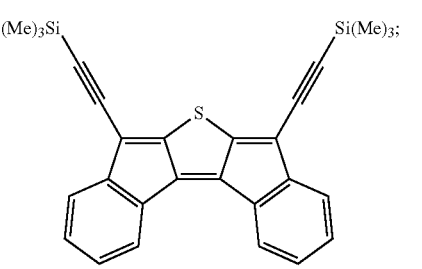
160
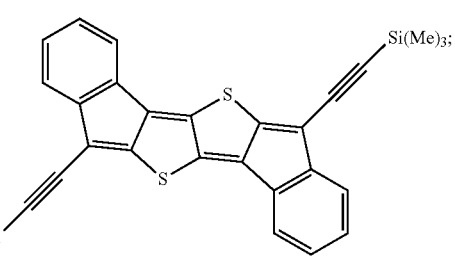

162

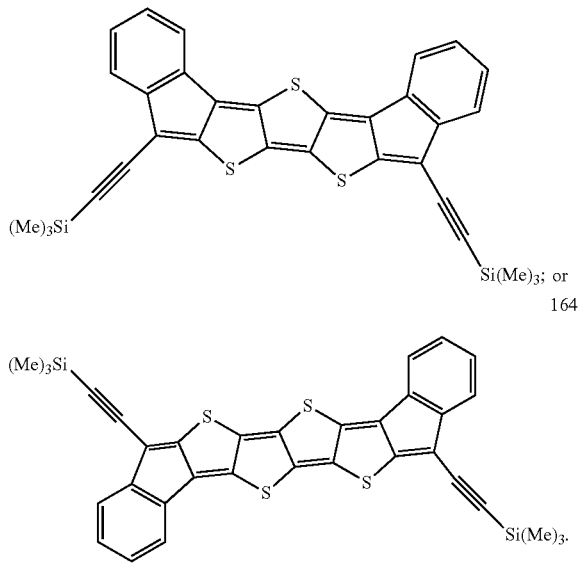

(Me)₃Si

Si(Me)₃; or

164

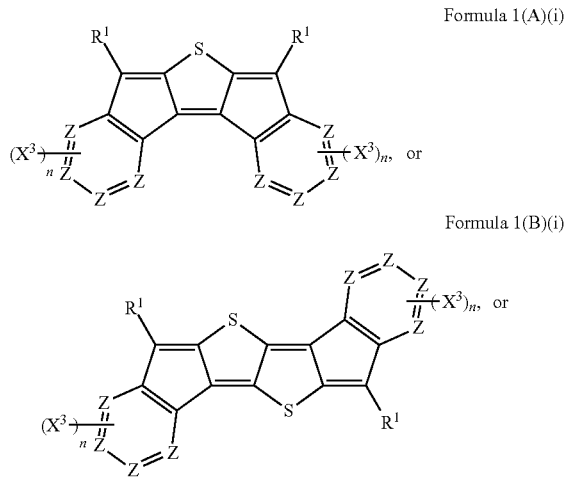

(Me)₃Si

Si(Me)₃.

12. An apparatus comprising an organic light-emitting diode (OLED) device, an organic field-effect transistor (OFET) device, or an organic photovoltaic cell (OPV) device and further comprising a compound of claim 1.

13. The compound of claim 1 having a formula

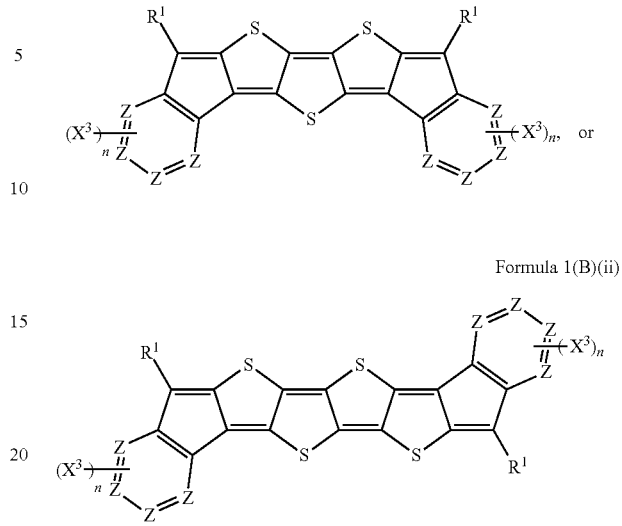

wherein each $R^1$ independently is alkynyl, substituted alkynyl wherein a hydrogen atom of the alkynyl group is replaced with a halogen, an alkyl group, an alkenyl group, an alkynyl group, an aryl group, a heteroaryl group, a cycloalkyl group, a heteroalkyl group, a cycloheteroalkyl group, an amino group, a haloalkyl group, an alkoxy group, a hydroxy group, an amide group, a ketone group, a nitro group, an azide group, a carboxyl group, an aldehyde group, an ester group, an ether group, a thiol group, a thioether group, or a cyano group, aryl, or substituted aryl wherein at least one hydrogen atom of the aryl group is replaced with a halogen, an alkyl group, an alkenyl group, an alkynyl group, an aryl group, a heteroaryl group, a cycloalkyl group, a heteroalkyl group, a cycloheteroalkyl group, an amino group, a haloalkyl group, an alkoxy group, a hydroxy group, an amide group, a ketone group, a nitro group, an azide group, a carboxyl group, an aldehyde group, an ester group, an ether group, a thiol group, a thioether group, or a cyano group; each Z independently is carbon or nitrogen; each $X^3$ independently is halogen, alkyl, alkenyl, alkynyl, aryl, cycloalkyl, heteroalkyl, amino, haloalkyl, alkoxy, hydroxy, amide, nitro, azide, carboxyl, ester, ether, thiol, thioether, or cyano; and each n independently is 0, 1, 2, 3, or 4.

* * * * *